United States Patent
Brubaker

(10) Patent No.: US 10,344,007 B2
(45) Date of Patent: Jul. 9, 2019

(54) CREATINE PRODRUGS, COMPOSITIONS AND METHODS OF USE THEREOF

(71) Applicant: Farmington Pharma Development, Cheshire, CT (US)

(72) Inventor: William F. Brubaker, Cheshire, CT (US)

(73) Assignee: FARMINGTON PHARMA DEVELOPMENT, Cheshire, CT (US)

( * ) Notice: Subject to any disclaimer, the term of this patent is extended or adjusted under 35 U.S.C. 154(b) by 0 days.

(21) Appl. No.: 15/481,568

(22) Filed: Apr. 7, 2017

(65) Prior Publication Data

US 2017/0342039 A1    Nov. 30, 2017

Related U.S. Application Data

(63) Continuation of application No. 14/975,950, filed on Dec. 21, 2015, now Pat. No. 9,617,230.

(60) Provisional application No. 62/095,295, filed on Dec. 22, 2014.

(51) Int. Cl.
| | |
|---|---|
| *C07D 273/06* | (2006.01) |
| *C07C 279/14* | (2006.01) |
| *C07C 279/24* | (2006.01) |
| *C07D 271/07* | (2006.01) |
| *C07D 273/04* | (2006.01) |

(52) U.S. Cl.
CPC .......... *C07D 273/06* (2013.01); *C07C 279/14* (2013.01); *C07C 279/24* (2013.01); *C07D 271/07* (2013.01); *C07D 273/04* (2013.01); *C07B 2200/05* (2013.01)

(58) Field of Classification Search
CPC .. C07D 273/06; C07D 271/07; C07D 273/04; C07C 279/14; C07C 279/24
USPC .................................................. 514/211.08
See application file for complete search history.

(56) References Cited

U.S. PATENT DOCUMENTS

| | | | |
|---|---|---|---|
| 9,617,230 | B2 | 4/2017 | Brubaker |
| 2008/0051371 | A1 | 2/2008 | Zerangue et al. |

FOREIGN PATENT DOCUMENTS

| | | |
|---|---|---|
| WO | WO 2009/143630 | 12/2009 |
| WO | WO 2010/005692 | 1/2010 |
| WO | WO 2013/043580 | 3/2013 |
| WO | WO 2014/018570 | 1/2014 |
| WO | WO 2016/106284 | 6/2016 |

OTHER PUBLICATIONS

Gavezzotti Acc. Chem. Res 1994, 27, 309-314 (Year: 1994).*
International Search Report and Written Opinion for International Patent Application No. PCT/US2015/067283, dated Aug. 19, 2016, 11 pages.
Extended European Search Report for European Application No. 15874283.3, dated Sep. 5, 2018, 8 pages.
Partial Supplementary European Search Report and Opinion for European Application No. 15874283.3, dated Jun. 4, 2018, 9 pages.

* cited by examiner

*Primary Examiner* — Yevgeny Valenrod
(74) *Attorney, Agent, or Firm* — Cooley LLP

(57) ABSTRACT

The invention describes membrane permeable creatine prodrugs, pharmaceutical compositions comprising membrane permeable creatine prodrugs, and methods of treating diseases such as ischemia, heart failure, neurodegenerative disorders and genetic disorders affecting the creatine kinase system comprising administering creatine prodrugs or pharmaceutical compositions thereof. The invention also describes treating a genetic disease affecting the creatine kinase system, such as, for example, a creatine transporter disorder or a creatine synthesis disorder comprising administering creatine prodrugs or pharmaceutical compositions thereof.

13 Claims, No Drawings

CREATINE PRODRUGS, COMPOSITIONS AND METHODS OF USE THEREOF

CROSS-REFERENCE TO RELATED APPLICATION

This application is a continuation of U.S. patent application Ser. No. 14/975,950 filed on Dec. 21, 2015 with the title "CREATINE PRODRUGS, COMPOSITIONS AND METHODS OF USE THEREOF", which claims the benefit of priority to U.S. Provisional Application No. 62/095,295, filed on Dec. 22, 2014 and entitled "CREATINE PRODRUGS, COMPOSITIONS AND METHODS OF USE THEREOF", the disclosures of which are hereby incorporated by reference in their entireties for all purposes.

FIELD OF THE INVENTION

The invention describes membrane permeable creatine prodrugs, pharmaceutical compositions comprising membrane permeable creatine prodrugs, and methods of treating diseases, such as, for example, ischemia, heart failure, neurodegenerative disorders and genetic disorders affecting the creatine kinase system comprising administering creatine prodrugs or pharmaceutical compositions thereof. In some embodiments the invention describes treating a genetic disease affecting the creatine kinase system, such as, for example, a creatine transporter disorder or a creatine synthesis disorder comprising administering creatine prodrugs or pharmaceutical compositions thereof.

BACKGROUND OF THE INVENTION

Creatine plays an important part in cellular energy metabolism, constituting as high-energy phosphocreatine a significant muscular energy reserve in addition to adenosine triphosphate (ATP). In the resting state of the muscle, ATP can transfer a phosphate group onto creatine, so forming phosphocreatine, which is then in direct equilibrium with ATP. During muscular work, it is of vital importance to replenish ATP stores as rapidly as possible. Phosphocreatine is available for this purpose during the first seconds of maximum muscle load, this substance is capable in a very rapid reaction of transferring a phosphate group onto adenosine diphosphate by the enzyme creatine kinase, so reforming ATP. The creatine kinase system has a dual role in intracellular energy metabolism-functioning as an energy buffer to restore depleted ATP levels at sites of high ATP hydrolysis, and to transferring energy in the form of phosphocreatine from the mitochondria to other pans of the cell by a process involving intermediate energy carriers, several enzymatic reactions, and diffusion through various intracellular structures.

Many pathological disease slates arise from a dysfunction in energy metabolism. Cellular depletion of ATP stores, as occurs for example during tissue ischemia, results in impaired tissue functions and cell death. Of foremost medical relevance, ischemia-related cardiovascular disease such as stroke and heart attack remains a leading cause of death and morbidity in North America and Europe. Thus, strategies that can prevent or reverse ischemia-related tissue damage are expected to have a major impact on public health. Energy depletion also contributes to tissue damage during surgery and is a common cause of organ transplant failure. Furthermore, reperfusion with oxygen-containing solutions can further exacerbate tissue health through production of oxygen radicals. Therefore, a method to rapidly restore ATP levels without causing reperfusion injury is likely to have many therapeutic applications. Neurodegenerative diseases such as Parkinson's disease, Alzheimer's disease, and Huntington's disease are associated with impaired energy metabolism, and strategies for improving ATP metabolism could potentially minimize loss of neurons and thereby improve the prognosis of patients with these diseases. Finally, impaired energy metabolism is an important factor in muscle fatigue and limits physical endurance. Therefore, a method of preventing or reversing ATP depletion in ischemic or metabolically active tissues is likely to have broad clinical utility in a wide range of indications.

Creatine supplementation increases intracellular creatine phosphate levels (Harris et al., Clinical Sci 1992, 83, 367-74). Creatine readily crosses the blood-brain barrier in healthy individuals and brain creatine levels can be increased via oral administration (Dechent et al., Am J Physiol 1999, 277, R698-704). Prolonged creatine supplementation can elevate the cellular pools of creatine phosphate and increase resistance to tissue ischemia and muscle fatigue. Thus, although administration of creatine may have some therapeutic usefulness, a modified creatine molecule mat is mote stable and is more permeable to barrier tissues and cellular membranes would have enhanced therapeutic value.

Creatine prodrugs of the invention are designed to be stable in biological fluids, to enter cells by either passive diffusion or active transport, and to release creatine into the cellular cytoplasm. Such prodrugs can also cross important barrier tissues such as the intestinal mucosa, the blood-brain barrier, and the blood-placental barrier. Because of the ability to pass through biological membranes, creatine prodrugs can restore and maintain energy homeostasis in ATP depleted cells via the creatine kinase system, and rapidly restore ATP levels to protect tissues from further ischemic stress. Creatine prodrugs having a higher tree energy or lower affinity for creatine kinase, and which can regenerate ATP under more severe conditions of energy depletion are also disclosed. Creatine prodrugs of the invention can also be used to deliver sustained systemic concentrations of creatine. The invention is directed to these, as well as other, important ends.

SUMMARY OF THE INVENTION

The present invention relates to membrane permeable creatine prodrugs, pharmaceutical compositions comprising the membrane permeable creatine prodrugs, and methods of using membrane permeable creatine prodrugs, and pharmaceutical compositions thereof. In some embodiments the invention describes treating a genetic disease affecting the creatine kinase system, such as, for example, a creatine transporter disorder or a creatine synthesis disorder comprising administering creatine prodrugs or pharmaceutical compositions thereof.

In one embodiment, the invention describes compounds of Formula (I) or a pharmaceutically acceptable salt, solvate, tautomer or stereoisomer thereof:

wherein the compound of formula (I) is

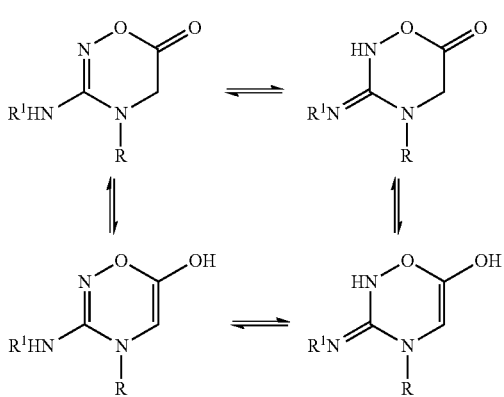

wherein:
R is —CH₃ or —CD₃;
R¹ is hydrogen, —OR², —C(O)OR², —C(O)R²,

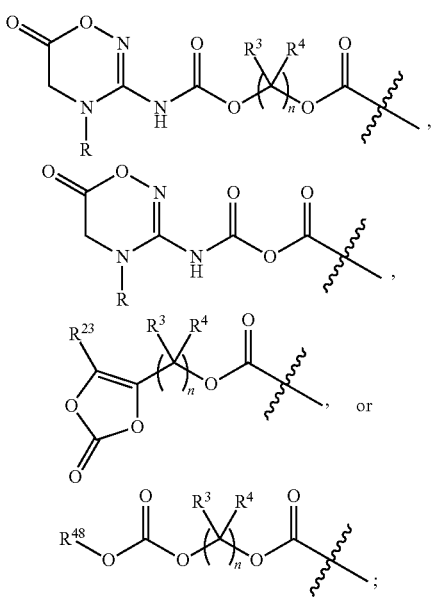

n is an integer from 1 to 2,
each R² is independently hydrogen, $C_{1-12}$ alkyl, substituted $C_{1-12}$ alkyl, $C_{1-12}$ heteroalkyl, substituted $C_{1-12}$ heteroalkyl, $C_{3-12}$ cycloalkyl, substituted $C_{3-12}$ cycloalkyl, $C_{3-12}$ cycloalkylalkyl, substituted $C_{4-20}$ cycloalkylalkyl, $C_{4-20}$ heterocycloalkylalkyl, substituted $C_{4-20}$ heterocycloalkylalkyl, $C_{5-12}$ aryl, substituted $C_{5-12}$ aryl, $C_{5-12}$ heteroaryl, substituted $C_{5-12}$ heteroaryl, $C_{6-20}$ arylalkyl, substituted $C_{6-20}$ arylalkyl, $C_{6-20}$ heteroarylalkyl or substituted $C_{6-20}$ heteroarylalkyl;
each R³ and R⁴ is independently hydrogen, $C_{1-12}$ alkyl or substituted $C_{1-12}$ alkyl;
R²³ is hydrogen, $C_{1-12}$ alkyl, substituted $C_{1-12}$ alkyl, $C_{5-12}$ cycloalkyl, substituted $C_{5-12}$ cycloalkyl, $C_{5-12}$ aryl, and $C_{5-12}$ substituted aryl, —C(O)—OR²² or —C(O)—R²²;
R²² is $C_{1-12}$ alkyl, substituted $C_{1-12}$ alkyl, $C_{1-12}$ heteroalkyl, substituted $C_{1-12}$ heteroalkyl, $C_{3-12}$ cycloalkyl, substituted $C_{3-12}$ cycloalkyl, $C_{4-20}$ cycloalkylalkyl, substituted $C_{4-20}$ cycloalkylalkyl, $C_{4-20}$ heterocycloalkylalkyl, substituted $C_{4-20}$ heterocycloalkylalkyl, $C_{5-12}$ aryl, substituted $C_{5-12}$ aryl, $C_{5-12}$ heteroaryl, substituted $C_{5-12}$ heteroaryl, $C_{6-20}$ arylalkyl, substituted $C_{6-20}$ arylalkyl, $C_{6-20}$ heteroarylalkyl or substituted $C_{6-20}$ heteroarylalkyl; and
R⁴⁸ is $C_{1-12}$ alkyl or substituted $C_{1-12}$ alkyl.

Yet another embodiment describes compounds of Formula (III) or a pharmaceutically acceptable salt, solvate, tautomer or stereoisomer thereof:
wherein the compound of Formula (III) is;

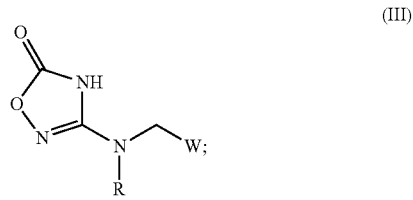

wherein:
W is —CH₂OH or —C(O)OR⁷;
R is —CH₃ or —CD₃;
R⁷ is hydrogen, $C_{1-12}$ alkyl, substituted $C_{1-12}$ alkyl, $C_{1-12}$ heteroalkyl, substituted $C_{1-12}$ heteroalkyl, $C_{3-12}$ cycloalkyl, substituted $C_{3-12}$ cycloalkyl, $C_{4-20}$ cycloalkylalkyl, substituted $C_{4-20}$ cycloalkylalkyl, $C_{4-20}$ heterocycloalkylalkyl, substituted $C_{4-20}$ heterocycloalkylalkyl, $C_{5-12}$ aryl, substituted $C_{5-12}$ aryl, $C_{5-12}$ heteroaryl, substituted $C_{5-12}$ heteroaryl, $C_{6-20}$ arylalkyl, substituted $C_{6-20}$ arylalkyl, $C_{6-20}$ heteroarylalkyl, substituted $C_{6-20}$ heteroarylalkyl, —C(O)R⁵, —C(O)OR⁵, —C(O)(NR³R⁴), —C(R³R⁴)—C(O)OR²², —C(R³R⁴)—(O)C(O)R²², —C(R³R⁴)—(O)C(O)—OR²²,

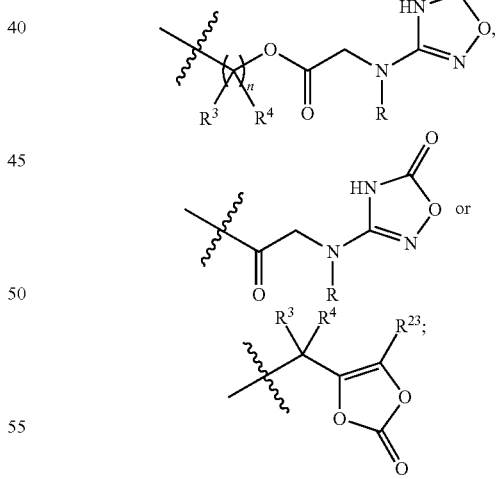

n is an integer from 1 to 2;
each R³ and R⁴ is independently hydrogen, $C_{1-12}$ alkyl or substituted $C_{1-12}$ alkyl; and
R⁵ is hydrogen, $C_{1-12}$ alkyl, substituted $C_{1-12}$ alkyl, $C_{1-12}$ heteroalkyl, substituted $C_{1-12}$ heteroalkyl, $C_{3-12}$ cycloalkyl, substituted $C_{3-12}$ cycloalkyl, $C_{4-20}$ cycloalkylalkyl, substituted $C_{4-20}$ cycloalkylalkyl, $C_{4-20}$ heterocycloalkylalkyl, substituted $C_{4-20}$ heterocycloalkylalkyl, $C_{5-12}$ aryl, substituted $C_{5-12}$ aryl, $C_{5-12}$ heteroaryl, substituted $C_{5-12}$ heteroaryl, $C_{6-20}$ arylalkyl, substituted $C_{6-20}$ arylalkyl, $C_{6-20}$ heteroarylalkyl or substituted $C_{6-20}$ heteroarylalkyl;

$R^{23}$ is hydrogen, $C_{1-12}$ alkyl, substituted $C_{1-12}$ alkyl, $C_{5-12}$ cycloalkyl, substituted $C_{5-12}$ cycloalkyl, $C_{5-12}$ cycloalkyl, $C_{5-12}$ aryl, and $C_{5-12}$ substituted aryl, —C(O)—O $R^{22}$ or —C(O)—$R^{22}$; and $R^{22}$ is $C_{1-12}$ alkyl, substituted $C_{1-12}$ alkyl, $C_{1-12}$ heteroalkyl, substituted $C_{1-12}$ heteroalkyl, $C_{3-12}$ cycloalkyl, substituted $C_{3-12}$ cycloalkyl, $C_{4-20}$ cycloalkylalkyl, substituted $C_{4-20}$ cycloalkylalkyl, $C_{4-20}$ cycloalkylalkyl, $C_{4-20}$ heterocycloalkylalkyl, substituted $C_{4-20}$ heterocycloalkylalkyl, $C_{5-12}$ aryl, substituted $C_{5-12}$ aryl, substituted $C_{5-20}$ aryl, $C_{5-12}$ heteroaryl, substituted $C_{5-12}$ heteroaryl, $C_{6-20}$ arylalkyl, substituted $C_{6-20}$ arylalkyl, $C_{6-20}$ heteroarylalkyl or substituted $C_{6-20}$ heteroarylalkyl.

Yet another embodiment describes compounds of Formula (VI) or a pharmaceutically acceptable salt, solvate, tautomer or stereoisomer thereof:

wherein the compound of Formula (VI) is:

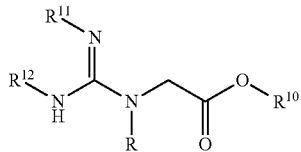

(VI)

wherein:

R is —$CH_3$ or —$CD_3$;

$R^{10}$ is hydrogen, $C_{1-12}$ alkyl, substituted $C_{1-12}$ alkyl, $C_{1-12}$ heteroalkyl, substituted $C_{1-12}$ heteroalkyl, $C_{3-12}$ cycloalkyl, substituted $C_{3-12}$ cycloalkyl, $C_{4-20}$ cycloalkylalkyl, substituted $C_{4-20}$ cycloalkylalkyl, $C_{4-20}$ heterocycloalkylalkyl, substituted $C_{4-20}$ heterocycloalkylalkyl, $C_{5-12}$ aryl, substituted $C_{5-12}$ aryl, $C_{5-12}$ heteroaryl, substituted $C_{5-12}$ heteroaryl, $C_{6-20}$ arylalkyl, substituted $C_{6-20}$ arylalkyl, $C_{6-20}$ heteroarylalkyl, substituted $C_{6-20}$ heteroarylalkyl, —C(O)$R^5$, —C(O)O$R^5$, —C(O)(N$R^3R^4$), —C($R^3R^4$)—C(O)O$R^{22}$, —C($R^3R^4$)—(O)C(O) $R^{22}$, —C($R^3R^4$)—(O)C(O)—O$R^{22}$;

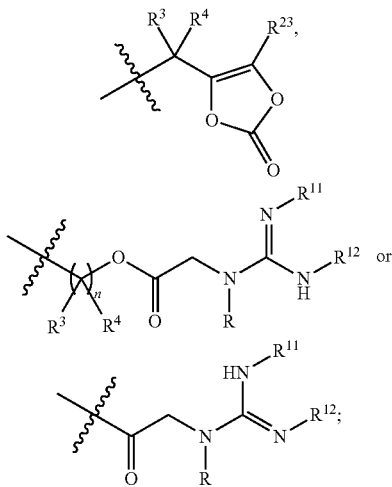

$R^{11}$ and $R^{12}$ are each independently hydrogen or —O$R^{13}$; or $R^{11}$ and $R^{12}$ are each —C(O)$R^5$, with the proviso that both $R^{11}$ and $R^{12}$ cannot be hydrogen;

$R^{13}$ is independently hydrogen, $C_{1-12}$ alkyl, substituted $C_{1-12}$ alkyl, $C_{1-12}$ heteroalkyl, substituted $C_{1-12}$ heteroalkyl, $C_{3-12}$ cycloalkyl, substituted $C_{3-12}$ cycloalkyl, $C_{4-20}$ cycloalkylalkyl, substituted $C_{4-20}$ cycloalkylalkyl, $C_{4-20}$ heterocycloalkylalkyl, substituted $C_{4-20}$ heterocycloalkylalkyl, $C_{5-12}$ aryl, substituted $C_{5-12}$ aryl, $C_{5-12}$ heteroaryl, substituted $C_{5-12}$ heteroaryl, $C_{6-20}$ arylalkyl, substituted $C_{6-20}$ arylalkyl, $C_{6-20}$ heteroarylalkyl, substituted $C_{6-20}$ heteroarylalkyl —CH(O$R^5$), —C(O)$R^5$, —C(O)O$R^5$ or —C(O)(N$R^3R^4$);

each $R^3$ and $R^4$ is independently hydrogen, $C_{1-12}$ alkyl or substituted $C_{1-12}$ alkyl;

$R^5$ is hydrogen, $C_{1-12}$ alkyl, substituted $C_{1-12}$ alkyl, $C_{1-12}$ heteroalkyl, substituted $C_{1-12}$ heteroalkyl, $C_{3-12}$ cycloalkyl, substituted $C_{3-12}$ cycloalkyl, $C_{4-20}$ cycloalkylalkyl, substituted $C_{4-20}$ cycloalkylalkyl, $C_{4-20}$ heterocycloalkylalkyl, substituted $C_{4-20}$ heterocycloalkylalkyl, $C_{5-12}$ aryl, substituted $C_{5-12}$ aryl, $C_{5-12}$ heteroaryl, substituted $C_{5-12}$ heteroaryl, $C_{6-20}$ arylalkyl, substituted $C_{6-20}$ arylalkyl, $C_{6-20}$ heteroarylalkyl or substituted $C_{6-20}$ heteroarylalkyl;

$R^{23}$ is hydrogen, $C_{1-12}$ alkyl, substituted $C_{1-12}$ alkyl, $C_{5-12}$ cycloalkyl, substituted $C_{5-12}$ cycloalkyl, $C_{5-12}$ aryl, and $C_{5-12}$ substituted aryl, —C(O)—O$R^{22}$ or —C(O)—$R^{22}$;

$R^{22}$ is $C_{1-12}$ alkyl, substituted $C_{1-12}$ alkyl, $C_{1-12}$ heteroalkyl, substituted $C_{1-12}$ heteroalkyl, $C_{3-12}$ cycloalkyl, substituted $C_{3-12}$ cycloalkyl, $C_{4-20}$ cycloalkylalkyl, substituted $C_{4-20}$ cycloalkylalkyl, $C_{4-20}$ heterocycloalkylalkyl, substituted $C_{4-20}$ heterocycloalkylalkyl, $C_{5-12}$ aryl, substituted $C_{5-12}$ aryl, $C_{5-12}$ heteroaryl, substituted $C_{5-12}$ heteroaryl, $C_{6-20}$ arylalkyl, substituted $C_{6-20}$ arylalkyl, $C_{6-20}$ heteroarylalkyl or substituted $C_{6-20}$ heteroarylalkyl; and n is an integer from 1 to 3.

One other embodiment describes compounds of Formula (VII) or a pharmaceutically acceptable salt, solvate, tautomer or stereoisomer thereof:

wherein the compound of Formula (VII) is:

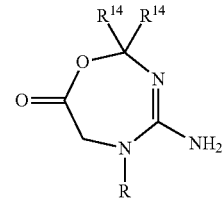

(VII)

wherein:

R is —$CH_3$ or —$CD_3$;

each $R^{14}$ is independently hydrogen, $C_{1-12}$ alkyl, substituted $C_{1-12}$ alkyl, $C_{1-12}$ heteroalkyl, substituted $C_{1-12}$ heteroalkyl, $C_{3-12}$ cycloalkyl, substituted $C_{3-12}$ cycloalkyl, $C_{4-20}$ cycloalkylalkyl, substituted $C_{4-20}$ cycloalkylalkyl, $C_{4-20}$ heterocycloalkylalkyl, substituted $C_{4-20}$ heterocycloalkylalkyl, $C_{5-12}$ aryl, substituted $C_{5-12}$ aryl, $C_{5-12}$ heteroaryl, substituted $C_{5-12}$ heteroaryl, $C_{6-20}$ arylalkyl, substituted $C_{6-20}$ arylalkyl, $C_{6-20}$ heteroarylalkyl, substituted $C_{6-20}$ heteroarylalkyl —CH(O$R^5$), —C(O)$R^5$, —C(O)O$R^5$ or —C(O)(N$R^3R^4$);

each $R^3$ and $R^4$ is independently hydrogen, $C_{1-12}$ alkyl or substituted $C_{1-12}$ alkyl; and $R^5$ is hydrogen, $C_{1-12}$ alkyl, substituted $C_{1-12}$ alkyl, $C_{1-12}$ heteroalkyl, substituted $C_{1-12}$ heteroalkyl, $C_{3-12}$ cycloalkyl, substituted $C_{3-12}$ cycloalkyl, $C_{4-20}$ cycloalkylalkyl, substituted $C_{4-20}$ cycloalkylalkyl, $C_{4-20}$ heterocycloalkylalkyl, substituted $C_{4-20}$ heterocycloalkylalkyl, $C_{5-12}$ aryl, substituted $C_{5-12}$ aryl, $C_{5-12}$ heteroaryl, substituted $C_{5-12}$ heteroaryl, $C_{6-20}$ arylalkyl, substituted $C_{6-20}$ arylalkyl, $C_{6-20}$ heteroarylalkyl or substituted $C_{6-20}$ heteroarylalkyl.

In certain embodiments, the compounds of Formulae (I), (III), (VI), and (VII), can include the following features:

Each R is independently —$CH_3$.
Each R is independently —$CD_3$.
Each n is independently the integer 1.
Each n is independently the integer 2.
Each $R^2$, $R^5$, $R^6$, $R^7$, $R^8$, $R^9$, $R^{10}$, $R^{14}$, $R^{15}$, $R^{18}$ and $R^{22}$ is independently $C_{1-6}$ alkyl, substituted $C_{1-6}$ alkyl, $C_{3-7}$ cycloalkyl, substituted $C_{3-7}$ cycloalkyl, $C_{5-7}$ aryl or substituted $C_{5-7}$ aryl.
Each $R^2$, $R^5$, $R^6$, $R^7$, $R^8$, $R^9$, $R^{10}$, $R^{14}$, $R^{15}$, $R^{18}$ and $R^{22}$ is independently hydrogen, methyl, ethyl, n-propyl, isopropyl, butyl, isobiityl, sec-butyl, tert-butyl, n-pentyl, isopentyl, sec-pentyl, neopentyl, dodecyl, 1,1-dimethoxyethyl, 1,1-diethoxyethyl, phenyl, 4-methoxyphenyl, benzyl, phenethyl, styryl, cyclopropyl, cyclobutyl, cyclopentyl, cyclohexyl, 2-pyridyl, 3-pyridyl or 4-pyridyl.
Each $R^2$, $R^5$, $R^6$, $R^7$, $R^8$, $R^9$, $R^{10}$, $R^{14}$, $R^{15}$, $R^{18}$ and $R^{22}$ is independently hydrogen, methyl, ethyl, n-propyl, isopropyl, n-butyl, isobutyl, sec-butyl, tert-butyl, n-pentyl, isopentyl, sec-pentyl, neopentyl, dodecyl, 1,1-diethoxyethyl, phenyl, cyclohexyl or 3-pyridyl.
Each $R^2$, $R^5$, $R^6$, $R^7$, $R^8$, $R^9$, $R^{10}$, $R^{14}$, $R^{15}$, $R^{18}$ and $R^{22}$ is independently hydrogen, methyl, ethyl, n-propyl, isopropyl, dodecyl, tert-butyl, phenyl or cyclohexyl.
Each $R^2$, $R^5$, $R^6$, $R^7$, $R^8$, $R^9$, $R^{10}$, $R^{14}$, $R^{15}$, $R^{18}$ and $R^{22}$ is independently ethyl, isopropyl or dodecyl.
Each $R^3$ and $R^4$ is independently hydrogen.
Each $R^{23}$ is hydrogen, methyl, ethyl, n-propyl, isopropyl, tert-butyl, dodecyl, phenyl or cyclohexyl.
Each $R^{23}$ is methyl.
Each substituent group is independently halogen, —$NO_2$, —OH, —$NH_2$, —CN, —$CF_3$, —$OCF_3$, =O, $C_{1-12}$ alkyl, substituted $C_{1-12}$ alkyl, $C_{1-12}$ alkoxy or substituted $C_{1-12}$ alkoxy, —$COOR^{10'}$ wherein $R^{10'}$ is hydrogen, $C_{1-3}$ alkyl or —$(NR^{11'})_2$ wherein each $R^{11'}$ is independently hydrogen or $C_{1-3}$ alkyl.

In one embodiment, the compound of Formula (I) is a compound of Formula (X), Formula (XI), Formula (XII), Formula (XIII), Formula (XIV), Formula (XV), Formula (XVa) or Formula (XVb) or a pharmaceutically acceptable salt, solvate, tautomer or stereoisomer thereof;

wherein the compound of Formula (X) is:

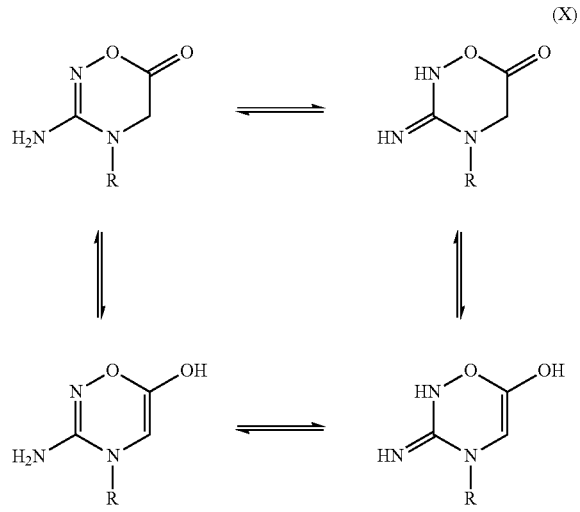

(X)

wherein R is —$CH_3$ or —$CD_3$, wherein the compound of Formula (XI) is:

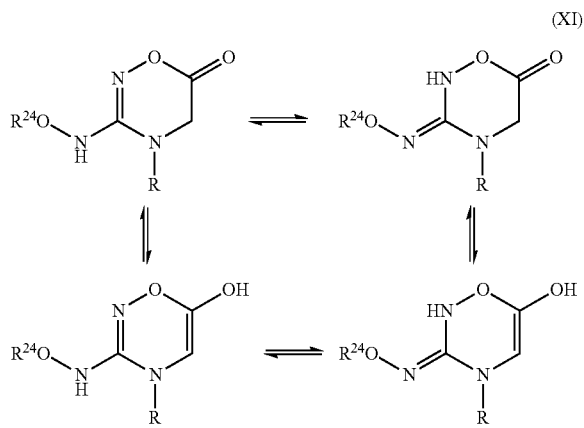

(XI)

wherein R is —$CH_3$ or —$CD_3$; and
$R^{24}$ is hydrogen, methyl, ethyl, n-propyl, isopropyl, tert-butyl, dodecyl, phenyl or cyclohexyl;

wherein the compound of Formula (XII) is:

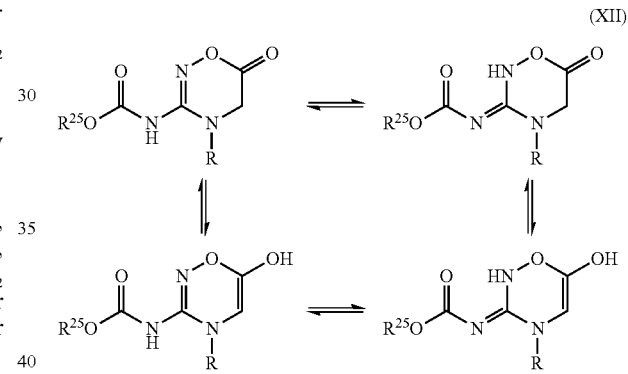

(XII)

wherein R is —$CH_3$ or —$CD_3$; and
$R^{25}$ is hydrogen, methyl, ethyl, n-propyl, isopropyl, tert-butyl, dodecyl, phenyl or cyclohexyl;

wherein the compound of Formula (XIII) is:

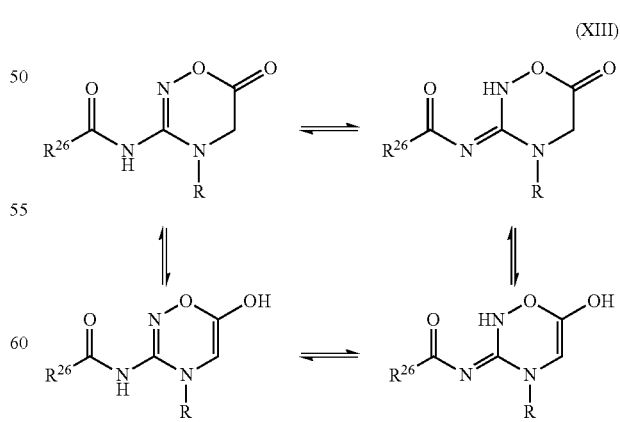

(XIII)

wherein R is —$CH_3$ or —$CD_3$; and
$R^{26}$ is hydrogen, methyl, ethyl, n-propyl, isopropyl, tert-butyl, dodecyl, phenyl or cyclohexyl;

wherein the compound of Formula (XIV) is:

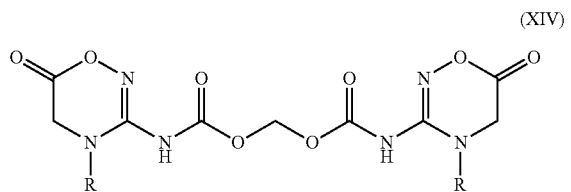

(XIV)

wherein, the compound of Formula (XV) is:

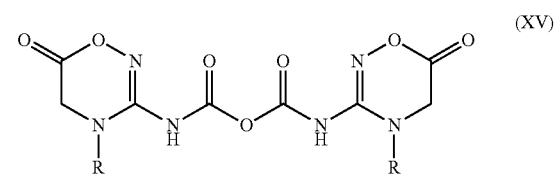

(XV)

wherein R is —CH$_3$ or —CD$_3$;

wherein the compound of Formula (XVa) is:

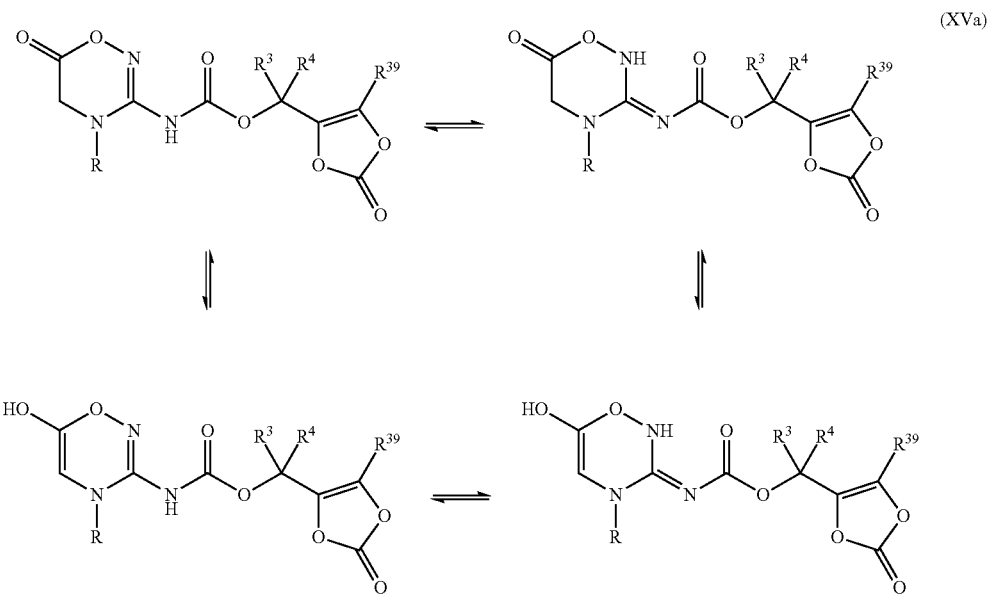

(XVa)

wherein R is —CH$_3$ or —CD$_3$;

R$^{39}$ is hydrogen, methyl, ethyl, n-propyl, isopropyl, tert-butyl, dodecyl, phenyl or cyclohexyl; and R$^3$ and R$^4$ are each independently hydrogen, C$_{1-12}$ alkyl or substituted C$_{1-12}$ alkyl;

wherein the compound of Formula (XVb) is:

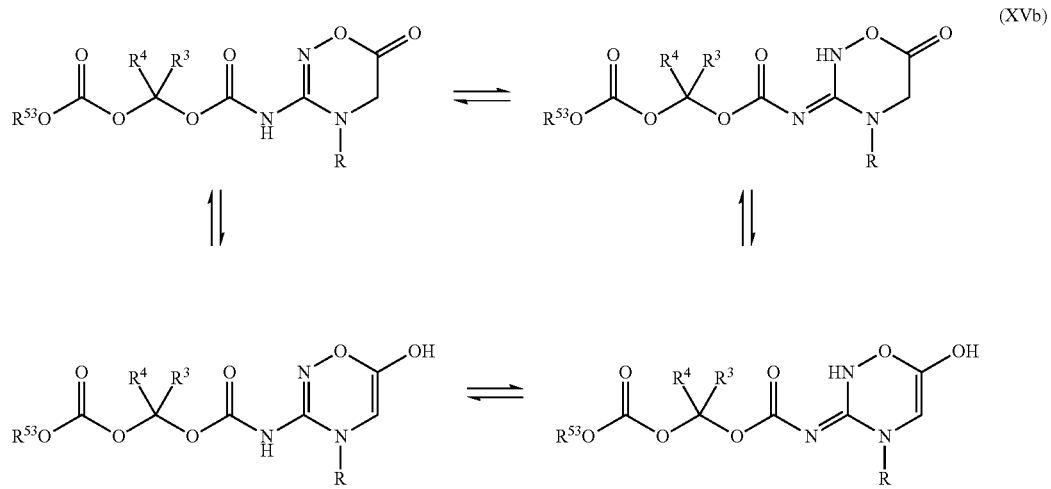

(XVb)

wherein R is —CH$_3$ or —CD$_3$;

R$^3$ and R$^4$ are each independently hydrogen, C$_{1-12}$ alkyl or substituted C$_{1-12}$ alkyl; and R$^{53}$ is C$_{1-12}$ alkyl or substituted C$_{1-12}$ alkyl.

In yet another embodiment, the compound of Formula (III) is a compound of Formula (XVII), Formula (XVIII) or Formula (XIX) or a pharmaceutically acceptable salt, solvate, tautomer or stereoisomer thereof;

wherein the compound of Formula (XVII) is:

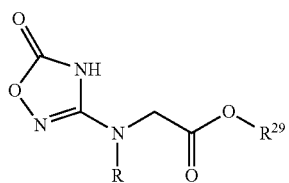

(XVII)

wherein R is —CH$_3$ or —CD$_3$;

R$^{29}$ is hydrogen, methyl, ethyl, n-propyl, isopropyl, tert-butyl, dodecyl, phenyl, -cyclohexyl, —CH$_2$—C(O)OR$^{43}$, —CH$_2$—(O)C(O)R$^{43}$, —CH$_2$—(O)C(O)OR$^{43}$ or

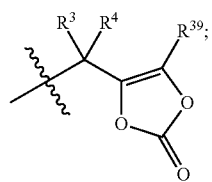

R$^{39}$ is hydrogen, methyl, ethyl, n-propyl, isopropyl, tert-butyl, dodecyl, phenyl or cyclohexyl;

R$^{43}$ is hydrogen, methyl, ethyl, n-propyl, isopropyl, tert-butyl, dodecyl, phenyl or cyclohexyl; and R$^3$ and R$^4$ are each independently hydrogen, C$_{1-12}$ alkyl or substituted C$_{1-12}$ alkyl;

wherein the compound of Formula (XVIII) is:

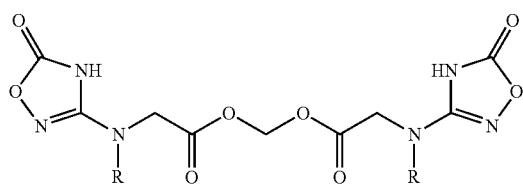

wherein R is —CH$_3$ or —CD$_3$;
wherein the compound of Formula (XIX) is:

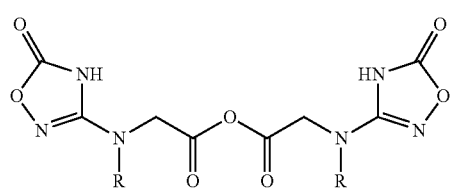

(XIX)

wherein R is —CH$_3$ or —CD$_3$.

In still another embodiment, the compound of Formula (VI) is a compound of Formula (XXII), Formula (XXIII), Formula (XXIV), Formula (XXV), Formula (XXVI), Formula (XXVII) or Formula (XXVIII) or a pharmaceutically acceptable salt, solvate, tautomer or stereoisomer thereof;

wherein the compound of Formula (XXII) is:

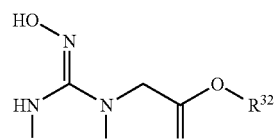

(XXII)

wherein the compound of Formula (XXIII) is:

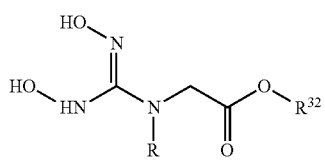

(XXIII)

wherein the compound of Formula (XXIV) is:

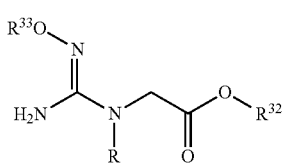

(XXIV)

wherein the compound of Formula (XXV) is:

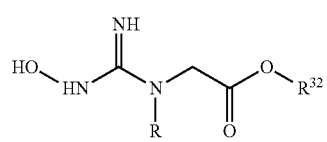

(XXV)

wherein the compound of Formula (XXVI) is:

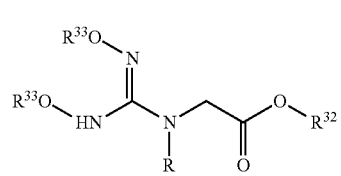

(XXVI)

wherein the compound of Formula (XXVII) is:

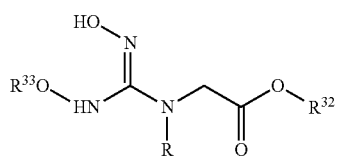

(XXVII)

wherein the compound of Formula (XXVIII) is:

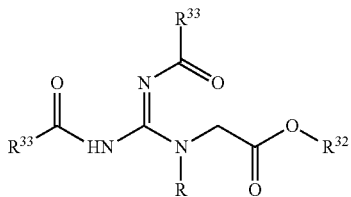
(XXVIII)

wherein R is —CH₃ or —CD₃;
R$^a$ is hydrogen, methyl, ethyl, n-propyl, isopropyl, n-butyl, isobutyl, tert-butyl;
R$^{32}$ is hydrogen, methyl, ethyl, n-propyl, isopropyl, tert-butyl, dodecyl, phenyl, cyclohexyl,
—CH₂—C(O)OR$^{43}$, —CH₂—(O)C(O)R$^{43}$, —CH₂—(O)C(O)OR$^{43}$ or

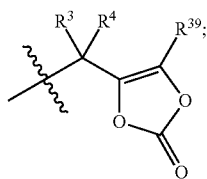

R$^{39}$ is hydrogen, methyl, ethyl, n-propyl, isopropyl, tert-butyl, dodecyl, phenyl or cyclohexyl;
R$^{33}$ is independently hydrogen, methyl, ethyl, n-propyl, isopropyl, tert-butyl, dodecyl, phenyl or cyclohexyl;
R$^{43}$ is hydrogen, methyl, ethyl, n-propyl, isopropyl, tert-butyl, dodecyl, phenyl or cyclohexyl; and
R$^3$ and R$^4$ are each independently hydrogen, C$_{1-12}$ alkyl or substituted C$_{1-12}$ alkyl.

In yet another embodiment, the compound of Formula (VII) is a compound of Formula (XXIX) or a pHarmaceutically acceptable salt, solvate, tautomer or stereoisomer thereof;
wherein the compound of Formula (XXIX) is:

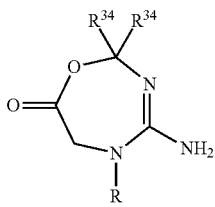
(XXIX)

wherein R is —CH₃ or —CD₃; and
each R$^{34}$ is independently hydrogen, methyl, ethyl, n-propyl, isopropyl, tert-butyl, dodecyl, phenyl or cyclohexyl.

In one embodiment, the invention describes compounds having the following structures:

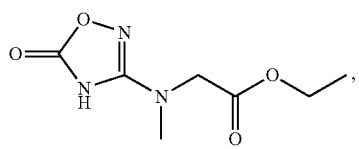

-continued

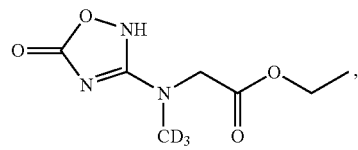

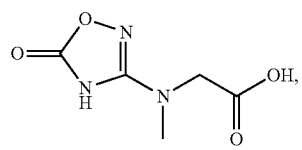

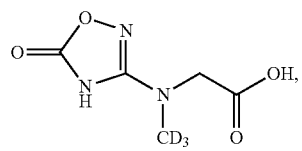

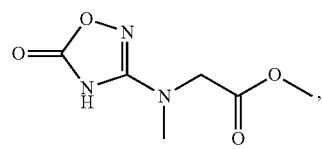

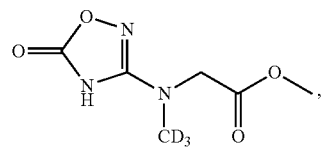

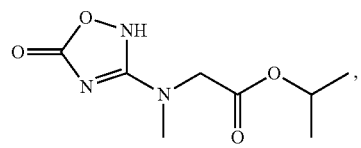

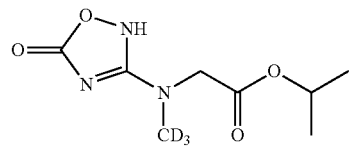

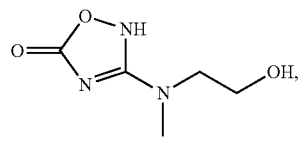

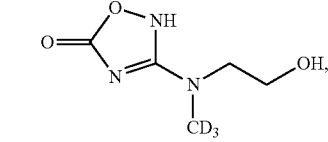

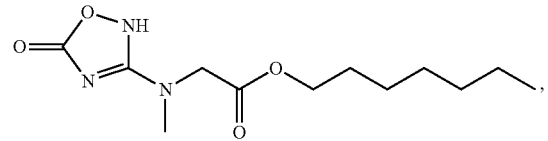

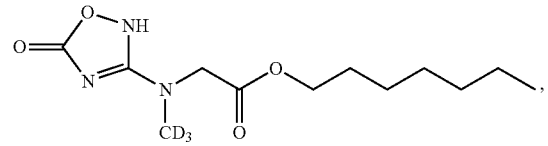

-continued

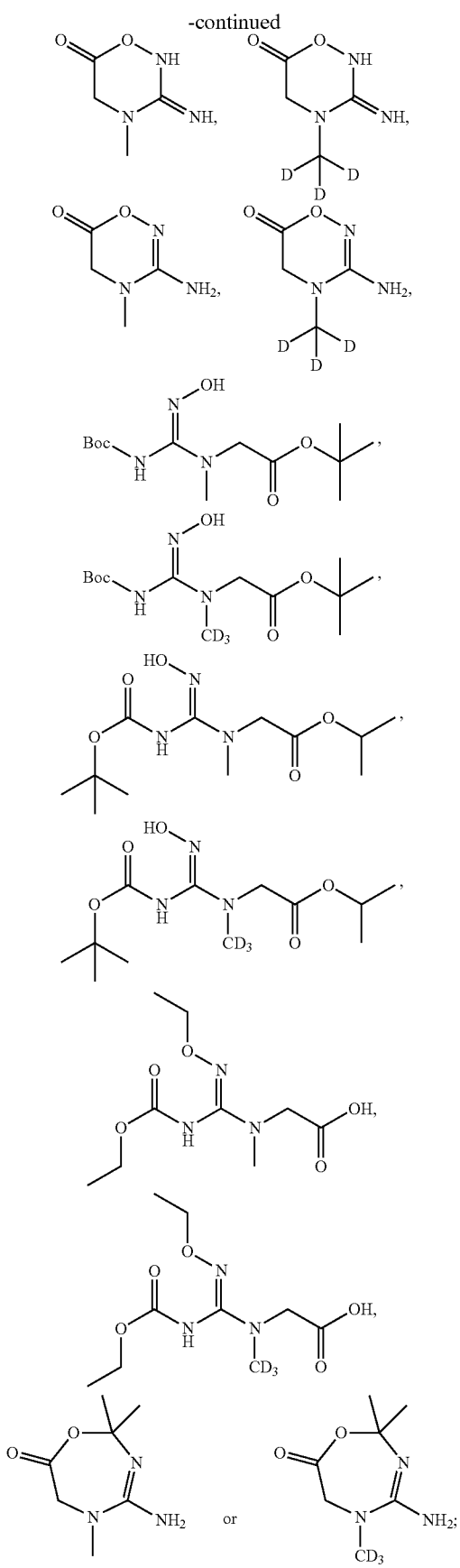

or a pharmaceutically acceptable salt, solvate, tautomer or stereoisomer thereof.

In another embodiment, the invention describes pharmaceutical compositions comprising a therapeutically effective amount of at least one compound, of Formulae (I), (III), (VI), and (VII), and any subgenera or species thereof, or a pharmaceutically acceptable salt, solvate, tautomer or stereoisomer thereof, or a pharmaceutically acceptable solvate of any of the foregoing, and a pharmaceutically acceptable vehicle. In one embodiment, the invention describes pharmaceutical compositions comprising a therapeutically effective amount of at least one compound as disclosed herein, or a pharmaceutically acceptable salt, solvate, tautomer or stereoisomer thereof, or a pharmaceutically acceptable solvate of any of the foregoing, and a pharmaceutically acceptable vehicle.

In some embodiments, the pharmaceutical compositions can be formulated in one or more sustained release oral dosage forms.

In one embodiment, the pharmaceutical composition comprises at least one compound of the present invention in an amount effective for the treatment of a disease in a patient wherein the disease is ischemia, oxidative stress, a neurodegenerative disease, ischemic reperfusion injury, a cardiovascular disease, a genetic disease affecting the creatine kinase system, multiple sclerosis, a psychotic disorder, and muscle fatigue; an amount sufficient to effect energy homeostasis in a tissue or an organ affected by a disease; an amount effective for the enhancement of muscle strength in a patient; an amount effective for the improvement of the viability of a tissue or an organ; or an amount effective for the improvement of the viability of cells. In another embodiment, the pharmaceutical composition comprises at least one compound of the present invention in an amount effective for the treatment of a genetic disease affecting the creatine kinase system. In some embodiments, the pharmaceutical composition comprises at least one compound of the present invention in an amount effective for the treatment of a creatine transporter disorder. In one embodiment, the pharmaceutical composition comprises at least one compound of the present invention in an amount effective for the treatment of a creatine synthesis disorder.

In one embodiment the invention describes methods for treating a disease in a patient associated with a dysfunction in energy metabolism such as ischemia, oxidative stress, a neurodegenerative disease, including amyotrophic lateral sclerosis (ALS), Huntington's disease, Parkinson's disease or Alzheimer's disease, ischemic reperfusion injury, a cardiovascular disease, multiple sclerosis (MS), a psychotic disorder, a genetic disease affecting the creatine kinase system or muscle fatigue in a patient comprising administering to a patient in need of such treatment a therapeutically effective amount of at least one compound of Formulae (I), (III), (VI), (VII), and any subgenera or species thereof, or a pharmaceutically acceptable salt, solvate, tautomer or stereoisomer thereof, or a pharmaceutical composition comprising at least one compound of Formulae (I), (III), (VI), (VII), and any subgenera or species thereof, or a pharmaceutically acceptable salt, solvate, tautomer or stereoisomer thereof.

In another embodiment, methods are described for treating a genetic disease affecting the creatine kinase system, such as, for example, a creatine transporter disorder or a creatine synthesis disorder in a patient comprising administering to a patient in need of such treatment a therapeutically effective amount of at least one compound of Formulae (I), (III), (VI), (VII), and any subgenera or species thereof, or a pharmaceutically acceptable salt, solvate, tautomer or stereoisomer thereof, or a pharmaceutical composition comprising at least one compound of Formulae (I), (III), (VI), (VII), and any subgenera or species thereof, or a pharmaceutically acceptable salt, solvate, tautomer or stereoisomer thereof.

In further embodiments, methods are described for enhancing muscle strength in a patient comprising administering to a patient in need of such enhancement a therapeutically effective amount of at least one compound of Formulae (I), (III), (VI), (VII), and any subgenera or species thereof, or a pharmaceutically acceptable salt, solvate, tautomer or stereoisomer thereof, or a pharmaceutical composition comprising at least one compound of Formulae (I), (III), (VI), (VII), and any subgenera or species thereof, or a pharmaceutically acceptable salt, solvate, tautomer or stereoisomer thereof.

In yet one more embodiment, methods are described for increasing the viability of a tissue or an organ comprising contacting the tissue or the organ with an effective amount of at least one compound of Formulae (I), (III), (VI), (VII), and any subgenera or species thereof, or a pharmaceutically acceptable salt, solvate, tautomer or stereoisomer thereof, or a pharmaceutical composition comprising at least one compound of Formulae (I), (III), (VI), (VII), and any subgenera or species thereof, or a pharmaceutically acceptable salt, solvate, tautomer or stereoisomer thereof.

In still one more embodiment, methods are described for improving the viability of isolated cells comprising contacting the cells with an effective amount of at least one compound of Formulae (I), (III), (VI), (VII), and any subgenera or species thereof, or a pharmaceutically acceptable salt, solvate, tautomer or stereoisomer thereof, or a pharmaceutical composition comprising at least one compound of Formulae (I), (III), (VI), (VII), and any subgenera or species thereof, or a pharmaceutically acceptable salt, solvate, tautomer or stereoisomer thereof.

In another embodiment, methods are described for treating a disease associated with oxidative stress are provided comprising administering to a patient in need of such treatment an effective amount of at least one compound of Formulae (I), (III), (VI), (VII), and any subgenera or species thereof, or a pharmaceutically acceptable salt, solvate, tautomer or stereoisomer thereof, or a pharmaceutical composition comprising at least one compound of Formulae (I), (III), (VI), (VII), and any subgenera or species thereof, or a pharmaceutically acceptable salt, solvate, tautomer or stereoisomer thereof.

In one more embodiment, methods for improving the viability of a tissue or an organ are described for treating a tissue or organ manifesting a dysfunction in energy metabolism are provided comprising contacting at least one compound of Formulae (I), (III), (VI), (VII), and any subgenera or species thereof, or a pharmaceutically acceptable salt, solvate, tautomer or stereoisomer thereof, or a pharmaceutical composition comprising at least one compound of Formulae (I), (III), (VI), (VII), and any subgenera or species thereof, or a pharmaceutically acceptable salt, solvate, tautomer or stereoisomer thereof, with the tissue or organ.

In yet one more embodiment, methods are described for effecting energy homeostasis in a tissue or an organ are provided comprising contacting at least one compound of Formulae (I), (III), (VI), (VII), and any subgenera or species thereof, or a pharmaceutically acceptable salt, solvate, tautomer or stereoisomer thereof, or a pharmaceutical composition comprising at least one compound of Formulae (I), (III), (VI), (VII), and any subgenera or species thereof, or a pharmaceutically acceptable salt, solvate, tautomer or stereoisomer thereof, with the tissue or the organ.

In another embodiment, methods are described for treating an oxidatively stressed, tissue or organ are provided comprising contacting at least one compound of Formulae (I), (III), (VI), (VII), and any subgenera or species thereof, or a pharmaceutically acceptable salt, solvate, tautomer or stereoisomer thereof, or a pharmaceutical composition comprising at least one compound of Formulae (I), (III), (VI), (VII), and any subgenera or species thereof, or a pharmaceutically acceptable salt, solvate, tautomer or stereoisomer thereof, with the tissue or organ.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting.

Other features and advantages of the invention will be apparent from the following detailed description and claims.

DETAILED DESCRIPTION

Definitions

A dash ("-") that is not between two letters or symbols is used to indicate a point of attachment for a moiety or substituent. For example, —CONH$_2$ is attached through the carbon atom.

"Alkyl" by itself or as part of another substituent refers to a saturated or unsaturated, branched or straight-chain, monovalent hydrocarbon radical derived by the removal of one hydrogen atom from a single carbon atom of a parent alkane, alkene or alkyne. Examples of alkyl groups include, but are not limited, to, methyl; ethyls such as ethanyl, ethenyl, and ethynyl; propyls such as propan-1-yl, propan-2-yl, prop-1-en-1-yl, prop-1-en-2-yl, prop-2-en-1-yl (allyl), prop-1-yn-1-yl, prop-2-yn-1-yl, etc.; butyls such as butan-1-yl, butan-2-yl, 2-methyl-propan-1-yl, 2-methyl-propan-2-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, but-1-yn-1-yl, but-1-yn-3-yl, but-3-yn-1-yl, etc.; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds, and groups having mixtures of single, double, and triple carbon-carbon bonds. Where a specific level of saturation is intended, the terms "alkanyl," "alkenyl," and "alkynyl" are used. In certain embodiments, an alkyl group can have from 1 to 20 carbon atoms, in certain embodiments, from 1 to 12 carbon atoms, in certain embodiments, from 1 to 10 carbon atoms, in certain embodiments, from 1 to 6 carbon atoms, and in certain embodiments, from 1 to 3 carbon atoms.

"Alkoxy" by itself or as part of another substituent refers to a radical OR$^{31}$ where R$^{31}$ is chosen from alkyl, heteroalkyl, cycloalkyl, heterocycloalkyl, cycloalkylalkyl, heterocycloalkylalkyl, aryl, heteroaryl, arylalkyl, and heteroarylalkyl, as defined herein. Examples of alkoxy groups include, but are not limited to, methoxy, ethoxy, propoxy, butoxy, cyclohexyloxy, and the like.

"Aryl" by itself or as part of another substituent refers to a monovalent aromatic hydrocarbon radical derived by the removal of one hydrogen atom from a single carbon atom of a parent aromatic ring system. Aryl encompasses 5- and 6-membered carbocyclic aromatic rings, for example, benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene. Aryl encompasses multiple ring systems having at least one carbocyclic aromatic ring fused to at least one carbocyclic aromatic ring, cycloalkyl ring or heterocycloalkyl ring. For example, aryl includes 5- and 6-membered carbocyclic aromatic rings fused to a 5- to 7-membered heterocycloalkyl ring containing one or more heteroatoms chosen from N, O, and S. For such fused, bicyclic ring systems wherein only one of the rings is a carbocyclic aromatic ring, the point of attachment may be at the carbocyclic aromatic ring or the heterocycloalkyl ring. Examples of aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In certain embodiments, an aryl group can have from 6 to 20 carbon atoms, from 6 to 12 carbon atoms, and in certain embodiments, from 6 to 8 carbon atoms. Aryl, however, does not encompass or overlap in any way with heteroaryl, separately defined herein.

"Arylalkyl" by itself or as part of another substituent refers to an acyclic alkyl radical in which one of the hydrogen atoms bonded to a carbon atom, typically a terminal or sp$^3$ carbon atom, is replaced with an aryl group. Examples of arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl or arylalkynyl is used. In certain embodiments, an arylalkyl group is $C_{6-30}$ arylalkyl, e.g., the alkanyl, alkenyl or alkynyl moiety of the arylalkyl group is C.sub.1-10 and the aryl moiety is $C_{6-20}$, in certain embodiments, an arylalkyl group is $C_{6-20}$ arylalkyl, e.g., the alkanyl, aikenyl or alkynyl moiety of the arylalkyl group is $C_{1-8}$ and the aryl moiety is $C_{6-12}$.

"AUC" is the area under a curve representing the concentrati on of a compound or metabolite thereof in a biological fluid in a patient as a function of time following administration of the compound to the patient. In certain embodiments, the compound can be a prodrug and the metabolite can be a drug. Examples of biological fluids include plasma and blood. The AUC may be determined by measuring the concentration of a compound or metabolite thereof in a biological fluid such as the plasma or blood using methods such as liquid chromatography-tandem mass spectrometry (LC/MS/MS), at various time intervals, and calculating the area under the plasma concentration-versus-time curve. Suitable methods for calculating the AUC from a drug concentration-versus-time curve are well known in the art. As relevant to the invention, an AUC for a drug or metabolite thereof may be determined by measuring over time the concentration of the drug in the plasma, blood or other biological fluid or tissue of a patient following administration of a corresponding compound of the invention to the patient.

"Bioavailability" refers to the rate and amount of a drug that reaches the systemic circulation of a patient following administration of the drug or prodrug thereof to the patient and can be determined by evaluating, for example, the plasma or blood concentration-versus-time profile for a drug. Parameters useful in characterizing a plasma or blood concentration-versus-time curve include the area under the curve (AUC), the time to,maximum concentration ($T_{max}$), and the maximum drug concentration ($C_{max}$), where $C_{max}$ is the maximum concentration of a drug in the plasma or blood of a patient following administration of a dose of the drug or form of drug to the patient, and $T_{max}$ is the time to the maximum concentration ($C_{max}$) of a drug in the plasma or blood of a patient following administration of a dose of the drug or form of drug to the patient.

"$C_{max}$" is the maximum concentration of a drug in the plasma or blood of a patient following administration of a dose of the drug or prodrug to the patient.

"$T_{max}$" is the time to the maximum (peak) concentration ($C_{max}$) of a drug in the plasma or blood of a patient following administration of a dose of the drug or prodrug to the patient.

"Compounds of the invention" or "compound of the invention", include any specific compounds within these formulae. Compounds may be identified either by their chemical structure and/or chemical name. When the chemical structure and chemical name are conflicting, the chemical structure is determinative of the identity of the compound. The compounds described herein may comprise one or more chiral centers and/or double bonds and therefore may exist as stereoisomers such as double-bond isomers (i.e., geometric isomers), enantiomers or diastereomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomericaily pure or diastereomerically pure) and enantiomeric and stereoisomeric mixtures. Enantiomeric and stereoisomeric mixtures may be resolved into their component enantiomers or stereoisomers using separation techniques or chiral synthesis techniques well known to the skilled artisan. Compounds of the invention are also referred to as "prodrugs of creatine" or "prodrugs of the invention."

Compounds of invention include, but are not limited to, stereoisomers or optical isomers of compounds of the invention, racemates thereof, and other mixtures thereof. In such embodiments, the single enantiomers or diastereomers, i.e., optically active forms, can be obtained by asymmetric synthesis or by resolution of the racemates; Resolution of the racemates may be accomplished, for example, by conventional methods such as crystallization in the presence of a resolving agent or chromatography, using, for example a chiral high-pressure liquid chromatography (HPLC) column. In addition, compounds of the invention include Z- and E-forms (or cis- and trans-forms) of compounds with double bonds. In embodiments in which compounds of the invention exist in various tautomeric forms, the compounds include all tautomeric forms of the compound.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposable mirror images of one another.

Compounds of the invention may also exist in several tautomeric, forms, and the depiction herein of one tautomer is for convenience only, and is also understood to encompass other tautomers of the form shown. Accordingly, the chemical structures depicted herein encompass all possible tautomeric forms of the illustrated compounds. The term "tautomer" as used herein refers to isomers that change into one another with great ease so that they can exist together in equilibrium. For example, ketone and enol are two tautomeric forms of one compound. In another example, a substituted 1,2,4-triazole derivative may exist in at least three tautomeric forms as shown below:

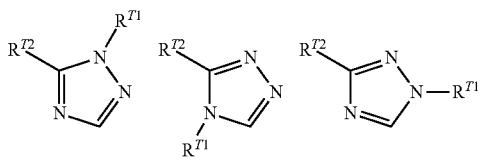

$R^{T1}$ is H or optionally substituted alkyl,
$R^{T2}$ is an optionally substituted aryl.

Compounds of the invention also include isotopically labeled compounds where one or more atoms have an atomic mass different from the atomic mass conventionally found in nature. Examples of isotopes that may be incorporated into the compounds disclosed herein include, but are not limited to, $^2$H, $^3$H, $^{11}$C, $^{13}$C, $^{14}$C, $^{15}$N, $^{18}$O, $^{17}$O, etc. Compounds may exist in unsolvated forms as well as solvated forms, including hydrated forms and as N-oxides. In general, compounds may be hydrated, solvated or N-oxides. Certain compounds may exist in multiple crystalline or amorphous forms. Compounds of the invention include pharmaceutically acceptable salts thereof or pharmaceutically acceptable solvates of the free acid form of any of the foregoing, as well as crystalline forms of any of the foregoing.

"Creatine kinase system" includes, but is not limited to the creatine transporter, creatine, creatine kinase, creatine phosphate, and the intracellular energy transport of creatine, creatine kinase, and/or creatine phosphate. The creatine kinase system includes mitochondrial and cytoplasmic creatine kinase systems. Affecting the creatine kinase system refers to the transport, synthesis, metabolism, translocation, and the like, of the compounds and proteins comprising the creatine kinase system.

"Cycloalkyl" by itself or as part of another substituent refers to a saturated or partially unsaturated cyclic alkyl radical. Where a specific level of saturation is intended, the nomenclature "cycloalkanyl" or "cycloalkenyl" is used. Examples of cycloalkyl groups include, but are not limited to, groups derived from cyclopropane, cyclobutane, cyclopentane, cyclohexane, and the like. In certain embodiments, a cycloalkyl group is $C_{3-15}$ cycloalkyl, $C_{5-12}$ cycloalkyl, and in certain.embodiments, $C_{3-7}$ cycloalkyl.

"Cycloalkylalkyl" by itself or as part of another substituent refers to an acyclic alkyl radical in which one of the hydrogen atoms bonded to a carbon atom, typically a terminal or sp$^3$ carbon atom, is replaced with a cycloalkyl group. Where specific alkyl moieties are intended, the nomenclature cycloalkylalkanyl, cycloalkylalkenyl or cycloalkylalkynyl is used. In certain embodiments, a cycloalkylalkyl group is $C_{7-30}$ cycloalkylalkyl, e.g., the alkanyl, alkenyl or alkynyl moiety of the cycloalkylalkyl group is $C_{1-10}$ and the cycloalkyl moiety is $C_{6-20}$, and in certain embodiments, a cycloalkylalkyl group is $C_{7-20}$ cycloalkylalkyl, e.g., the alkanyl, alkenyl or alkynyl moiety of the cycloalkylalkyl group is $C_{1-8}$ and the cycloalkyl moiety is $C_{4-20}$ or $C_{6-12}$.

"Disease" refers to a disease, disorder, condition, symptom or indication.

"Halogen" refers to a fluoro, chloro, bromo or iodo group.

"Heteroalkyl" by itself or as part of another substituent refer to an alkyl group in which one or more of the carbon atoms (and any associated hydrogen atoms) are each independently replaced with the same or different heteroatomic groups. Examples of heteroatomic groups include, but are not limited to, —O—, —S—, —O—O—, —S—S—, —O—S—, —NR$^{57}$R$^{58}$—,═N—N═—N═N—, —N═N—NR$^{59}$R$^{60}$, —PR$^{61}$—, —P(O)$_2$—, —POR$^{62}$—, —O—P(O)$_2$—, —SO—, —SO$_2$—, —SnR$^{63}$R$^{64}$—, and the like, where R$^{57}$, R$^{58}$, R$^{59}$, R$^{60}$, R$^{61}$, R$^{62}$, R$^{63}$, and R$^{64}$ are each independently chosen from hydrogen, Cmz alkyl, substituted $C_{1-12}$ alkyl, $C_{6-12}$ aryl, substituted $C_{6-12}$ aryl, $C_{7-18}$ arylalkyl, substituted $C_{7-18}$ arylalkyl, $C_{3-7}$ cycloalkyl, substituted $C_{3-7}$ cycloalkyl, $C_{3-7}$ heterocycloalkyl, substituted $C_{3-7}$ heterocycloalkyl, $C_{1-12}$ heteroalkyl, substituted $C_{1-12}$ heteroalkyl, $C_{6-12}$ heteroaryl; substituted $C_{6-12}$ heteroaryl, $C_{7-18}$ heteroarylalkyl or substituted $C_{7-18}$ heteroarylalkyl. Where a specific level of saturation is intended, the nomenclature "heteroalkanyl", "heteroalkenyl," or R$^{60}$, R$^{61}$, R$^{62}$, R$^{63}$, and R$^{64}$ "heteroalkynyl" is used. In certain embodiments, R$^{57}$, R$^{58}$, R$^{59}$, are each independently chosen from hydrogen and $C_{1-3}$ alkyl.

"Heteroaryl" by itself or as part of another substituent refers to a monovalent heteroaromatic radical derived by the removal of one hydrogen atom from a single atom of a parent heteroaromatic ring system. Heteroaryl encompasses multiple ring systems having at least one heteroaromatic ring fused to at least one other ring, which can be aromatic or non-aromatic. Heteroaryl encompasses 5- to 7-membered aromatic, monocyclic rings containing one or more, for example, from 1 to 4 or in certain embodiments, from 1 to 3, heteroatoms chosen from N, O, and S, with the remaining ring atoms being carbon; and bicyclic heterocycloalkyl rings containing one or more, for example, from 1 to 4 or in certain embodiments, from 1 to 3, heteroatoms chosen from N, O, and S, with the remaining ring atoms being carbon and wherein at least one heteroatom is present in an aromatic ring. For example, heteroaryl includes a 5- to 7-membered heteroaromatic ring fused to a 5- to 7-membered cycloalkyl ring. For such fused, bicyclic heteroaryl ring systems wherein only one of the rings contains one or more heteroatoms, the point of attachment may be at the heteroaromatic ring or the cycloalkyl ring. In certain embodiments, when the total number of N, S, and O atoms in the heteroaryl group exceeds one, the heteroatoms are not adjacent to one another. In certain embodiments, the total number of N, S, and O atoms in the heteroaryl group is not more than two; In certain embodiments, the total number of N, S, and O atoms in the aromatic heterocycle is hot more than one. Heteroaryl does not encompass or overlap with aryl as defined herein.

Examples of heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, liaphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In certain embodiments, a heteroaryl group is from 5- to 20-membered heteroaryl, in certain embodiments from 5- to 10-membered heteroaryl, and in certain embodiments from 6- to 8-heteroaryl. In certain embodiments heteroaryl groups are those derived from thiophene, pyrrole, benzothiophene, benzofuran, indole, pyridine, quinoline, imidazole, oxazole or pyrazine.

"Heteroarylalkyl" by itself or as part of another substituent refers to an acyclic alkyl radical in which one of the hydrogen atoms bonded to a carbon atom, is replaced with a heteroaryl group. Typically a terminal or $sp^3$ carbon atom is the atom replaced with the heteroaryl group. Where specific alkyl moieties are intended, the nomenclature "heteroarylalkanyl," "heteroarylalkenyl," and "heterorylalkynyl" is used. In certain embodiments, a heteroarylalkyl group is a 6- to 30-membered heteroarylalkyl, e.g., the alkanyl, alkenyl or alkynyl moiety of the heteroarylalkyl is 1- to 10-membered and the heteroaryl moiety is a 5- to 20-membered heteroaryl, and in certain embodiments, 6- to 20-membered heteroarylalkyl, e.g., the alkanyl, alkenyl or alkynyl moiety of the heteroarylalkyl is 1- to 8-membered and the heteroaryl moiety is a 5-to 12-membered heteroaryl.

"Heterocycloalkyl" by itself or as part of another substituent refers to a partially saturated or unsaturated cyclic alkyl radical in which one or more carbon atoms (and any associated hydrogen atoms) are each independently replaced with the same or different heteroatom. Examples of heteroatoms to replace the carbon atom(s) include, but are not limited to, N, P, O, S, Si, etc. Where a specific level of saturation is intended, the nomenclature "heterocycloalkanyl" or "heterocycloalkenyl" is used. Examples of heterocycloalkyl groups include, but are not limited to, groups derived from epoxides, azirines, thiiranes, imidazoline, morpholine, piperazine, piperidine, pyrazolidine, pyrrolidine, quinuclidine, and the like.

"Heterocycloalkylalkyl" by itself or as part of another substituent refers to an acyclic alkyl radical in which one of the hydrogen atoms bonded to a carbon atom, typically a terminal or $sp^3$ carbon atom, is replaced with a heterocycloalkyl group. Where specific alkyl moieties are intended, the nomenclature heterocycloalkylalkanyl, heterocycloalkylalkenyl or heterocycloalkylalkynyl is used. In certain embodiments, a heterocycloalkylalkyl group is a 6- to 30-membered heterocycloalkylalkyl e.g., the alkanyl, alkenyl or alkynyl moiety of the heterocycloalkylalkyl is 1- to 10-membered and the heterocycloalkyl moiety is a 5- to 20-membered heterocycloalkyl, and in certain embodiments, 6- to 20-membered heterocycloalkylalkyl, e.g., the alkanyl, alkenyl or alkynyl moiety of the heterocycloalkylalkyl is 1- to 8-membered and the heterocycloalkyl moiety is a 5- to 12-membered heterocycloalkyl.

"Leaving group" refers to an atom or a group capable of being displaced by a nucleophile and includes halogen, such as chloro, bromo, fluoro, and iodo, alkoxycarbonyl (e.g., acetoxy), aryloxycarbonyl, mesyloxy, tosyloxy, trifluoromethanesulfonyloxy, aryloxy (e.g., 2,4-dinitrophenoxy), methoxy, N,O-dimethylhydroxylamino, and the like.

"Parent aromatic ring system" refers to an unsaturated cyclic or polycyclic ring system having a conjugated π electron system. Included within the definition of "parent aromatic ring system" are fused ring systems in which one or more of the rings are aromatic and one or more of the rings are saturated or unsaturated, such as, for example, fluorene, indane, indene, phenalene, etc. Examples of parent aromatic ring systems include, but are not limited to, aceanthrylene, acenaphthylene, acephenanthiylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like.

"Parent heteroaromatic ring system" refers to an aromatic ring system in which one or more carbon atoms (and any associated hydrogen atoms) are each independently replaced with the same or different heteroatom. Examples of heteroatoms to replace the carbon atoms include, but are not limited to, N, P, O, S, and Si, etc. Specifically included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Examples of parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Patient" refers to animals, preferably mammals, most preferably humans, and includes males and females, and children and adults.

"Pharmaceutical composition" refers to at least one compound of the invention and at least one pharmaceutically acceptable vehicle, with which the at least one compound of the invention is administered to a patient, contacted with a tissue or organ or contacted with a cell. "Pharmaceutically acceptable" refers to approved or approvable by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound, which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butyl acetic acid, lauryl sulfuric acid, gluconic acid, glutamic acid, hydroxynaphthoic acid, salicylic acid, stearic acid, muconic acid, and the like; and (2) salts formed when an acidic proton present in the parent compound is replaced by a metal ion, e.g., an alkali metal ion, an alkaline earth ion or an aluminum ion; or coordinates with an organic base such as ethanolamine, diethanolamine, triethanolamine, N-methylglucamine, and the like. In certain embodiments, a pharmaceutically acceptable salt is the hydrochloride salt.

"Pharmaceutically acceptable vehicle" refers to a pharmaceutically acceptable diluent, a pharmaceutically acceptable adjuvant, a pharmaceutically acceptable excipient, a pharmaceutically acceptable carrier or a combination of any of the foregoing with which a compound of the invention may be administered to a patient and which does not destroy the pharmacological activity thereof and which is non-toxic when administered in doses sufficient to provide a therapeutically effective amount of the compound.

"Prodrug" refers to a derivative of a drug molecule that requires a transformation within the body to release the active drug. Prodrugs are frequently, although not necessarily, pharmacologically inactive until converted to the parent drug. Compounds of Formulae (I), (III), (VI), (VII), and any subgenera or species thereof, are prodrugs of creatine that can be metabolized within a patient's body to release creatine.

"Promoiety" refers to a group bonded to a drug, typically to a functional group of the drug, via bond(s) that are cleavable under specified conditions of use. The bond(s) between the drug and promoiety may be cleaved by enzymatic or non-enzymatic means. Under the conditions of use, for example following administration to a patient, the bond(s) between the drug and promoiety may be cleaved to release the parent drug. The cleavage of the promoiety may proceed spontaneously, such as via a hydrolysis reaction or it may be catalyzed or induced by another agent, such as by an enzyme, by light, by acid or by a change of or exposure to a physical or environmental parameter, such as a change of temperature, pH, etc. The agent may be endogenous to the conditions of use, such as an enzyme present in the systemic circulation of a patient to which the prodrug is administered or the acidic conditions of the stomach or the agent may be supplied exogenously.

"Protecting group" refers to a grouping of atoms, which when attached to a reactive group in a molecule masks, reduces or prevents that reactivity. Examples of protecting groups can be found in Wuts and Greene, "Protective Groups in Organic Synthesis," John Wiley & Sons, 4th ed. 2006; Harrison etal, "Compendium of Organic Synthetic Methods," Vols. 1-11, John Wiley & Sons 1971-2003; Larock "Comprehensive Organic Transformations," John Wiley & Sons, 2nd ed. 2000; and Paquette, "Encyclopedia of Reagents for Organic Synthesis;" John Wiley & Sons, 11th ed. 2003. Examples of amino protecting groups include, but are not limited to, formyl, acetyl, trifluoroacetyl, benzyl, benzyloxycarbonyl (CBZ), tert-butoxycarbonyl (Boc), trimethylsilyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like. Examples of hydroxy protecting groups include, but are not limited to, those in which the hydroxy group is either acylated or alkylated such as benzyl, and trityl ethers as well as alkyl ethers, tetrahydropyranyl ethers, trialkylsilyl ethers, and allyl ethers.

"Solvate" refers to a molecular complex of a compound with one or more solvent molecules in a stoichiometric or non-stoichiometric amount. Such solvent molecules are those commonly used in the pharmaceutical art, which are known to be innocuous to recipient, e.g., water, ethanol, and the like. A molecular complex of a compound or moiety of a compound and a solvent can be stabilized by non-covalent intra-molecular forces such as, for example, electrostatic forces, van der Waals forces or hydrogen bonds. The term "hydrate" refers to a complex in which the one or more solvent molecules are water including monohydrates and hemi-hydrates.

"Substantially one diastereomer" refers to a compound containing two or more stereogenic centers such that the diastereomeric excess (d.e.) of the compound is greater than or about at least 90%. In certain embodiments, the d.e. is, for example, greater than or at least about 91%, about 92%, about 93%, about 94%, about 95%, about 96%, about 97%, about 98% or about 99%.

"Substituted" refers to a group in which one or more hydrogen atoms are each independently replaced with the same or different substituent(s). Examples of substituents include, but are not limited to, -M, $-R^{70}$, $-O^-$, $=O$, $-OR^{70}$, $-SR^{70}$, $-S^-$, $=S$, $-NR^{70}R^{71}$, $=NR^{70}$, $-CF_3$, $-CN$, $-OCN$, $-SCN$, $-NO$, $-NO_2$, $=N_2$, $-N3$, $-S(O)_2O^-$, $-S(O)_2OH$, $-S(O)_2R^{70}$, $-OS(O_2)O^-$, $-OS(O)_2R^{70}$, $-P(O)(O^-)_2$, $-P(O)(OR^{70})(O^-)$, $-OP(O)(OR^{70})(OR^{71})$, $-C(O)R^{70}$, $-C(S)R^{70}$, $-C(O)OR^{70}$, $-C(O)NR^{70}R^{71}$, $-C(O)O-$, $-C(S)OR^{70}$, $-NR^{72}C(O)NR^{70}R^{71}$, $-NR^{72}C(S)NR^{70}R^{71}$, $-NR^{72}C(NR^{73})NR^{70}R^{71}$, and $-C(NR^{72})NR^{70}R^{71}$ where M is independently a halogen; $R^{70}$, $R^{71}$, $R^{72}$, and $R^{73}$ are each independently chosen from hydrogen, alkyl, alkoxy, cycloalkyl, heterocycloalkyl, aryl, and heteroaryl or $R^{70}$ and $R^{71}$ together with the nitrogen atom to which they are bonded form a ring chosen from a heterocycloalkyl ring. In certain embodiments, $R^{70}$, $R^{71}$, $R^{72}$, and $R^{73}$ are each independently chosen from hydrogen, $C_{1-6}$ alkyl, $C_{1-6}$ alkoxy, $C_{3-12}$ cycloalkyl, $C_{3-12}$ heterocycloalkyl, $C_{6-12}$ aryl, and $C_{6-12}$ heteroaryl. In certain embodiments, each substituent is independently selected from halogen, $-OH$, $-CN$, $-CF_3$, $=O$, $-NO_2$, $C_{1-3}$ alkoxy, $C_{1-3}$ alkyl, $-COOR^{80}$ wherein $R^{80}$ is selected from hydrogen, $C_{1-3}$ alkyl and $(NR^{74})_2$ wherein each $R^{74}$ is independently hydrogen or $C_{1-3}$ alkyl.

In certain embodiments, substituted aiyl and substituted heteroaryl include one or more of the following substitute groups: F, Cl, Br, $C_{1-3}$ alkyl, substituted alkyl, $C_{1-3}$ alkoxy, $-S(O)_2NR^{50}R^{51}$, $-NR^{50}R^{51}$, $-CF_3$, $-OCF_3$, $-CN$, $-NR^{50}S(O)_2R^{51}$, $-NR^{50}C(O)R^{51}$, $C_{5-10}$ aryl, substituted $C_{5-10}$ aryl, $C_{5-10}$ heteroaryl, substituted $C_{5-10}$ heteroaryl, $-C(O)OR^{50}$, $-NO_2$, $-C(O)R^{50}$, $-C(O)NR^{50}R^{51}$, $-OCHF_2$, $C_{1-3}$ acyl, $-SR^{50}$, $-S(O)_2OH$, $-S(O)_2R^{50}$, $-S(O)R^{50}$, $-C(S)R^{50}$, $-C(O)O^-$, $-C(S)OR^{50}$, $-NR^{50}C(O)NR^{51}R^{52}$, $-NR^{50}C(S)NR^{51}R^{52}$, and $-C(NR^{50})NR^{51}R^{52}$, $C_{3-8}$ cycloalkyl, and substituted $C_{3-8}$ cycloalkyl, wherein $R^{50}$, $R^{51}$, and $R^{52}$ are each independently selected from hydrogen and $C_{1-4}$ alkyl.

In certain embodiments, a substituent group can be selected from halogen, $-NO_2$, $-OH$, $-COOH$, $-NH_2$, $-CN$, $-CF_3$, $-OCF_3$, $C_{1-8}$ alkyl, substituted $C_{1-8}$ alkyl, $C_{1-8}$ alkoxy, and substituted $C_{1-8}$ alkoxy, wherein the each substituent of the substituted $C_{1-8}$ alkyl and $C_{1-8}$ alkoxy is independently selected from halogen, $-NO_2$, $-OH$, $-COOH$, $-NH_2$, $-CN$, $-CF_3$, $-OCF_3$.

In certain embodiments, each substituent is independently selected from halogen, $-OH$, $-CN$, $-CF_3$, $=O$, $-NO_2$, $C_{1-3}$ alkoxy, $C_{1-3}$ alkyl, $-COOR^{80}$ wherein $R^{80}$ is selected from hydrogen, $C_{1-3}$ alkyl and $(NR^{74})_2$ wherein each $R^{74}$ is independently hydrogen or $C_{1-3}$ alkyl.

"Therapeutically effective amount" refers to the amount of a compound that, when administered to a subject for treating a disease or disorder or at least one of the clinical symptoms of a disease or disorder, is sufficient to affect such treatment of the disease, disorder or symptom. The "therapeutically effective amount" can vary depending, for example, on the compound, the disease, disorder, and/or symptoms of the disease or disorder, severity of the disease, disorder, and/or symptoms of the disease or disorder, the age, weight, and/or health of the patient to be treated, and the judgment of the prescribing physician. An appropriate amount in any given instance can be readily ascertained by those skilled in the art or capable of determination by routine experimentation.

"Therapeutically effective dose" refers to a dose that provides effective treatment of a disease or disorder in a patient A therapeutically effective dose may vary from compound to compound, and from patient to patient, and may depend upon factors such as the condition of the patient and the route of delivery. A therapeutically effective dose may be determined in accordance with routine pharmacological procedures known to those skilled in the art.

"Treating" or "treatment" of any disease or disorder refers to arresting or ameliorating a disease, disorder or at least one of the clinical symptoms of a disease or disorder, reducing the risk of acquiring a disease, disorder or at least one of the clinical symptoms of a disease or disorder, reducing the development of a disease, disorder or at least one of the clinical symptoms of the disease or disorder or reducing the risk of developing a disease or disorder or at least one of the clinical symptoms of a disease or disorder. "Treating" or "treatment" also refers to inhibiting the disease or disorder, either physically, (e.g., stabilization of a discernible symptom), physiologically, (e.g., stabilization of a physical parameter) or both, and to inhibiting at least one physical parameter that may or may not be discernible to the patient. In certain embodiments, "treating" or "treatment" refers to delaying the onset of the disease or disorder or at least one or more symptoms thereof in a patient which may be exposed to or predisposed to a disease or disorder even though that patient does not yet experience or display symptoms of the disease or disorder.

Reference is now made in detail to certain embodiments of compounds, compositions, and methods. The disclosed embodiments are not intended to be limiting of the claims. To the contrary, the claims are intended to cover all alternatives, modifications, and equivalents.

Creatine Prodrugs

In certain embodiments, a creatine prodrug is a compound of Formula (I) or a pharmaceutically acceptable salt, solvate, tautomer or stereoisomer thereof:
wherein the compound of Formula (I) is

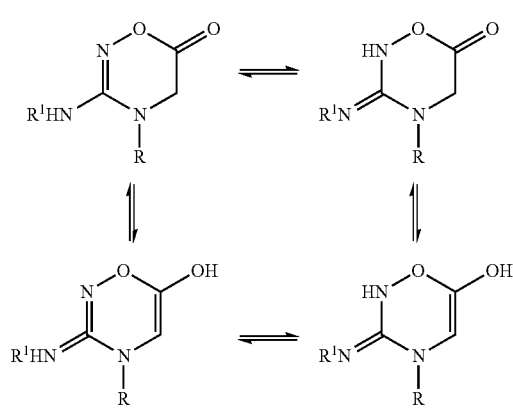

(I)

wherein:
R is —CH$_3$ or —CD$_3$;
R$^1$ is hydrogen, —OR$^2$, —C(O)OR$^2$, —C(O)R$^2$,

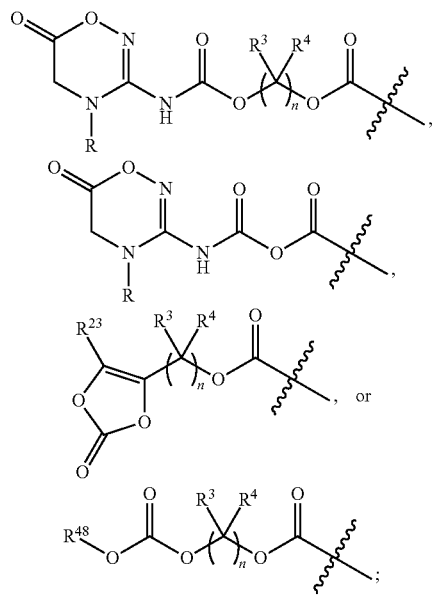

n is an integer from 1 to 2;
each R$^2$ is independently hydrogen, C$_{1-12}$ alkyl, substituted C$_{1-12}$ alkyl, C$_{1-12}$ heteroalkyl, substituted C$_{1-12}$ heteroalkyl, C$_{3-12}$ cycloalkyl, substituted C$_{3-12}$ cycloalkyl, C$_{4-20}$ cycloalkylalkyl, substituted C$_{4-20}$ cycloalkylalkyl, C$_{4-20}$ heterocycloalkylalkyl, substituted C$_{4-20}$ heterocycloalkylalkyl, C$_{5-12}$ aryl, substituted C$_{5-12}$ aryl, C$_{5-12}$ heteroaryl, substituted C$_{5-12}$ heteroaryl, C$_{6-20}$ arylalkyl, substituted C$_{6-20}$ arylalkyl, C$_{6-20}$ heteroarylalkyl or substituted C$_{6-20}$ heteroarylalkyl;
each R$^3$ and R$^4$ is independently hydrogen, C$_{1-12}$ alkyl or substituted C$_{1-12}$ alkyl;
R$^{23}$ is hydrogen, C$_{1-12}$ alkyl, substituted C$_{1-12}$ alkyl, C$_{5-12}$ cycloalkyl, substituted C$_{5-12}$ cycloalkyl, C$_{5-12}$ aryl, and C$_{5-12}$ substituted aryl, —C(O)—OR$^{22}$ or —C(O)—R$^{22}$,
R$^{22}$ is C$_{1-12}$ alkyl, substituted C$_{1-12}$ alkyl, C$_{1-12}$ heteroalkyl, substituted C$_{1-12}$ heteroalkyl, C$_{3-12}$ cycloalkyl, substituted C$_{3-12}$ cycloalkyl, C$_{4-20}$ cycloalkylalkyl, substituted C$_{4-20}$ cycloalkylalkyl, C$_{4-20}$ heterocycloalkylalkyl, substituted C$_{4-20}$ heterocycloalkylalkyl, C$_{5-12}$ aryl, substituted C$_{5-12}$ aryl, C$_{5-12}$ heteroaryl, substituted C$_{5-12}$ heteroaryl, C$_{6-20}$ arylalkyl, substituted C$_{6-20}$ arylalkyl, C$_{6-20}$ heteroarylalkyl or substituted C$_{6-20}$ heteroarylalkyl; and
R$^{48}$ is C$_{1-12}$ alkyl or substituted C$_{1-12}$ alkyl.

In certain embodiments of a compound of Formula (I), n is the integer 1.

In certain embodiments of a compound of Formula (I), n is the integer 2.

In certain embodiments of a compound of Formula (I) each R$^2$ and R$^{22}$ is independently hydrogen, methyl, ethyl, n-propyl, isopropyl, butyl, isobutyl, sec-butyl, tert-butyl, n-pentyl, isopentyl, sec-pentyl, neopentyl, dodecyl, 1,1-dimethoxyethyl, 1,1-diethoxyethyl, phenyl, 4-methoxyphenyl, benzyl, phenethyl, styryl, cyclopropyl, cyclobutyl, cyclopentyl, cyclohexyl, 2-pyridyl, 3-pyridyl or 4-pyridyl.

In certain embodiments of a compound of Formula (I), each R$^2$ and R$^{22}$ is independently hydrogen, methyl, ethyl, n-propyl, isopropyl, n-butyl, isobutyl, sec-butyl, tert-butyl, n-pentyl, isopentyl, sec-pentyl, neopentyl, dodecyl, 1,1-diethoxyethyl, phenyl, cyclohexyl or 3-pyridyl.

In certain embodiments of a compound of Formula (I), each $R^2$ and $R^{22}$ is independently independently hydrogen, methyl, ethyl, n-propyl, isopropyl, dodecyl, tert-butyl, phenyl or cyclohexyl.

In certain embodiments of a compound of Formula (I), each $R^2$ and $R^{22}$ is independently ethyl, isopropyl or dodecyl.

In certain embodiments of a compound of Formula (I), $R^3$ and $R^4$ each independently is hydrogen.

In certain embodiments of a compound of Formula (I), $R^{23}$ is hydrogen, methyl, ethyl, n-propyl, isopropyl, tert-butyl, dodecyl, phenyl or cyclohexyl.

In certain embodiments of a compound of Formula (I), $R^{23}$ is methyl.

In certain embodiments of a compound of Formula (I), each substituent group is independently halogen, $-NO_2$, $-OH$, $-NH_2$, $-CN$, $-CF_3$, $-OCF_3$, $=O$, $C_{1-12}$ alkyl, substituted $C_{1-12}$ alkyl, $C_{1-12}$ alkoxy or substituted $C_{1-12}$ alkoxy, $-COOR^{10'}$ wherein $R^{10'}$ is hydrogen, $C_{1-3}$ alkyl or $-(NR^{11'})_2$ wherein each $R^{11'}$ is independently hydrogen of $C_{1-3}$ alkyl.

In some embodiment, the compound of Formula (I) is a compound of Formula (X), Formula (XI), Formula (XII), Formula (XIII), Formula (XIV), Formula (XV), Formula (XVa) or Formula (XVb) or a pharmaceutically acceptable salt, solvate, tautomer or stereoisomer thereof;

wherein the compound of Formula (X) is:

(X)

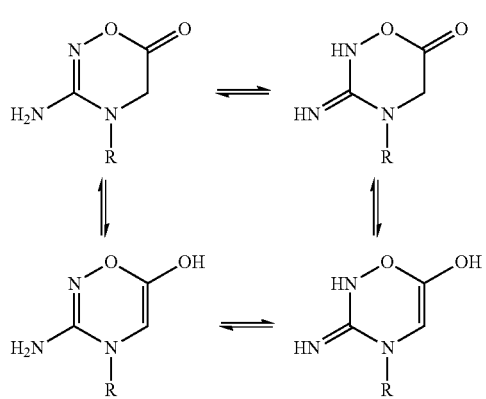

wherein R is $-CH_3$ or $-CD_3$;
wherein the compound of Formula (XI) is:

(XI)

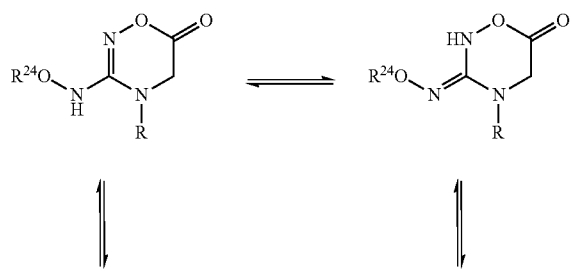

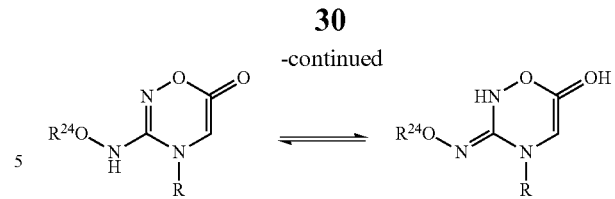

wherein R is $-CH_3$ or $-CD_3$; and
$R^{24}$ is hydrogen, methyl, ethyl, n-propyl, isopropyl, tert-butyl, dodecyl, phenyl or cyclohexyl;
wherein the compound of Formula (XII) is:

(XII)

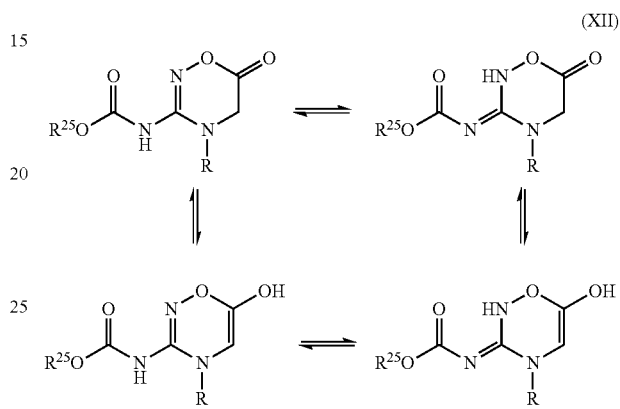

wherein R is $-CH_3$ or $-CD_3$; and
$R^{25}$ is hydrogen, methyl, ethyl, n-propyl, isopropyl, tert-butyl, dodecyl, phenyl or cyclohexyl;
wherein the compound of Formula (XIII) is:

(XIII)

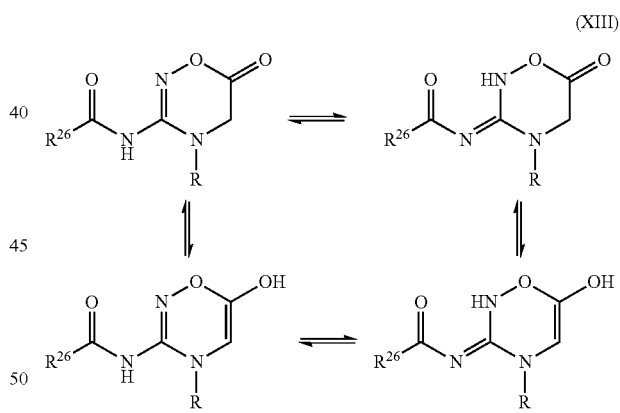

wherein R is $-CH_3$ or $-CD_3$; and
$R^{26}$ is hydrogen, methyl, ethyl, n-propyl, isopropyl, tert-butyl, dodecyl, phenyl or cyclohexyl;
wherein the compound of Formula (XIV) is:

(XIV)

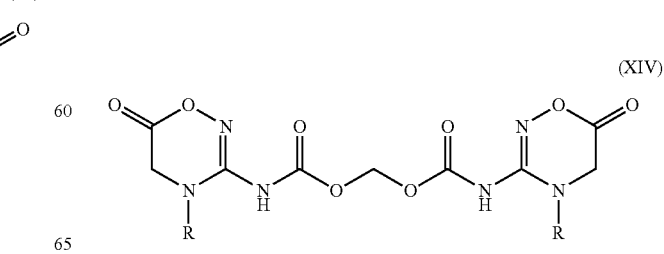

wherein R is $-CH_3$ or $-CD_3$;

wherein the compound of Formula (XV) is:

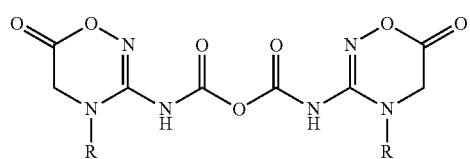

(XV)

wherein R is —CH$_3$ or —CD$_3$;
wherein the compound of Formula (XVa) is:

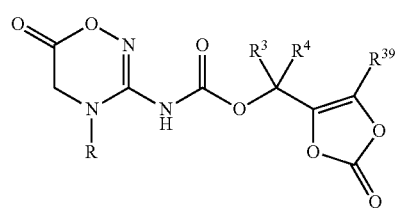 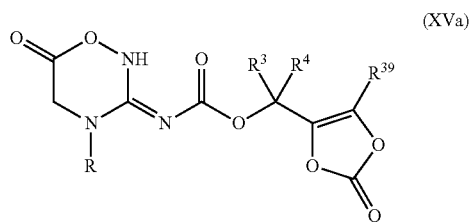

(XVa)

wherein R is —CH$_3$ or —CD$_3$;
R$^{39}$ is hydrogen, methyl, ethyl, n-propyl, isopropyl, tert-butyl, dodecyl, phenyl or cyclohexyl, and
R$^3$ and R$^4$ is independently hydrogen, C$_{1-12}$ alkyl or substituted C$_{1-12}$ alkyl;
wherein the compound of Formula (XVb) is:

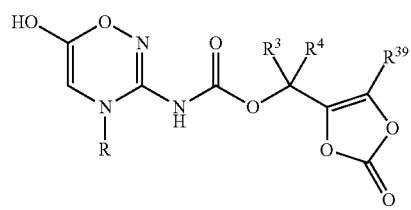 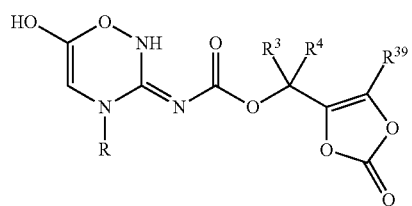

wherein R is —CH$_3$ or —CD$_3$;
R$^3$ and R$^4$ are each independently hydrogen, C$_{1-12}$ alkyl or substituted C$_{1-12}$ alkyl; and
R$^{53}$ is C$_{1-12}$ alkyl or substituted C$_{1-12}$ alkyl.

In certain embodiments in the compounds of Formula (XI), (XII) and (XIII), each R$^{24}$, R$^{25}$ and R$^{26}$ is independently ethyl, isopropyl or dodecyl.

In certain embodiments in the compounds of Formula (XVa), R$^{39}$ is methyl, ethyl, n-propyl, isopropyl, tert-butyl, dodecyl, phenyl or cyclohexyl.

In certain embodiments in the compounds of Formula (XVa), R$^{39}$ is methyl,

In certain embodiments in the compounds of Formula (XVa) or (XVb), R$^3$ and R$^4$ are each hydrogen.

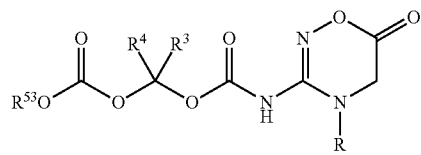 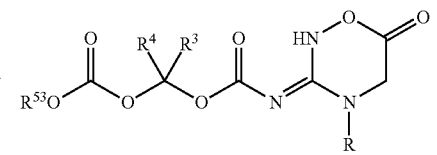

(XVb)

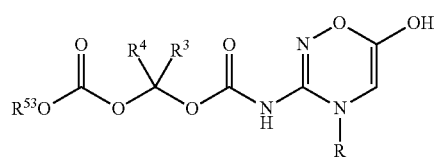 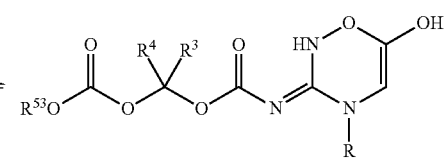

In certain embodiments in the compounds of Formula (XVb), R$^{53}$ is methyl, ethyl, n-propyl, isopropyl or tert-butyl.

In certain embodiments a creatine prodrug is a compound of Formula (III) or a pharmaceutically acceptable salt, solvate, tautomer or stereoisomer thereof:

wherein the compound of Formula (III) is:

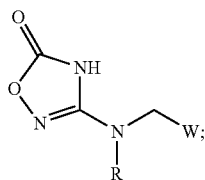

(III)

wherein:
W is —CH$_2$OH or —C(O)OR$^7$;
R is —CH$_3$ or —CD$_3$;
R$^7$ is hydrogen, C$_{1-12}$ alkyl, substituted C$_{1-12}$ alkyl, C$_{1-12}$ heteroalkyl, substituted C$_{1-12}$ heteroalkyl, C$_{3-12}$ cycloalkyl, substituted C$_{3-12}$ cycloalkyl, C$_{4-20}$ cycloalkylalkyl, substituted C$_{4-20}$ cycloalkylalkyl, C$_{4-20}$ heterocycloalkylalkyl, substituted C$_{4-20}$ heterocycloalkylalkyl, C$_{5-12}$ aryl, substituted C$_{5-12}$ aiyl, C$_{5-12}$ heteroaryl, substituted C$_{5-12}$ heteroaryl, C$_{6-20}$ arylalkyl, substituted C$_{6-20}$ arylalkyl, C$_{6-20}$ heteroarylalkyl, substituted C$_{6-20}$ heteroarylalkyl, —C(O)R$^5$, —C(O)OR$^5$, —C(O)(NR$^3$R$^4$), —C(R$^3$R$^4$)—C(O)OR$^{22}$, —C(R$^3$R$^4$)—(O)C(O) R$^{22}$, —C(R$^3$R$^4$)—(O)C(O)—OR$^{22}$,

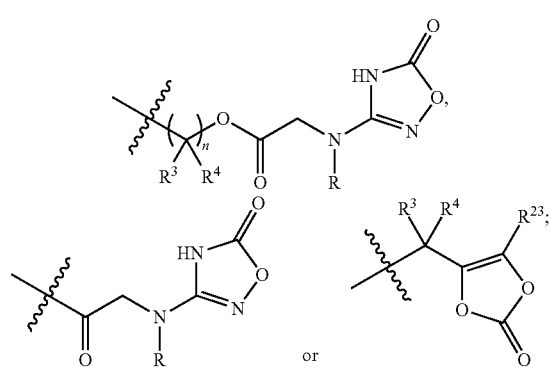

n is an integer from 1 to 2;
each R$^3$ and R$^4$ is independently hydrogen, C$_{1-12}$ alkyl or substituted C$_{1-12}$ alkyl; and
R$^5$ is hydrogen, C$_{1-12}$ alkyl, substituted C$_{1-12}$ alkyl, C$_{1-12}$ heteroalkyl, substituted C$_{1-12}$ heteroalkyl, C$_{3-12}$ cycloalkyl, substituted C$_{3-12}$ cycloalkyl, C$_{4-20}$ cycloalkylalkyl, substituted C$_{4-20}$ cycloalkylalkyl, C$_{4-20}$ heterocycloalkylalkyl, substituted C$_{4-20}$ heterocycloalkylalkyl, C$_{5-12}$ aryl, substituted C$_{5-12}$ aryl, C$_{5-12}$ heteroaryl, substituted C$_{5-12}$ heteroaryl, C$_{6-20}$ arylalkyl, substituted C$_{6-20}$ arylalkyl, C$_{6-20}$ heteroarylalkyl or substituted C$_{6-20}$ heteroarylalkyl;
R$^{23}$ is hydrogen, C$_{1-12}$ alkyl, substituted C$_{1-12}$ alkyl, C$_{5-12}$ cycloalkyl, substituted C$_{5-12}$ cycloalkyl, C$_{5-12}$ aryl, and C$_{5-12}$ substituted aryl, —C(O)—OR$^{22}$ or —C(O)—R$^{22}$; and
R$^{22}$ is C$_{1-12}$ alkyl, substituted C$_{1-12}$ alkyl, C$_{1-12}$ heteroalkyl, substituted C$_{6-12}$ heteroalkyl, C$_{3-12}$ cycloalkyl, substituted C$_{3-12}$ cycloalkyl, C$_{4-20}$ cycloalkylalkyl, substituted C$_{4-20}$ cycloalkylalkyl, C$_{4-20}$ heterocycloalkylalkyl, substituted C$_{4-20}$ heterocycloalkylalkyl, C$_{5-12}$ aryl, substituted C$_{5-12}$ aryl, C$_{5-12}$ heteroaryl, substituted C$_{5-12}$ heteroaryl, C$_{6-20}$ arylalkyl, substituted C$_{6-20}$ arylalkyl, C$_{6-20}$ heteroarylalkyl or substituted C$_{6-20}$ heteroarylalkyl.

In certain embodiments of a compound of Formula (III), n is the integer 1.

In certain embodiments of a compound of Foirnula (III), n is the integer 2.

In certain embodiments of a compound of Formula (III), each R$^5$, R$^7$ and R$^{22}$ is independently C$_{1-6}$ alkyl, substituted C$_{1-6}$ alkyl, C$_{3-7}$ cycloalkyl, substituted C$_{3-7}$ cycloalkyl, C$_{5-7}$ aryl or substituted C$_{5-7}$ aryl.

In certain embodiments of a compound of Formula (III), each R$^5$, R$^7$ and R$^{22}$ is independently hydrogen, methyl, ethyl, n-propyl, isopropyl, butyl, isobutyl, sec-butyl, tert-butyl, n-pentyl, isopentyl, sec-pentyl, neopentyl, dodecyl, 1,1-dimethoxyethyl, 1,1-diethoxyethyl, phenyl, 4-methoxyphenyl, benzyl, phenethyl, styryl, cyclopropyl, cyclobutyl, cyclopentyl, cyclohexyl, 2-pyridyl, 3-pyridyl or 4-pyridyl.

In certain embodiments of a compound of Formula (III), each R$^5$, R$^7$ and R$^{22}$ is independently hydrogen, methyl, ethyl, n-propyl, isopropyl, n-butyl, isobutyl, sec-butyl, tert-butyl, n-pentyl, isopentyl, sec-pentyl, neopentyl, dodecyl, 1,1-diethoxyethyl, phenyl, cyclohexyl or 3-pyridyl.

In certain embodiments of a compound of Formula (III), each R$^5$, R$^7$ and R$^{22}$ is independently hydrogen, methyl, ethyl, n-propyl, isopropyl, dodecyl, tert-butyl, phenyl or cyclohexyl.

In certain embodiments of a compound of Formula (III), each R$^5$, R$^7$ and R$^{22}$ is independently ethyl, isopropyl or dodecyl.

In certain embodiments of a compound of Formula (III), each R$^3$ and R$^4$ is independently hydrogen.

In certain embodiments of a compound of Formula (III), each R$^{23}$ is hydrogen, methyl, ethyl, n-propyl, isopropyl, tert-butyl, dodecyl, phenyl or cyclohexyl.

In certain embodiments of a compound of Formula (III), each R$^{23}$ is methyl.

In certain embodiments of a compound of Formula (III), each each substituent group is independently halogen, —NO$_2$, —OH, —NH$_2$, —CN, —CF$_3$, —OCF$_3$, =O, C$_{1-12}$ alkyl, substituted C$_{1-12}$ alkyl, C$_{1-12}$ alkoxy or substituted C$_{1-12}$ alkoxy, —COOR$^{10'}$ wherein R$^{10'}$ is hydrogen, C$_{1-3}$ alkyl or —(NR$^{11'}$)$_2$ wherein each R$^{11'}$ is independently hydrogen or C$_{1-3}$ alkyl.

In yet another embodiment, the compound of Formula (III) is a compound of Formula (XVII), Formula (XVIII) or Formula (XIX) or a pharmaceutically acceptable salt, solvate, tautomer or stereoisomer thereof;
wherein the compound of Formula (XVII) is:

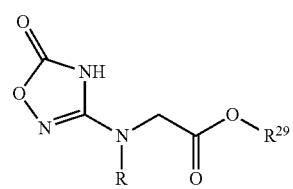

(XVII)

wherein R is —CH$_3$ or —CD$_3$;
R$^{29}$ is hydrogen, methyl, ethyl, n-propyl, isopropyl, tert-butyl, dodecyl, phenyl, -cyclohexyl, —CH$_2$—C(O)OR$^{43}$, —CH$_2$—(O)C(O)R$^{43}$, —CH$_2$—(O)C(O)OR$^{43}$ or

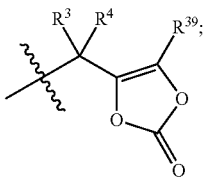

$R^{39}$ is hydrogen, methyl, ethyl, n-propyl, isopropyl, tert-butyl, dodecyl, phenyl or cyclohexyl;

$R^{43}$ is hydrogen, methyl, ethyl, n-propyl, isopropyl, tert-butyl, dodecyl, phenyl or cyclohexyl; and $R^3$ and $R^4$ are each independently hydrogen, $C_{1-12}$ alkyl or substituted $C_{1-12}$ alkyl; wherein the compound of Formula (XVIII) is:

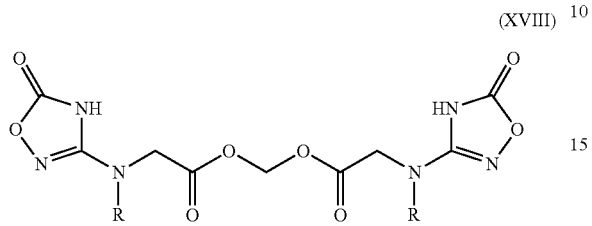
(XVIII)

wherein R is —$CH_3$ or —$CD_3$;

wherein the compound of Formula (XIX) is:

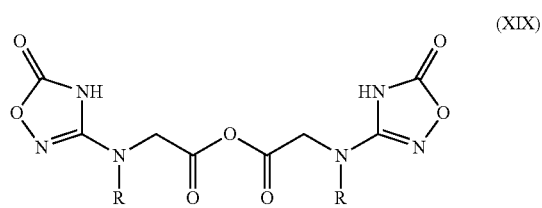
(XIX)

wherein R is —$CH_3$ or —$CD_3$.

In certain embodiments of a compound of Formula (XVII), each $R^{29}$ and $R^{43}$ is independently ethyl, isopropyl or dodecyl.

In certain embodiments of a compound of Formula (XVII), each $R^{39}$ is methyl. In certain embodiments of a compound of Formula (XVII) $R^3$ and $R^4$ are each hydrogen.

In certain embodiments a creatine prodrug is a compound of Formula (VI) or a pharmaceutically acceptable salt, solvate, tautomer or stereoisomer thereof:

wherein the compound of Formula (VI) is:

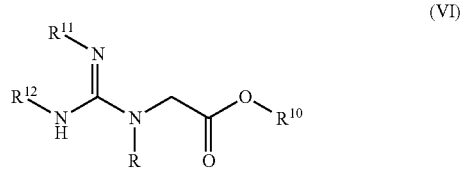
(VI)

wherein:

R is —$CH_3$ or —$CD_3$;

$R^{10}$ is hydrogen, $C_{1-12}$ alkyl, substituted $C_{1-12}$ alkyl, $C_{1-12}$ heteroalkyl, substituted $C_{1-12}$ heteroalkyl, $C_{3-12}$ cycloalkyl, substituted $C_{3-12}$ cycloalkyl, $C_{4-20}$ cycloalkylalkyl, substituted $C_{4-20}$ cycloalkylalkyl, $C_{4-20}$ heterocycloalkylalkyl, substituted $C_{4-20}$ heterocycloalkylalkyl, $C_{5-12}$ aryl, substituted $C_{5-12}$ aryl, $C_{5-12}$ heteroaryl, substituted $C_{5-12}$ heteroaryl, $C_{6-20}$ arylalkyl, substituted $C_{6-20}$ arylalkyl, $C_{6-20}$ heteroarylalkyl, substituted $C_{6-20}$ heteroarylalkyl, —C(O)$R^5$, —C(O)O$R^5$, —C(O)(N$R^3R^4$), —C($R^3R^4$)—C(O)O$R^{22}$, —C($R^3R^4$)—(O)C(O) $R^{22}$, —C($R^3R^4$)—(O)C(O)—O$R^{22}$;

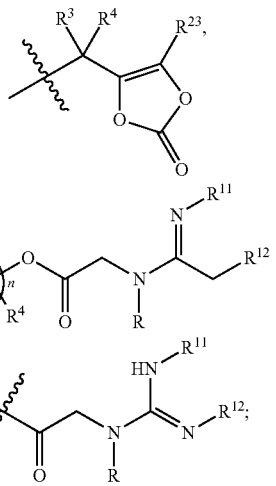

$R^{11}$ and $R^{12}$ are each independently hydrogen or —O$R^{13}$; or $R^{11}$ and $R^{12}$ are each —C(O)$R^5$, with the proviso that both $R^{11}$ and $R^{12}$ cannot be hydrogen $R^{13}$ is independently hydrogen, $C_{1-12}$ alkyl, substituted $C_{1-12}$ alkyl, $C_{1-12}$ heteroalkyl, substituted $C_{1-12}$ heteroalkyl, $C_{3-12}$ cycloalkyl, substituted $C_{3-12}$ cycloalkyl, $C_{4-20}$ cycloalkylalkyl, substituted $C_{4-20}$ cycloalkylalkyl, $C_{4-20}$ heterocycloalkylalkyl, substituted $C_{4-20}$ heterocycloalkylalkyl, $C_{5-12}$ aryl, substituted $C_{5-12}$ aryl, $C_{5-12}$ heteroaryl, substituted $C_{5-12}$ heteroaryl, $C_{6-20}$ arylalkyl, substituted $C_{6-20}$ arylalkyl, $C_{6-20}$ heteroarylalkyl, substituted $C_{6-20}$ heteroarylalkyl —CH(O$R^5$), —C(O)$R^5$, —C(O)O$R^5$ or —C(O)(N$R^3R^4$);

each $R^3$ and $R^4$ is independently hydrogen, $C_{1-12}$ alkyl or substituted $C_{1-12}$ alkyl;

$R^5$ is hydrogen, $C_{1-12}$ alkyl, substituted $C_{1-12}$ alkyl, $C_{1-12}$ heteroalkyl, substituted $C_{1-12}$ heteroalkyl, $C_{3-12}$ cycloalkyl, substituted,$C_{3-12}$ cycloalkyl, $C_{4-20}$ cycloalkylalkyl, substituted $C_{4-20}$ cycloalkylalkyl, $C_{4-20}$ heterocycloalkylalkyl, substituted $C_{4-20}$ heterocycloalkylalkyl, $C_{5-12}$ aryl, substituted $C_{5-12}$ aryl, $C_{5-12}$ heteroaryl, substituted $C_{5-12}$ heteroaryl, $C_{6-20}$ arylalkyl, substituted $C_{6-20}$ arylalkyl, $C_{6-20}$ heteroarylalkyl or substituted $C_{6-20}$ heteroarylalkyl;

$R^{23}$ is hydrogen, $C_{1-12}$ alkyl, substituted $C_{1-12}$ alkyl, $C_{5-12}$ cycloalkyl, substituted $C_{5-12}$ cycloalkyl, $C_{5-12}$ aryl, and $C_{5-12}$ substituted aryl, —C(O)—O$R^{22}$ or —C(O)—$R^{22}$;

$R^{22}$ is $C_{1-12}$ alkyl, substituted $C_{1-12}$ alkyl, $C_{1-12}$ heteroalkyl, substituted $C_{1-12}$ heteroalkyl, $C_{3-12}$ cycloalkyl, substituted $C_{3-12}$ cycloalkyl, $C_{4-20}$ cycloalkylalkyl, substituted $C_{4-20}$ cycloalkylalkyl, $C_{4-20}$ heterocycloalkylalkyl, substituted $C_{4-20}$ heterocycloalkylalkyl, $C_{5-12}$ aryl, substituted $C_{5-12}$ aryl, $C_{5-12}$ heteroaryl, substituted $C_{5-12}$ heteroaiyl, $C_{6-20}$ arylalkyl, substituted $C_{6-20}$ arylalkyl, $C_{6-20}$ heteroarylalkyl or substituted $C_{6-20}$ heteroarylalkyl; and n is an integer from 1 to 2.

In certain embodiments of a compound of Formula (VI), each $R^5$, $R^{10}$ and $R^{22}$ is independently $C_{1-6}$ alkyl, substituted $C_{1-6}$ alkyl, $C_{3-7}$ cycloalkyl, substituted $C_{3-7}$ cycloalkyl, $C_{5-7}$ aryl or substituted $C_{5-7}$ aryl.

In certain embodiments of a compound of Formula (VI), each $R^5$, $R^{10}$ and $R^{22}$ is independently hydrogen, methyl ethyl, n-propyl, isopropyl, butyl, isobutyl, sec-butyl, tert-butyl, n-pentyl, isopentyl, sec-pentyl, neopentyl, dodecyl, 1,1-dimethoxy ethyl, 1,1-diethoxyethyl, phenyl, 4-methoxyphenyl, benzyl, phenethyl, styryl, cyclopropyl, cyclobutyl, cyclopentyl, cyclohexyl, 2-pyridyl, 3-pyridyl or 4-pyridyl.

In certain embodiments of a compound of Formula (VI), each $R^5$, $R^{10}$ and $R^{22}$ is independently hydrogen, methyl, ethyl, n-propyl, isopropyl, n-butyl, isobutyl, sec-butyl, tert-butyl, n-pentyl, isopentyl, sec-pentyl, neopentyl, dodecyl, 1,1-diethoxyethyl, phenyl, cyclohexyl or 3-pyridyl.

In certain embodiments of a compound of Formula (VI), each $R^5$, $R^{10}$ and $R^{22}$ is independently hydrogen, methyl, ethyl, n-propyl, isopropyl, dodecyl, tert-butyl, phenyl or cyclohexyl.

In certain embodiments of a compound of Formula (VI), each $R^5$, $R^{10}$ and $R^{22}$ is independently ethyl, isopropyl or dodecyl.

In certain embodiments of a compound of Formula (VI), each $R^3$ and $R^4$ is independently hydrogen.

In certain embodiments of a compound of Formula (VI), Ru and $R^{12}$ are each hydroxyl.

In certain embodiments of a compound of Formula (VI) one of $R^{11}$ or $R^{12}$ is hydrogen and the other is hydroxyl.

In certain embodiments of a compound of Formula (VI), each $R^{23}$ is hydrogen, methyl, ethyl, n-propyl, isopropyl, tert-butyl, dodecyl, phenyl or cyclohexyl.

In certain embodiments of a compound of Formula (VI), each $R^{23}$ is methyl.

In certain embodiments of a compound of Formula (VI), each substituent group is independently halogen, $-NO_2$, $-OH$, $-NH_2$, $-CN$, $-CF_3$, $-OCF_3$, $=O$, $C_{1-12}$ alkyl, substituted $C_{1-12}$ alkyl, $C_{1-12}$ alkoxy or substituted $C_{1-12}$ alkoxy, $-COOR^{10'}$ wherein $R^{10'}$ is hydrogen, $C_{1-3}$ alkyl or $-(NR^{11'})_2$ wherein each $R^{11'}$ is independently hydrogen or $C_{1-3}$ alkyl.

In certain embodiments of a compound of Formula (VI), n is the integer 1.

In still another embodiment, the compound of Formula (VI) is a compound of Formula (XXII), Formula (XXIII), Formula (XXIV), Formula (XXV), Formula (XXVI), Formula (XXVII) or Formula (XXVIII) or a pharmaceutically acceptable salt, solvate, tautomer or stereoisomer thereof;

wherein the compound of formula (XXII) is:

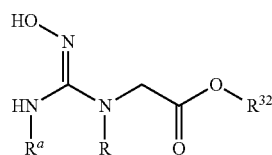

(XXII)

wherein the compound of formula (XXIII) is:

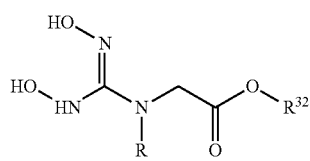

(XXIII)

wherein the compound of formula (XXIV) is:

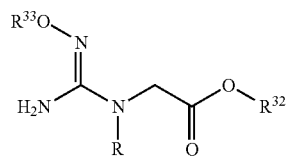

(XXIV)

wherein the compound of Formula (XXV) is:

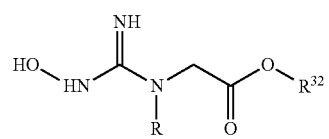

(XXV)

wherein the compound of Formula (XXVI) is:

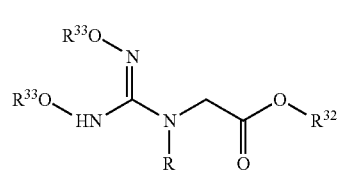

(XXVI)

wherein the compound of Formula (XXVII) is:

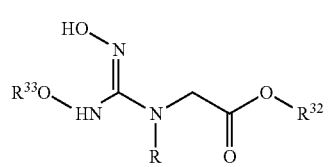

(XXVII)

wherein the compound of Formula (XXVIII) is:

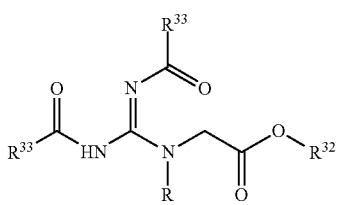

(XXVIII)

wherein R is $-CH_3$ or $-CD_3$;

$R^a$ is hydrogen, methyl, ethyl, n-propyl, isopropyl, n-butyl, isobutyl, tert-butyl;

$R^{32}$ is hydrogen, methyl, ethyl, n-propyl, isopropyl, tert-butyl, dodecyl, phenyl, cyclohexyl;

$-CH_2-C(O)OR^{43}$, $-CH_2-(O)C(O)R^{43}$, $-CH_2-(O)C(O)OR^{43}$ or

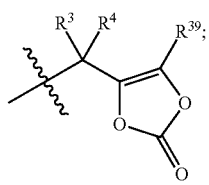

$R^{39}$ is hydrogen, methyl, ethyl, n-propyl, isopropyl, tert-butyl, dodecyl, phenyl or cyclohexyl;

each $R^{33}$ is independently hydrogen, methyl, ethyl, n-propyl, isopropyl, tert-butyl, dodecyl, phenyl or cyclohexyl;

$R^{43}$ is hydrogen, methyl, ethyl, n-propyl, isopropyl, tert-butyl, dodecyl, phenyl or cyclohexyl; and $R^3$ and $R^4$ are each independently hydrogen, $C_{1-12}$ alkyl or substituted $C_{1-12}$ alkyl.

In certain embodiments each $R^{32}$ and $R^{33}$ is independently ethyl, isopropyl or dodecyl.

In certain embodiments R is methyl.

In certain embodiments $R^3$ and $R^4$ are each hydrogen.

In certain embodiments a creatine prodrug is a compound of Formula (VII) or a pharmaceutically acceptable salt, solvate, tautomer or stereoisomer thereof:

wherein the compound of Formula (VII) is:

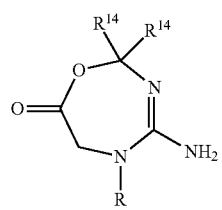

(VII)

wherein:

R is —CH$_3$ or —CD$_3$;

each $R^{14}$ is independently hydrogen, $C_{1-12}$ alkyl, substituted $C_{1-12}$ alkyl, $C_{1-12}$ heteroalkyl, substituted $C_{1-12}$ heteroalkyl, $C_{3-12}$ cycloalkyl, substituted $C_{3-12}$ cycloalkyl, $C_{4-20}$ cycloalkylalkyl, substituted $C_{4-20}$ cycloalkylalkyl, $C_{4-20}$ heterocycloalkylalkyl, substituted $C_{4-20}$ heterocycloalkylalkyl, $C_{5-12}$ aryl, substituted $C_{5-12}$ aryl, $C_{5-12}$ heteroaryl, substituted $C_{5-12}$ heteroaryl, $C_{6-20}$ arylalkyl, substituted $C_{6-20}$ arylalkyl, $C_{6-20}$ heteroarylalkyl, substituted $C_{6-20}$ heteroarylalkyl —CH(OR$^5$), —C(O)R$^5$, —C(O)OR$^5$ or —C(O)(NR$^3$R$^4$);

each $R^3$ and $R^4$ is independently hydrogen, $C_{1-12}$ alkyl or substituted $C_{1-12}$ alkyl; and $R^5$ is hydrogen, $C_{1-6}$ alkyl, substituted $C_{1-12}$ alkyl, $C_{1-12}$ heteroalkyl, substituted $C_{1-12}$ heteroalkyl, $C_{3-12}$ cycloalkyl, substituted $C_{3-12}$ cycloalkyl, $C_{4-20}$ cycloalkylalkyl, substituted $C_{4-20}$ cycloalkylalkyl, $C_{4-20}$ heterocycloalkylalkyl, substituted $C_{4-20}$ heterocycloalkylalkyl, $C_{5-12}$ aryl, substituted $C_{5-12}$ aryl, $C_{5-12}$ heteroaryl, substituted $C_{5-12}$ heteroaryl, $C_{6-20}$ arylalkyl, substituted $C_{6-20}$ arylalkyl, $C_{6-20}$ heteroarylalkyl or substituted $C_{6-20}$ heteroarylalkyl.

In certain embodiments of a compound of Formula (VII), $R^5$ is $C_{1-12}$ alkyl, substituted $C_{1-6}$ alkyl, $C_{3-7}$ cycloalkyl, substituted $C_{3-7}$ cycloalkyl, $C_{5-7}$ aryl or substituted $C_{5-7}$ aryl.

In certain embodiments of a compound of Formula (VII), $R^5$ is hydrogen, methyl, ethyl, n-propyl, isopropyl, butyl, isobutyl, sec-butyl, tert-butyl, n-pentyl, isopentyl, sec-pentyl, neopentyl, dodecyl, 1,1-dimethoxyethyl, 1,1-diethoxyethyl, phenyl, 4-methoxyphenyl, benzyl, phenethyl, styryj, cyclopropyl, cyclobutyl, cyclopentyl, cyclohexyl, 2-pyridyl, 3-pyridyl or 4-pyridyl.

In certain embodiments of a compound of Formula (VII), $R^5$ is hydrogen, methyl, ethyl, n-propyl, isopropyl, n-butyl, isobutyl, sec-butyl, tert-butyl, n-pentyl, isopentyl, sec-pentyl, neopentyl, dodecyl, 1,1-diethoxyethyl, phenyl, cyclohexyl or 3-pyridyl.

In certain embodiments of a compound of Formula (VII), $R^5$ is hydrogen, methyl, ethyl, n-propyl, isopropyl, dodecyl, tert-butyl, phenyl or cyclohexyl.

In certain embodiments of a compound of Formula (VII), $R^5$ is ethyl, isopropyl or dodecyl.

In certain embodiments of a compound of Formula (VII), each $R^{14}$ is independently hydrogen, methyl, ethyl, n-propyl, isopropyl, tert-butyl, dodecyl, phenyl or cyclohexyl.

In certain embodiments of a compound of Formula (VII), one $R^{14}$ is methyl and the other $R^{14}$ is hydrogen.

In certain embodiments of a compound of Formula (VH), each $R^3$ and $R^4$ is independently hydrogen.

In certain embodiments of a compound of Formula (VII), each substituent group is independently halogen, —NO$_2$, —OH, —NH$_2$, —CN, —CF$_3$, —OCF$_3$, =O, $C_{1-12}$ alkyl, substituted $C_{1-12}$ alkyl, $C_{1-12}$ alkoxy or substituted $C_{1-12}$ alkoxy, —COOR$^{10'}$ wherein R$^{10'}$ is hydrogen, $C_{1-3}$ alkyl or —(NR$^{11'}$)$_2$ wherein each R$^{11'}$ is independently hydrogen or $C_{1-3}$ alkyl.

In yet another embodiment, the compound of Formula (YII) is a compound of Formula (XXIX) or a pharmaceutically acceptable salt, solvate, tautomeror stereoisomer thereof;

wherein the compound of Formula (XXIX) is:

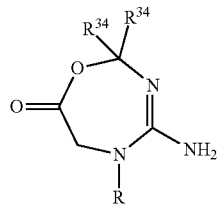

(XXIX)

wherein R is —CH$_3$ or —CD$_3$; and each $R^{34}$ is independently hydrogen, methyl, ethyl, n-propyl, isopropyl, tert-butyl, dodecyl, phenyl or cyclohexyl.

In certain embodiments of a compound of Formula (XXIX), one $R^{34}$ is methyl and the other $R^{34}$ is hydrogen.

Synthesis of Creatine Prodrugs

Those of ordinary skill in the art will appreciate that creatine prodrug compounds of Formulae (I), (III), (VI), (VII), and any subgenera or species thereof, or a pharmaceutically acceptable salt, solvate, tautomer or stereoisomer thereof may be prepared via general synthetic methods available in the art (e.g., Wuts and Greene, "Protective Groups in Organic Synthesis," John Wiley & Sons, 4th ed. 2006; Harrison et al., "Compendium of Organic Synthetic Methods," Vols. 1-11, John Wiley & Sons 1971-2003; Larock "Comprehensive Organic Transformations," John Wiley & Sons, 2nd ed. 2000; and Paquette, "Encyclopedia of Reagents for Organic Synthesis," John Wiley & Sons, 11th ed. 2003). Starting materials useful for preparing compounds and intermediates thereof, are commercially available or can be prepared by well-known synthetic methods.

Pharmaceutical Compositions

Pharmaceutical compositions of the invention can comprise a compound of the invention and a pharmaceutically acceptable vehicle. A pharmaceutical composition can comprise a therapeutically effective amount of compound of the invention and a pharmaceutically acceptable vehicle. In certain embodiments, a pharmaceutical composition can include more than one compound of the invention. Pharmaceutically acceptable vehicles include diluents, adjuvants, excipients, and carriers.

Pharmaceutical compositions can be produced using standard procedures (see, e.g., "Remington's The Science and Practice of Pharmacy," 21st edition, Lippincott, Williams & Wilcox, 2005). Pharmaceutical compositions may be manufactured by means of conventional mixing, dissolving, granulating, dragee-making, levigating, emulsifying, encapsulating, entrapping or lyophilizing processes. Pharmaceutical compositions may be formulated in a conventional manner using one or more physiologically acceptable carriers, diluents, excipients or auxiliaries, which facilitate processing of compounds disclosed herein into preparations, which can be used pharmaceutically. Proper formulation can depend, in part, on the route of administration.

Pharmaceutical compositions of the invention can provide therapeutic plasma concentrations of a creatine creatine upon administration to a patient. The promoiety of a creatine prodrug can be cleaved in vivo either chemically and/or enzymatically to release creatine. One or more enzymes present in the intestinal lumen, intestinal tissue, blood, liver, brain or any other suitable tissue of a mammal can enzymatically cleave the promoiety of the administered prodrugs. For example, the promoiety can be cleaved after absorption by the gastrointestinal tract (e.g., in intestinal tissue, blood, liver or other suitable tissue of a mammal). In certain embodiments, a creatine remains conjugated to the promoiety during transit across the intestinal mucosal barrier to provide protection from presystemic metabolism. In certain embodiments, a creatine prodrug is essentially not metabolized to release the corresponding creatine within enterocytes, but is metabolized to the parent drug within the systemic circulation. Cleavage of the promoiety of a creatine prodrug after absorption by the gastrointestinal tract may allow the prodrug to be absorbed into the systemic circulation either by active transport, passive diffusion or by a combination of both active and passive processes.

Creatine prodrugs can remain intact until after passage of the prodrug through a biological barrier, such as the blood-brain barrier. In certain embodiments, prodrugs of the invention can be partially cleaved, e.g., one or more, but not all, of the promoieties can be cleaved before passage through a biological barrier or prior to being taken up by a cell, tissue or organ.

Creatine prodrugs can remain intact in the systemic circulation and be absorbed by cells of an organ, either passively or by active transport mechanisms. In certain embodiments, a creatine prodrug will be lipophilic and can passively translocate through cellular membranes. Following cellular uptake, the prodrug can be cleaved chemically and/or enzymatically to release the corresponding creatine into the cellular cytoplasm, resulting in an increase in the intracellular concentration of the creatine. In certain embodiments, a prodrug can be permeable to intracellular membranes such as the mitochondrial membrane, and thereby facilitate delivery of a prodrug, and following cleavage of the promoiety or promoieties, a creatine, to an intracellular organelle such as mitochondria.

In certain embodiments, a pharmaceutical composition can include an adjuvant; that facilitates absorption of a compound of the invention through the gastrointestinal epithelia. Such enhancers can, for example, open the tight-junctions in the gastrointestinal tract or modify the effect of cellular components, such as p-glycoprotein and the like. Suitable enhancers can include alkali metal salts of salicylic acid, such as sodium salicylate, caprylic or capric acid, such as sodium caprylate or sodium cap rate, and the like. Enhancers can include, for example, bile salts, such as sodium deoxycholate. Various p-glycoprotein modulators are described in U.S. Pat. Nos. 5,112,817 and 5,643,909. Various absorption enhancing compounds and materials are described in U.S. Pat. No. 5,824,638, and U.S. application Ser. No. 2006/0046962, Other adjuvants that enhance permeability of cellular membranes include resorcinol, surfactants, polyethylene glycol, and bile acids.

In certain embodiments, a pharmaceutical composition can include an adjuvant that reduces enzymatic degradation of a compound of of the invention. Microencapsulation using protenoid microspheres, liposomes or polysaccharides can also be effective in reducing enzymatic degradation of administered compounds.

A pharmaceutical composition can also include one of more pharmaceutically acceptable vehicles, including excipients, adjuvants, carriers, diluents, binders, lubricants, disintegrants, colorants, stabilizers, surfactants, fillers, buffers, thickeners, emulsifiers, wetting agents, and the like. Vehicles can be selected to alter the porosity and permeability of a pharmaceutical composition, alter hydration and disintegration properties, control hydration, enhance manufacturability, etc.

In certain embodiments, a pharmaceutical composition can be formulated for oral administration. Pharmaceutical compositions formulated for oral administration can provide for uptake of a compound of the invention throughout the gastrointestinal tract or in a particular region or regions of the gastrointestinal tract. In certain embodiments, a pharmaceutical composition can be formulated to enhance uptake a compound of the invention from the upper gastrointestinal tract, and in certain embodiments, from the small intestine. Such compositions can be prepared in a manner known in the pharmaceutical art and can further comprise, in addition to a compound of the invention, one or more pharmaceutically acceptable vehicles, permeability enhancers, and/or a second therapeutic agent.

In certain embodiments, a pharmaceutical composition can further comprise a substance to enhance, modulate and/or control release, bioavailability, therapeutic efficacy, therapeutic potency, stability, and the like. For example, to enhance therapeutic efficacy a compound of the invention can be co-administered with one or more active agents to increase the absorption or diffusion of the drug from the gastrointestinal tract or to inhibit degradation of the drug in the systemic circulation. In certain embodiments, a compound of the invention can be cot administered with active agents having pharmacological effects that enhance the therapeutic efficacy of the compound of the invention.

In certain embodiments, a pharmaceutical composition can further comprise substances to enhance, modulate and/or control release, bioavailability, therapeutic efficacy, therapeutic potency, stability, and the like. For example, to enhance therapeutic efficacy a compound of the invention can be co-administered with one or more active agents to increase the absorption or diffusion of a compound of the invention from the gastrointestinal tract or to inhibit degradation of the drug in the systemic circulation. In certain embodiments, a compound of the invention can be co-administered with active agents having pharmacological effects that enhance the therapeutic efficacy of a compound of the invention.

Pharmaceutical compositions can take the form of solutions, suspensions, emulsions, tablets, pills, pellets, capsules, capsules containing liquids, powders, sustained-release formulations, suppositories, emulsions, aerosols, sprays, suspensions or any other form suitable for use. Pharmaceutical compositions for oral delivery may be in the form of tablets, lozenges, aqueous or oily suspensions, granules, powders, emulsions, capsules, syrups or elixirs, for example. Orally administered compositions may contain one or more optional agents, for example, sweetening agents such as fructose, aspartame or saccharin, flavoring agents such as peppermint, oil of wintergreen or cherry coloring agents and preserving agents, to provide a pharmaceutically palatable preparation. Moreover, when in tablet or pill form, the compositions may be coated to delay disintegration and absorption in the gastrointestinal tract, thereby providing a sustained action over an extended period of time. Oral compositions can include standard vehicles such as mahnitol, lactose, starch, magnesium stearate, sodium saccharine, cellulose, magnesium carbonate, etc. Such vehicles can be of pharmaceutical grade. For oral liquid preparations such as, for example, suspensions, elixirs, arid solutions, suitable carriers, excipients or diluents include water, saline, alkyleneglycols (e.g., propylene glycol), polyalkylene glycols (e.g., polyethylene glycol) oils, alcohols, slightly acidic buffers between pH 4 and pH 6 (e.g., acetate, citrate, ascorbate at between about 5 mM to about 50 mM), etc. Additionally, flavoring agents, preservatives, coloring agents, bile salts, acylcarnitines, and the like may be added.

When a compound of the invention is acidic, it may be included in any of the above-described formulations as the free acid, a pharmaceutically acceptable salt, solvate* a solvate or a hydrate. Pharmaceutically acceptable salts substantially retain the activity of the free acid, may be prepared by reaction with bases, and tend to be more soluble in aqueous and other protic solvents than the corresponding free acid form. In some embodiments, sodium salts of a compound of the invention are used in the above-described formulations.

Pharmaceutical compositions of the invention can formulated for parenteral administration including administration by injection, for example, into a vein (intravenously), an artery (intraarterially), a muscle (intramuscularly), under the skin (subcutaneously or in a depot formulation), to the pericardium, to the coronary arteries or used as a solution for delivery to a tissue or organ, for example, use in a cardiopulmonary bypass machine or to bathe transplant tissues or organs. Injectable compositions can be pharmaceutical compositions for any route of injectable administration, including, but not limited to, intravenous, intrarterial, intracoronary, pericardial, perivascular, intramuscular, subcutaneous, intradermal, intraperitoneal, and intraarticular. In certain embodiments, an injectable pharmaceutical composition can be a pharmaceutically appropriate composition for administration directly into the heart, pericardium or coronary arteries.

Pharmaceutical compositions of the invention suitable for parenteral administration can comprise one or more compounds of the invention in combination with one or more pharmaceutically acceptable sterile isotonic aqueous, water-miscible or non-aqueous vehicles. Pharmaceutical compositions for parenteral use may include substances that increase and maintain drug solubility such as complexing agents and surface acting agents, compounds that make the solution isotonic or near physiological pH such as sodium chloride, dextrose, and glycerin, substances that enhance the chemical stability of a solution such as antioxidants, inert gases, chelating agents, and buffers, substances that enhance the chemical and physical stability, substances that minimize self aggregation or interfacial induced aggregation, substances that minimize protein interaction with interfaces, preservatives including antimicrobial agents, suspending agents, emulsifying agents, and combinations of any of the foregoing. Pharmaceutical compositions for parenteral administration can be formulated as solutions, suspensions, emulsions, liposomes, microspheres, nanosystems, and powder to be reconstituted as solutions. Parenteral preparations are described in "Remington, The Science and Practice of Pharmacy," 21st edition, Lippincott, Williams & Wilkins, Chapter 41-42, pages 802-849, 2005.

In certain embodiments a pharmaceutical composition can be formulated for bathing transplantation tissue or organs before, during or after transit to an intended recipient. Such compositions can be used before or during preparation of a tissue or organ for transplant. In certain embodiments, a pharmaceutical composition can be a cardioplegic solution administered during cardiac surgery. In certain embodiments, a pharmaceutical composition can be used, for example, in conjunction with a cardiopulmonary bypass machine to provide the pharmaceutical composition to the heart. Such pharmaceutical compositions can be used during the induction, maintenance or reperfusion stages of cardiac-.surgery (see e.g., Chang et al., Masui 2003, 52(4), 356-62; Ibrahim et al., Eur. J. Cardiothorac Surg 1999, 15(1), 75-83; von Oppell et al., J Thorac Cardiovasc Surg. 1991, 102(3), 405-12; and Ji et al., J. Extra Corpor Technol 2002, 34(2), 107-10). In certain embodiments, a pharmaceutical composition can be delivered via a mechanical device such as a pump or perfuser (see e.g., Hou and March, J Invasive Cardiol 2003, 15(1), 13-7; Maisch et al., Am. J Cardiol 2001, 88(11), 1323-6; and Macris and Igo, Clin Cardiol 1999, 22 (1, Suppl 1), 136-9).

For prolonged delivery, a pharmaceutical composition can be provided as a depot preparation, for administration by implantation, e.g., subcutaneous, intradermal or intramuscular injection. Thus, in certain embodiments, a pharmaceutical composition can be formulated with suitable polymeric or hydrophobic materials, e.g., as an emulsion in a pharmaceutically acceptable oil, ion exchange resins or as a sparingly soluble derivative, e.g., as a sparingly soluble salt form of a compound of the invention.

Pharmaceutical compositions of the invention can be formulated so as to provide immediate, sustained or delayed release of a compound of Formula (I) and/or Formula (II) after administration to the patient by employing procedures known in the art (see, e.g., Allen et al., "Ansel's Pharmaceutical Dosage Forms and Drug Delivery Systems," 8th ed., Lippincott, Williams & Wilkins, August 2004).

Dosage Forms

Pharmaceutical compositions of the invention can be formulated in a unit dosage form. Unit dosage form refers to a physically discrete unit suitable as a unitary dose for patients undergoing treatment, with each unit containing a predetermined quantity of a compound of the invention calculated to produce an intended therapeutic effect. A unit dosage form can be for a single daily dose or one of multiple daily doses, e.g., 2 to 4 times per day. When multiple daily doses are used, the unit dosage can be the same or different for each dose. One or more dosage forms can comprise a dose, which may be administered to a patient at a single point in time or during a time interval.

Pharmaceutical compositions of the invention can be used in dosage forms that provide immediate release and/or controlled release of a compound of the invention. The appropriate type of dosage form can depend on the disease, disorder or condition being treated, and on the method of administration. For example, for the treatment of acute ischemic conditions such as cardiac failure or stroke the use of an immediate release pharmaceutical composition or dosage form administered parenterally may be appropriate. For treatment of chronic neurodegenerative disorders, controlled release pharmaceutical composition or dosage form administered orally may be appropriate.

In certain embodiments, a dosage form can be adapted to be administered to a patient no more than twice per day, and in certain embodiments, only once per day. Dosing may be provided alone or in combination with other drugs and may continue as long as required for effective treatment of the disease, disorder or condition.

Pharmaceutical compositions comprising a compound of the invention can be formulated for immediate release for parenteral administration oral administration or by any other appropriate route of administration.

Controlled drug delivery systems can be designed to deliver a drug in such a way that the drug level is maintained within the therapeutic windows and effective and safe blood levels are maintained for a period as long as the system continues to deliver the drug at a particular rate. Controlled drug delivery can produce substantially constant blood levels of a drug as compared to fluctuations observed with immediate release dosage forms. For some drugs, maintaining a constant bloodstream and tissue concentration throughout the course of therapy is the most desirable mode of treatment. Immediate release of these drugs can cause blood levels to peak above the level required to elicit the desired response, which wastes the drug and may cause or exacerbate toxic side effects. Controlled drug delivery can result in optimum therapy, and not only can reduce the frequency of dosing, and may also reduce the severity of side effects. Examples of controlled release dosage forms include dissolution controlled systems, diffusion controlled systems, ion exchange resins, osmotically controlled systems, erodable matrix systems, pH independent formulations, gastric retention systems, and the like.

In certain embodiments, an oral dosage form of the invention can be a controlled release dosage form. Controlled delivery technologies can improve the absorption of a drug in a particular region or regions of the gastrointestinal tract. The appropriate oral dosage form for a particular pharmaceutical composition of the invention can depend, at least in parti on the gastrointestinal absorption properties of the compound of the invention, the stability of the compound of the invention in the gastrointestinal tract, the pharmacokinetics of the compound of the invention, and the intended therapeutic profile. An appropriate controlled release oral dosage form can be selected for a particular the compound of the invention. For example, gastric retention oral dosage forms can be appropriate for compounds absorbed primarily from the upper gastrointestinal tract, and sustained release oral dosage forms can be appropriate for compounds absorbed primarily form the lower gastrointestinal tract.

Certain compounds are absorbed primarily from the small intestine. In general, compounds traverse the length of the small intestine in about 3 to 5 hours. For compounds that are. not easily absorbed by the small intestine or that do not dissolve readily, the window for active agent absorption in the small intestine may be too short to provide a desired therapeutic effect. Gastric retention dosage forms, i.e., dosage forms that are designed to be retained in the stomach for a. prolonged period of time, can increase the bioavailability of drugs that are most readily absorbed by the upper gastrointestinal tract. The residence time of a conventional dosage form in the stomach is 1 to 3 hours. After transiting the stomach, there is approximately a 3 to 5 hour window of bioavailability before the dosage form reaches the col on. However, if the dosage form is retained in the stomach, the drug can be released before it reaches the small intestine and will enter the intestine in solution in a state in which it can be more readily absorbed. Another use of gastric retention dosage forms is to improve the bioavailability of a drug that is unstable to the basic conditions of the intestine (see, e.g., Hwang et al., Critical Reviews in Therapeutic Drug Carrier Systems, 1998, 15, 243-284). To enhance drug absorption from the upper gastrointestinal tract, several gastric retention dosage forms have been developed. Examples include, hydrogels (see, e.g., U.S. Application No. 2003/0008007), buoyant matrices (see, e.g., U.S. Application No. 2006/0013876), polymer sheets (see, e.g., U.S. Application No. 2005/0249798), microcellular foams (see, e.g., U.S. Application No. 2005/0202090), and swellable dosage forms (see, e.g., U.S. Application No. 2005/0019409; US. Pat. No. 6,797,283; U.S. Application No. 2006/0045865; U.S. Application No. 2004/0219186; U.S. Pat. Nos. 6,723,340; 6,476, 006; 6,120,803; 6,548,083; 6,635,280; 5,780,057). Bioadhesive polymers can also provide a vehicle for controlled delivery of drugs to a number of mucosal surfaces in addition to the gastric mucosa (see, e.g., U.S. Pat. Nos. 6,235,313; 6,207,197; U.S. Application No. 2006/0045865 and U.S. Application No. 2005/0064027). Ion exchange resins have been shown to prolong gastric retention, potentially by adhesion.

In a swelling and expanding system, dosage forms that swell and change,density in relation to the surrounding gastric content can be retained in the stomach for longer than a conventional dosage form. A dosage form can absorb water and swell to form a gelatinous outside surface and float on the surface of gastric content surface while maintaining integrity before releasing a drug. Fatty materials can be added to impede wetting and enhance flotation when hydration and swelling alone are insufficient. Materials that release gases may also be incorporated to reduce the density of a gastric retention dosage form. Swelling also can significantly increase the size of a dosage form and thereby impede discharge of the non-disintegrated swollen solid dosage form through the pylorus into the small intestine. Swellable dosage forms can be formed by encapsulating a core containing drug and a swelling agent or by combining a drug, swelling agent, and one or more erodible polymers.

Gastric retention dosage forms can also be in the form of a folded thin sheet containing a drug and water-insoluble diffusible polymer that opens in the stomach to its original size and shape, which is sufficiently large to prevent or inhibit passage of the expanded dosage from through the pyloric sphincter.

Floating and buoyancy gastric retention dosage forms can be designed to trap gases within sealed encapsulated cores that can float on the gastric contents, and thereby be retained in the stomach for a longer time, e.g., 9 to 12 hours. Due to the buoyancy effect, these systems can provide a protective layer preventing the reflux of gastric content into the esophageal region and can also be used for controlled release devices. A floating system can, for example, contain hollow cores containing drug coated with a protective membrane. The trapped air in the cores floats the dosage from on the gastric content until the soluble ingredients are released and the system collapses. In other floating systems, cores contain drug and chemical substances capable of generating gases when activated. For example, coated cores, containing carbonate and/or bicarbonate can generate carbon dioxide in the reaction with hydrochloric acid in the stomach or incorporated organic acid in the system. The gas generated by the reaction is retained to float the dosage form. The inflated dosage form later collapses and clears form the stomach when the generated gas permeates slowly through the protective coating.

Bioadhesive polymers can also provide a vehicle for controlled delivery of drugs to a number of mucosal surfaces in addition to the gastric mucosa (see, e.g., U.S. Pat. Nos.

6,235,313; and 6,207,197). A bioadhesive system can be designed by incorporation of a drug and other excipients within a bioadhesive polymer. On ingestion, the polymer hydrates and adheres to the mucus membrane of the gastrointestinal tract. Bioadhesive polymers can be selected that adhere to a desired region or regions of the gastrointestinal tract. Bioadhesive polymers can be selected to optimized delivery to targeted regions of the gastrointestinal tract including the stomach and small intestine. The mechanism of the adhesion is thought to be through the formation of electrostatic and hydrogen bonding at the polymer-mucus boundary. U.S. Application Nos. 2006/0045865 and 2005/0064027 disclose bioadhesive delivery systems which are useful for drug delivery to both the upper and lower gastrointestinal tract.

Ion exchange resins have been shown to prolong gastric retention, potentially by adhesion.

Gastric retention oral dosage forms can be appropriately used for delivery of drugs that are absorbed mainly from the upper gastrointestinal tract. For example, certain compounds of the invention may exhibit limited colonic absorption, and be absorbed primarily from the upper gastrointestinal tract. Thus, dosage forms that release the compound of the invention in the upper gastrointestinal tract and/or retard transit of the dosage form through the upper gastrointestinal tract will tend to enhance the oral bioavailability of the compound of the invention. Other forms of creatine prodrugs disclosed herein can be appropriately used with gastric retention dosage forms.

Polymer matrices have also been used to achieve controlled release of the drug over a prolonged period of time. Such sustained or controlled release can be achieved by limiting the rate by which the surrounding gastric fluid can diffuse through the matrix and reach the drug, dissolve the drug arid diffuse out again with the dissolved dhjg or by using a matrix that slowly erodes, continuously exposing fresh drug to the surrounding fluid. Disclosures of polymer matrices that function by these methods are found, for example, in Skinner, U.S. Pat. Nos. 6,210,710 and 6,217,903; 5,451,409; 5,945,125; PCT International Publication No. WO 96/26718; U.S. Pat. Nos. 4,915,952; 5,328,942; 5,783;212; 6,120,803; and 6,090,411.

Other drug delivery devices that remain in the stomach for extended periods of time include, for example, hydrogel reservoirs containing particles (U.S. Pat. No. 4,871,548); swellable hydroxypropylmethylcellulose polymers (U.S. Pat. No. 4,871,548); planar bioerodible polymers (U.S. Pat. No. 4,767,627); plurality of compressible retention arms (U.S. Pat. No. 5,443,843); hydrophilic water-swellable, cross-linked polymer particles (U.S. Pat. No. 5,007,790); and albumin-cross-linked polyvinylpyrrolidone hydrogels (Park et al., J. Controlled Release 1992,19, 131-134).

In certain embodiments, pharmaceutical compositions of the invention can be practiced with a number of different dosage forms, which can be adapted to provide sustained release of the compound of the invention upon oral administration. Sustained release oral dosage forms can be used to release drugs over a prolonged time period and are useful when it is desired that a drug or drug form be delivered to the lower gastrointestinal tract. Sustained release oral dosage forms include diffusion-controlled systems such as reservoir devices and matrix devices, dissolution-controlled systems, osmotic systems, and erosion-controlled systems. Sustained release oral dosage forms and methods of preparing the same are well known in the art (see, for example, "Remington's Pharmaceutical Sciences," Lippincott, Williams & Wilkins, 21st edition, 2005, Chapters 46 and 47; Langer, Science 1990, 249, 1527-1533; and Rosoff, "Controlled Release of Drugs," 1989, Chapter 2).

Sustained release oral dosage forms include any oral dosage form that maintains therapeutic concentrations of a drug in a biological fluid such as the plasma, blood, cerebrospinal fluid or in a tissue or organ for a prolonged time period. Sustained release oral dosage forms include diffusion-controlled systems such as reservoir devices and matrix devices, dissolution-controlled systems, osmotic systems, and erosion-controlled systems. Sustained release oral dosage forms and methods of preparing the same are well known in the art (see, for example, "Remington's: The Science and Practice of Pharmacy," Lippincott, Williams & Wilkins, 21st edition, 2005, Chapters 46 and 47; Langer, Science 1990, 249, 1527-1533; and Rosoff, "Controlled Release of Drugs," 1989, Chapter 2).

In diffusion-controlled systems, a water-insoluble polymer controls the flow of fluid and the subsequent egress of dissolved drug from the dosage form. Both diffusional and dissolution processes are involved in release of drug from the dosage form. In reservoir devices, a core comprising a drug is coated with the polymer, and in matrix systems, the drug is dispersed throughout the matrix. Cellulose polymers such as ethylcellulose or cellulose acetate can be used in reservoir devices. Examples of materials useful in matrix systems include methacrylates, acrylates, polyethylene, acrylic acid copolymers, polyvinylchloride, high molecular weight polyvinylalcohols, cellulose derivates, and fatty compounds such as fatty acids, glycerides, and carnauba wax.

In dissolution-controlled systems, the rate of dissolution of the drug is controlled by slowly soluble polymers or by microencapsulation. Once the coating is dissolved, the drug becomes available for dissolution. By varying the thickness and/or the composition of the coating or coatings, the rate of drug release can be controlled. In some dissolution-controlled systems, a fraction of the total dose can comprise an immediate-release component. Dissolution-controlled systems include encapsulated/reservoir dissolution systems and matrix dissolution systems. Encapsulated dissolution systems can be prepared by coating particles or granules of drug with slowly soluble polymers of different thickness or by microencapsulation. Examples of coating materials useful in dissolution-controlled systems include gelatin, carnauba wax, shellac, cellulose acetate phthalate, and cellulose acetate butyrate. Matrix dissolution devices can be prepared, for example, by compressing a drug with a slowly soluble polymer earner into a tablet form.

The rate of release of drug from osmotic pump systems is determined by the inflow of fluid across a semipermeable membrane into a reservoir, which contains an osmotic agent. The drug is either mixed with the agent or is located in a reservoir. The dosage form contains one or more small orifices from which dissolved drug is pumped at a rate determined by the rate of entrance of water due to osmotic pressure. As osmotic pressure within the dosage form increases, the drug is released through the orifice(s). The rate of release is constant and can be controlled within tight limits yielding relatively constant plasma and/or blood concentrations of the drug. Osmotic pump systems can provide a constant release of drug independent of the environment of the gastrointestinal tract. The rate of drug release can be modified by altering the osmotic agent and the sizes of the one or more orifices.

The release of drug from erosion-controlled systems is determined by the erosion rate of a carrier matrix. Drug is dispersed throughout the polymer and the rate of drug release depends on the erosion rate of the polymer. The drug-containing polymer can degrade from the bulk and/or from the surface of the dosage form.

Sustained release oral dosage forms can be in any appropriate form for oral administration, such as, for example, in the form of tablets, pills or granules. Granules can be filled into capsules, compressed into tablets or included in a liquid suspension. Sustained release oral dosage forms can additionally include an exterior coating to provide, for example, acid protection, ease of swallowing, flavor, identification, and the like.

In certain embodiments, sustained release oral dosage forms can comprise a therapeutically effective amount of a compound of the invention and a pharmaceutically acceptable vehicle. In certain embodiments, a sustained release oral dosage form can comprise less than a therapeutically effective amount of a compound of the invention and a pharmaceutically effective vehicle. Multiple sustained release oral dosage foams, each dosage form comprising less than a therapeutically effective amount of a compound of the invention, can be administered at a single time or over a period of time to provide a therapeutically effective dose or regimen for treating a disease in a patient associated with a dysfunction in energy metabolism such as, for example, ischemia, oxidative stress, a neurodegenerative disease, including amyotrophic lateral sclerosis (ALS), Huntington's disease, Parkinson's disease or Alzheimer's disease, ischemic reperfusioh injury, a cardiovascular disease, multiple sclerosis (MS), a psychotic disorder, a genetic disease affecting the creatine kinase system or muscle fatigue.

Sustained release oral dosage forms of the invention can release a compound of the invention from the dosage form to facilitate the ability of the compound of the invention to be absorbed from an appropriate region of the gastrointestinal tract, for example, in the small intestine or in the colon. In certain embodiments, a sustained release oral dosage from can release a compound of the invention from the dosage form over a period of at least about 4 hours, at least about 8 hours, at least about 12 hours, at least about 16 hours, at least about 20 hours, and in certain embodiments, at least about 24 hours. In certain embodiments, a sustained release oral dosage form can release a compound of the invention from the dosage form in a delivery pattern of from about 0 wt % to about 20 wt % in about 0 to about 4 hours, about 20 wt % to about 50 wt % in about 0 to about 8 hours, about 55 wt % to about 85 wt % in about 0 to about 14 hours, and about 80 wt % to about 100 wt % in about 0 to about 24 hours. In certain embodiments, a sustained release oral dosage form can release a compound of Formula (I) and/or Formula (II) from the dosage form in a delivery pattern of from about 0 wt % to about 20 wt % in about 0 to about 4 hours, about 20 wt % to about 50 wt % in about 0 to about 8 hours, about. 55 wt % to about 85 wt % in about 0 to about 14 hours, and about 80 wt % to about 100 wt % in about 0 to about 20 hours. In certain embodiments, a sustained release oral dosage form can release a compound of the invention from the dosage form in a delivery pattern of from about 0 wt % to about 20 wt % in about 0 to about 2 hours, about 20 wt % to about 50 wt % in about 0 to about 4 hours, about 55 wt % to about 85 wt % in about 0 to about 7 hours, and about 80 wt % to about 100 wt % in about 0 to about 8 hours.

Sustained release oral dosage forms comprising a creatine prodrug compound of the invention can provide a concentration of creatine in the plasma, blood or tissue of a patient over time, following oral administration to the patient The concentration profile of creatine can exhibit an AUC that is proportional to the dose of the corresponding compound of the invention.

Regardless of the specific form of controlled release oral dosage form used, a compound of the invention can be released from an orally administered dosage form over a sufficient period of time to provide prolonged therapeutic concentrations of the compound of the invention in the plasma and/or blood of a patient. Following oral administration, a dosage form comprising a compound of the invention can provide a therapeutically effective concentration of creatine in the plasma and/or blood of a patient for a continuous time period of at least about 4 hours, of at least about 8 hours, for at least about 12 hours, for at least about 16 hours, and in certain embodiments, for at least about 20 hours following oral administration of the dosage form to the patient. The continuous time periods during which a therapeutically effective concentration of creatine is maintained can be the same or different. The continuous period of time during which a therapeutically effective plasma concentration of creatine is maintained can begin shortly after oral administration or after a time interval.

In certain embodiments, an oral dosage for treating a disease, disorder or condition in a patient can comprise a compound of the invention wherein the oral dosage form is adapted to provide, after a single administration of the oral dosage form to the patient, a therapeutically effective concentration of creatine in the plasma of the patient for a first continuous time period selected from at least about 4 hours, at least about 8 hours, at least about 12 hours, and at least about 16 hours, and at least about 20 hours.

Methods of Use

The creatine kinase (creatine-creatine phosphate) system serves a number of functions in maintaining intracellular energy homeostasis (see e.g., Walsh et al., J Physiol, 2001, 537, 971-978). Phosphocreatine acts as a temporal energy buffer at intracellular sites of high energy translocation which operates when.the rate of ATP utilization is greater than the rate of ATP production by mitochondrial respiration. Mitochondrial creatine kinase allows the high energy phosphate bond of newly synthesized ATP to be transferred to creatine, thus generating phosphocreatine, which is much more stable than ATP. Phosphocreatine can diffuse throughout a cell and its high energy phosphate bond can be used to regenerate ATP from ADP at heavy energy utilization sites where other creatine kinase enzymes are strategically positioned. These sites include membranes that engage in ion transport, axonal regions involved in transporting material along microtubules to and from presynaptic endings, and presynaptic endings where energy is required for neurotransmission. Neurons synthesize creatine, however the amount of creatine can be severely depleted during injury. As with iskeletal and heart muscle, neuronal creatine stores can to some extent be increased by oral supplementation of creatine. The creatine kinase system also serves as an intracellular spatial energy transport mechanism. In this role as an energy carrier, energy generated by the ATP-ADP system within mitochondria is coupled to the creatine-creatine phosphate system in the cytosol, which in turn is coupled to extra-mitochondrial ATP-ADP systems at sites of high intracellular energy transduction. The creatine-creatine phosphate system is also believed to act as a low threshold ADP sensor that maintains ATP-ADP concentration ratios in subcellular locations wherein creatine kinase is functionally coupled to ATP-consuming and ATP-producing pathways. For example, it has been shown that creatine can react with ATP derived from mitochondrial respiration in a reaction catalyzed by mitochondrial creatine kinase and functionally coupled to adenine nucleotide translocase, thereby resulting in an increase in local ADP concentration and the stimulation of mitochondrial respiration. The creatine kinase system is therefore particularly important in maintaining energy homeostasis, including ATP homeostasis, in cells, tissues, and organs with high-energy consumption requirements such as neurons and muscles.

Compounds of the invention and pharmaceutical compositions of the invention can be useful in treating of diseases, disorders or conditions in a patient associated with a dysfunction in energy metabolism. In certain embodiments, the dysfunction in energy metabolism comprises a depletion in intracellular ATP concentration, a decreased intracellular creatine phosphate concentration, a decreased intracellular creatine phosphate to ATP concentration ratio, and/or a dysfunction in the creatine kinase system in a tissue or organ affected by the disease. In certain embodiments, a dysfunction in energy metabolism comprises a decreased intracellular ATP concentration in a tissue or organ affected by the disease. In certain embodiments, a dysfunction in energy metabolism comprises a decreased intracellular creatine phosphate concentration in a tissue or organ affected by the disease. In certain embodiments, the dysfunction in energy metabolism comprises a dysfunction in the creatine kinase system and/or other intracellular energy pathway in a tissue or organ affected by the disease. In certain embodiments, a disease associated with a dysfunction in energy metabolism is selected from ischemia, oxidative stress, a neurodegenerative disease, ischemic reperfusion injury, a cardiovascular disease, multiple sclerosis, a psychotic disease, and muscle fatigue. In certain embodiments, treating a disease comprises effecting energy homeostasis in a tissue or organ affected by the disease.

Compounds of the invention and pharmaceutical compositions, thereof can be used to treat a disease in a.patient associated with oxidative stress by administering to a patient in need of such treatment a therapeutically effective amount of a compound of the invention or a pharmaceutical composition thereof. In certain embodiments, the oxidative stress is associated with ischemia or a neurodegenerative disorder. Methods of the invention include treating an oxidatively stressed tissue or organ by contacting the tissue or organ with a compound of the invention or a pharmaceutical composition thereof.

Compounds and pharmaceutical compositions of the invention can be useful in treating diseases, disorders or conditions in which a rapid increase in intracellular creatine levels has a therapeutic effect.

Ischemia

Compounds and pharmaceutical compositions of the invention can be used to treat acute or chronic ischemic diseases, disorders or conditions. Ischemia is an imbalance of oxygen supply and demand in a cell, tissue or organ. Ischemia is characterized by hypoxia, including anoxia, insufficiency of metabolic substrates for normal cellular bioenergetics, and accumulation of metabolic waste. Ischemia in a tissue or organ may be caused by a vascular insufficiency such as arteriosclerosis, thrombosis, embolism, torsion or compression, hypotension such as shock or hemorrhage, increased tissue mass (hypertrophy), increased workload (tachycardia, exercise), and/or by decreased tissue stress such as cardiac dilation. Ischemia can also result from trauma or surgical procedures. Depending on the severity and duration of the injury, ischemia can lead to a reversible loss of cellular function or to irreversible cell death. Different cell types have different thresholds to ischemic injury depending, at least in part, on the cellular energy requirements of the tissue(s) or organ(s) affected. Parenchymal cells such as neurons (3-4 minutes), cardiac muscles, hepatocytes, renal tubular cells, gastrointestinal epithelium (20-80 minutes) and fibroblasts, epidermis, and skeletal muscle (hours) are more susceptible to ischemic injury than are stromal cells. A number of studies suggest a correlation between the functional capacity of the creatine kinase system and ischemic tolerance of a given tissue, and indicate that strategies toward improving the functional capacity of the creatine kinase system may be effective for improving ischemic tolerance in tissue (see e.g., Wyss and Kaddurah-Daouk, Physiological Reviews, 2000, 80(3), 1107-1213, which is incorporated by reference herein in its entirety). For example oral creatine supplementation inhibits mitochondrial cytochrome C release and downstream caspase-3 activation, resulting in ischemic neuroprotection. Associated with inhibition of cytochrome G release and caspase-3 activation and with neuroprotection, creatine administration inhibits ischemia-mediated ATP depletion.

Compounds and pharmaceutical compositions of the invention can be used to treat acute or chronic ischemia. In certain embodiments, a compound or composition can be particularly useful in acute or emergency treatment of ischemia in tissue or organs characterized by high energy demand such as the brain, neurons, heart, lung, kidney or the intestine.

The high energy requirements compared to the low energy reserves render the brain particularly vulnerable to hypoxic conditions. Although the brain constitutes only a small fraction of total body weight (about 2%), it accounts for a disproportionately large percentage of $O_2$ consumption (about 20%). Under physiological conditions, enhanced demand for $O_2$ is rapidly and adequately compensated for by an increase in cerebral blood flow. The longer the duration of hypoxia/ischemia, the larger and more diffuse the areas of the brain that are affected. The areas most vulnerable to ischemic damage are the brainstem, hippocampus, and cerebral cortex. Injury progresses and eventually becomes irreversible except if oxygenation is not restored. Acute cell death occurs mainly through necrosis but hypoxia also causes delayed apoptosis. In addition glutamate release from presynaptic neurons can further enhance $Ca^{2+}$ influx and result in catastrophic collapse in postsynaptic cells. If the ischemia is not too severe, cells can suppress some functions, i.e., protein synthesis and spontaneous electrical activity, in a process called penumbra, which can be reversed provided that $O_2$ supply is resumed. However, the process of restoring oxygen levels to ischemically stressed tissue, e.g., reperfusion, can also induce irreversible cell death, mainly through the generation of reactive oxygen species and; inflammatory cell infiltration.

The neuron is limited by its availability of energy-generating substrates, being limited to using primarily glucose, ketone bodies or lactate. The neuron does not produce or store glucose or ketone bodies and cannot survive for any significant period of time without a substrate, which is absorbed and used directly or indirectly from the bloodstream. Thus, a constant supply of an energy-generating substrate must be present in the blood at all times in an amount sufficient to supply the entire brain and the rest of the body with energy-generating substrates. Brain cells require a concentration of about 5 mM glucose (or its equivalent) in order to maintain its optimal rate of oxidative phosphorylation to produce ATP. Nutrients enter cells by passing through the cell membrane. Nutrient delivery frequently relies upon mechanisms outside the cell membranes such as oral intake, absorption, circulatory transport and interstitial flux. Once localized in the vicinity of the cell, membrane-specific processes play a role in nutrient transport sequentially across the blood-brain barrier and then into the interior of the cell and into various subcellular organelles. Nutrient transport is made possible by the breakdown of ATP by ATPases. $Na^+$ gradients created by $Na^+/K^+$ ATPases can be used by cells to transport nutrient molecules across cell membranes.

Lack of oxygen or glucose prevents or limits the ability of neurons to synthesize ATP. The intracellular creatine/phosphocreatine system can to some extent compensate for the lack of oxygen or glucose. Creatine kinase catalyses the synthesis of phosphocreatine from creatine in normal brain tissue. Under conditions of ATP depletion, phosphocreatine can donate its phosphate group to ADP to resynthesize ATP. However, neuronal phosphocreatine content is limited following complete anoxia or ischemia phosphocreatine is also rapidly depleted. ATP depletion is believed to block $Na^+/K^+$ ATPases causing neurons to depolarize and lose membrane potential.

Depleted oxygen levels have several other consequences on cellular bioenergetics and function that can ultimately lead to cell death. For example, dysfunctional bioenergetics also involves impaired calcium homeostasis. The regulation of calcium plays a central role in the proper functioning and survival of neurons. Calcium pumps, located on cell membranes, use ATP to transport calcium ions out of the neuron. Proper activity of the calcium pump is essential in the maintenance of neuronal, mitochondrial, and endoplasmic reticulum homeostasis. Alterations in calcium pump function modulate enzyme activity within a cell and also play a critical role in triggering the mitochondrial permeability transition, which may lead to cell death. For example, intracellular $Ca^{2+}$ metabolism is believed to contribute to cell death in Alzheimer's disease. For example, under conditions of oxidative stress, the production of oxygen free radicals exceeds endogenous free radical protective mechanisms. This impairs neuronal metabolism and function by direct free radical damage to important cellular biomolecules including membrane lipids, nucleic acids, and functional proteins; and by modulation of critical signal transduction pathways. Neural function is dependent upon transmission of electrical impulses between cells. This activity relies upon the precise actions of multiple membrane proteins each suspended in a phospholipid bilayer. The optimal activity of this dynamic membrane microenvironment depends upon the exact status and chemical composition of the lipid, constituents. Lacking the appropriate phospholipid environment, cell channel proteins, enzymes, and receptors are not able to achieve sustained levels of optimal function. In addition, oxidative stress and/or abnormal methyl metabolism can reduce the fluidity of the membranous lipid bilayer with subsequent adverse effects upon embedded functional proteins. Dysfunctional bioenergetics may also adversely affect passage of high-energy electrons along the respiratory chain.

Apoptosis refers to the energy-requiring process of programmed cell death whereupon an individual nerve cell under appropriate circumstances initiates a process leading to cell death. Certain of the mechanisms discussed above may initiate apoptotic pathways including oxidative stress, calcium overload, cellular energy deficiency, trophic factor withdrawal, and abnormal amyloid precursor protein processing. In ischemia, neurons in the brain tissue region that are most severely affected by hypoxic injury die rapidly by necrosis, whereas neurons exposed to lesser degrees of hypoxia die by apoptosis. The shift from necrotic cell death to apoptotic cell death is associated with increasing levels of intra cellular ATP. It has been shown that creatine supplementation can result in a greater ability to buffer ATP levels and reduce cell death and thereby provide protection from anoxic and ischemic damage (Balestrino et al., Amino Acids, 2002, 23, 221-229; and Zhu et al., J Neurosci 2004, 24(26), 5909-5912, each of which is incorporated by reference herein in its entirety).

In certain embodiments, compounds and pharmaceutical compositions of the invention can be used to treat a cardiovascular disease, including cerebral ischemia (stroke) and myocardial ischemia (heart infarction). Ischemic heart disease, as the underlying cause of many cases of acute myocardial infarction, congestive heart failure, arrhythmias, and sudden cardiac death, is a leading cause of morbidity and mortality in all industrialized nations. In the United States, ischemic heart disease causes nearly 20% of all deaths (about 600,000 deaths each year) with many of these deaths occurring before the patient arrives at the hospital. An estimated 1.1 million Americans will have a new or recurrent acute myocardial infarction each year, and many survivors will experience lasting morbidity, with progression to heart failure and death. As the population grows older and co-morbidities such as obesity and diabetes become more prevalent, the public health burden caused by ischemic heart disease is likely to increase.

Optimal cellular bioenergetics rely on: (1) adequate delivery of oxygen and substrates to the mitochondria; (2) the oxidative capacity of mitochondria; (3) adequate amounts of high-energy phosphate and the creatine phosphate/ATP ratio; (4) efficient energy transfer from mitochondria to sites of energy utilization; (5) adequate local regulation of ATP/ADP ratios near ATPases; and (6) efficient feedback signaling from utilization sites to maintain energetic homeostasis in the cell. Defects in these cardiac energetic pathways have been found in cardiovascular diseases such as dilated and hypertrophic cardiomyopathies of various origins, cardiac conduction defects, and ischemic heart diseases (Saks et al., J Physiol 2006, 571.2, 253-273; Ventura-Clapier et al., J Physiol 2003, 555.1, 1-13; and Ingwall and Weiss, Circ Res 2004, 95, 135-145, each of which is incorporated by reference herein in its entirety). A decrease in the creatine phosphate/ATP ratio is consistently reported in failing human heart and experimental heart failure, even at moderate workloads. Creatine, creatine transporter, creatine, phosphate, and ATP are significantly reduced and the decrease in the creatine phosphate/ATP ratio is a predictor of mortality in congenital heart failures. Also, a down-regulation of creatine transporter protein expression has been shown in experimental animal models of heart disease, as well as in failing human myocardium, indicating that the generally lowered creatine phosphate and creatine levels measured in failing hearts are related to down-regulated creatine transporter capacity.

Cardiovascular disease includes hypertension, heart failure such as congestive heat failure or heart failure following myocardial infarction, arrhythmia, diastolic dysfunction such as left ventricular diastolic dysfunction, diastolic heart failure or impaired diastolic filling, systolic dysfunction, ischemia such as myocardial ischemia, cardiomyopathy such as hypertrophic cardiomyopathy and dilated cardiomyopathy, sudden cardiac death, myocardial fibrosis, vascular fibrosis, impaired arterial compliance, myocardial necrotic lesions, vascujar damage in the heart, vascular inflammation in the heart, myocardial infarction including both acute post-myocardial infarction and chronic post-myocardial infarction conditions, coronary angioplasty, left ventricular hypertrophy, decreased ejection fraction, coronary thrombosis, cardiac lesions, vascular wall hypertrophy in the heart, endothelial thickening, myocarditis, and coronary artery disease such as fibrinoid necrosis or coronary arteries. Ventricular hypertrophy due to systemic hypertension in association with coronaiy ischemic heart disease is recognized as a major risk factor for sudden death, post infarction heart failure, and cardiac rupture. Patients with severe left ventricular hypertrophy are particularly susceptible to hypoxia or ischemia.

Neuroprotective effects of compounds of the invention can be determined using animal models of cerebral ischemia such as those described, for example, in Cimino et al., Neurotoxicol 2005, 26(5), 9929-33; Konstas et al, Neurocrit Care 2006, 4(2), 168-78; Wasterlain et al., Neurology 1993, 43(11), 2303-10; and Zhu et al., J Neuroscience 2004, 24(26), 5909-5912.

Ischemic Reperfusion Injury

Reperfusion injury is damage to tissue when blood supply returns to the tissue after a period of ischemia. The absence in a tissue or organ of oxygen and nutrients from blood creates a condition in which the restoration of circulation results in inflammation and oxidative damage from the oxygen, rather than restoration of normal function. The damage of ischemic reperfusion injury is due in part to the inflammatory response of damaged tissue. Reperfusion contributes to the ischemic cascade in the brain, which is involved in stroke and brain trauma. Repeated bouts of ischemia and reperfusion also are believed to be a factor leading to the formation and failure to heal of chronic wounds such as pressure sores and diabetic foot ulcers (Mustoe, Am J Surgery 2004, 187(5), S65-S70, which is incorporated by reference herein in its entirety). In certain embodiments, the methods and compositions of the disclosure can protect the muscle and organs such as, for example, the heart, liver, kidney, brain, lung, spleen and steroidogenic organs, e.g. thyroid, adrenal glands, and gonads, from damage as a result of ischemia reperfusion injury.

Ischemia followed by reperfusion is a major cause of skeletal and cardiac muscle damage in mammals. Ischemia is caused by a reduction in oxygen supplied to tissues or organs as a result of reduced blood flow and can lead to organ dysfunction. Reduced blood supply can result from occlusion or blood diversion due to vessel thrombosis, such as myocardial infarction, stenosis, accidental vessel injury or surgical procedures. Subsequent reestablishment of an adequate supply of oxygenated blood to the tissue or organ can result in increased damage, a process known as ischemia reperfusion injury or occlusion reperfusion injury. Complications arising from ischemia reperfusion injury include stroke, fatal or non-fatal myocardial infarction, myocardial remodeling, aneurysms, peripheral vascular disease, tissue necrosis, kidney failure, and post-surgical loss of muscle tone.

Restoration of coronary blood flow following a transient period of ischemia (reperfusion), though necessary for myocyte survival and to restore aerobic metabolism, introduces a separate series of stresses that can exacerbate cell injury. Reactive oxygen species generated during reperfusion damage proteins and membrane structures within cardiomyocytes and can activate signal transduction pathways that lead to apoptosis. Adherence of leukocytes to postischemic endothelial cells can clog capillaries and release inflammatory mediators. Upon reperfusion, the influx of activated complement, catecholamines, and other signaling molecules contained in plasma or elaborated locally within the myocardial wall may also influence the course of events within cells of the myocardium. As with the direct consequences of ischemia, reperfusion injury is an important feature of acute coronary syndromes. Such injury occurs both spontaneously, as a result of fibrinolysis of coronary thromboses, and as a consequence of fibrinolytic drugs of acute angioplasty, treatments that are now commonly used to open occluded vessels.

In certain embodiments, compounds of the invention and compositions thereof can be used to treat a condition associated with ischemic reperfusion injury or reduce ischemic reperfusion injury. Ischemic reperfusion injury can be associated with oxygen deprivation, neutrophil activation, and/or myeloperoxidase production. Ischemic reperfusion injury can be the result of a number of disease states or can be iatrogenically induced, for example, by blood clots, stenosis or surgery.

In certain embodiments, compounds of the invention and compositions thereof can be used to treat stroke, a fatal or non-fatal myocardial infarction, peripheral vascular disease, tissue necrosis, and kidney failure, and post-surgical loss of muscle tone resulting from ischemic reperfusion injury. In certain embodiments, the methods and compositions of the invention reduce or mitigate the extent of ischemic reperfusion injury.

In certain embodiments, compounds of the invention and compositions thereof can be used to treat, reduce or prevent ischemic reperfusion injury associated with occlusion or blood diversion due to vessel stenosis, thrombosis, accidental vessel injury or surgical procedures.

In certain embodiments, compounds of the invention and compositions thereof can also be used to treat any other condition associated with ischemic reperfiision such as myocardial infarction, stroke, intermittent claudication, peripheral arterial disease, acute coronary syndrome, cardiovascular disease and muscle damage as a result of occlusion of a blood vessel.

In certain embodiments, compounds of the invention and compositions thereof can be used to treat reperfusion injury associated with myocardial infarction, stenosis, at least one blood clot, stroke, intermittent claudication, peripheral arterial disease, acute coronary syndrome, cardiovascular disease or muscle damage as a result of occlusion of a blood vessel.

In certain embodiments, compounds of the invention and compositions thereof can be used in conjunction with cardiac surgery, for example, in or with cardioplegic solutions to prevent or minimize ischemia or reperfiision injury to the myocardium. In certain embodiments, the methods and compositions can be used with a cardiopulmonary bypass machine during cardiac surgery to prevent or reduce ischemic reperfusion injury to the myocardium.

In certain embodiments, the methods and compositions of the invention can protect muscle and organs such as, for example, the heart, liver, kidney, brain, lung, spleen and steroidogenic organs, e.g. thyroid, adrenal glands, and gonads, from damage as a result of ischemia reperfusion injury.

Compounds and pharmaceutical compositions of the invention can be used to treat ischemic reperfusion injury in a tissue or organ by contacting the tissue or organ with an effective amount of the compound or pharmaceutical composition. The tissue or organ may be in a patient or outside of a patient, i.e., extracorporeal. The tissue or organ can be a transplant tissue or organ, and the compound or pharmaceutical composition can be contacted with the transplant tissue or organ before removal, during transit, during transplantation, and/or after the tissue or organ is transplanted in the recipient.

In certain embodiments, compounds or pharmaceutical compositions of the invention can be used to treat ischemic perfusion injury caused by surgery, such as cardiac surgery. A compound or pharmaceutical composition can be administered before, during, and/or after surgery. In certain embodiments, a compound or pharmaceutical composition of the invention can be used to treat ischemic reperfusion injury to muscle, including cardiac muscle, skeletal muscle or smooth muscle, and in certain embodiments, to treat ischemic reperfusion injury to an organ such as the heart, lung, kidney, spleen, liver, neuron or brain. A compound of the invention or pharmaceutical composition thereof can be administered before, during, and/or after surgery.

In certain embodiments, compounds of the invention or pharmaceutical compositions of the invention can be used to treat ischemic perfusion injury to a muscle, including cardiac muscle, skeletal muscle, and smooth muscle.

The efficacy of a compound of the invention for treating ischemic reperfusion injury may be assessed using animal models and in clinical trials. Examples of useful methods for assessing efficacy in treating ischemic reperfusion injury are disclosed, for example, in Prass et al., J Cereb Blood Flow Metab 2007, 27(3), 452-459; Arya et al., Life Sci 2006, 79(1), 38-44; Lee et al., Eur. J. Pharmacol 2005, 523(1-3), 101-108; and U.S. Application No. 2004/0038891. Useful methods for evaluating transplant perfusion/reperfusion are described, for example, in Ross et al., Am J. Physiol-Lung Cellular Mol. Physiol. 2000, 279(3), L528-536.

Transplant Perfusion

In certain embodiments, compounds of the invention or pharmaceutical compositions thereof can be used to increase the viability of organ transplants by perfusing the organs with a compound of the invention or pharmaceutical compositions thereof. Increased creatine phosphate levels are expected to prevent or minimize ischemic damage to an organ. Perfusing with a creatine prodrug during organ removal, following removal of a donor organ, during implantation, and/or following organ transplantation, can enhance the viability of the organ, especially a metabolically active organ, such as the heart or pancreas, and thereby reduce rejection rates, and/or increase the time window for organ transplants.

In certain embodiments, compounds of the invention and compositions thereof can be used to treat, prevent or reduce ischemia reperfusion injury in extracorporeal tissue or organs. Extracorporeal tissue or organs are tissue or organs not in an individual (also termed ex vivo), such as in transplantation. For tissue and organ transplantation, donor tissue and organs removed are also susceptible to reperfusion injury during removal, while in transit, during implantation and following transplantation into a recipient. The methods and compositions can be used to increase the viability of a transplantable tissue or organ by, for example, supplementing solutions used to maintain or preserve transplantable tissues or organs. For example, the methods and compositions can be used to bathe the transplantable tissue or organ during transport or can be placed in contact with the transplantable tissue or organ prior to, during or after transplantation.

Neurodegenerative Diseases

Neurodegenerative diseases featuring cell death can be categorized as acute, e.g., stroke, traumatic brain injury, spinal cord injury, and chronic, e.g., amyotrophic lateral sclerosis, Huntington's disease, Parkinson's disease, and Alzheimer's disease. Although these diseases have different causes and affect different neuronal populations, they share similar impairment in intracellular energy metabolism. For example, the intracellular concentration of ATP is decreased, resulting in cystolic accumulation of $Ca^{2+}$ and stimulation of formation of readily oxygen species. $Ca^{2+}$ and reactive oxygen species, in turn, can trigger apoptotic cell death. For these disorders, impairment of brain creatine metabolism is also evident as reflected in decreased total creatine concentration, creatine phosphate concentration, creatine kinase activity, and/or creatine transporter content (see e.g., Wyss and Kaddurah-Daouk, Physiol Rev 2000, 80, 1107-1213; Tarnopolsky and Beai, Ann Neurol 2001, 49, 561-574; and Butterfield and Kanski, Mech Ageing Dev 2001, 122, 945-962, each of which is incorporated by reference herein in its entirety).

Acute and chronic neurodegenerative diseases are illnesses associated with high morbidity and mortality and few options are available for their treatment. A characteristic of many neurodegenerative diseases, which include stroke, brain trauma, spinal cord injury, amyotrophic lateral sclerosis, Huntington's disease, Alzheimer's disease, and Parkinson's disease, is neuronal-cell death. Cell death occurs by necrosis or apoptosis. Necrotic cell death in the central nervous system follows acute ischemia or traumatic injury to the brain or spinal cord. It occurs in areas that are most severely affected by abrupt biochemical collapse, which leads to the generation of free radicals and excitotoxins. Mitochondrial and nuclear swelling, dissolution of organelles, and condensation of chromatin around the nucleus are followed by the rupture of nuclear and cytoplasmic membranes and the degradation of DNA by random enzymatic cuts. Apoptotic cell death can be a feature of both acute and chronic neurological diseases. Apoptosis occurs in areas that are not severely affected by an injury. For example, after ischemia, there is necrotic cell death in the core of the lesion, where hypoxia is most severe, and apoptosis occurs in the penumbra, where collateral blood flow reduces the degree of hypoxia. Apoptotic cell death is also a component of the lesion that appears after brain or spinal cord injury. In chronic neurodegenerative diseases, apoptosis is the predominant form of cell death. In apoptosis, a biochemical cascade activates proteases that destroy molecules required for cell survival and others that mediate a program of cell death. Caspases directly and indirectly contribute to the morphologic changes of the cell during apoptosis (Friedlander, N Engl J Med 2003, 348(14), 1365-75). Oral creatine supplementation has been shown to inhibit mitochondrial cytochrome C release and downstream caspase-3 activation, and ATP depletion inhibition of the caspase-mediated cell death cascades in cerebral ischemia (Zhu et al., J Neurosci 2004, 24(26), 5909-5912) indicating that manipulation of the creatine kinase system may be effective in controlling apoptotic cell death in chronic neurodegenerative diseases.

Creatine administration shows neuroprotective effects, particularly in animal, models of Parkinson's disease, Huntington's disease, and ALS (Wyss and Schulze, Neuroscience 2002, 112(2), 243-260, which is incorporated by reference herein in its entirety) and it is recognized that the level of oxidative stress may be a determinant of metabolic determination in a variety of neurodegenerative diseases. Current hypotheses regarding the mechanisms of creatine-mediated neuroprotection include enhanced energy storage, as well as stabilization of the mitochondrial permeability transition pore by octomeric conformation of creatine kinase. It is therefore believed that higher levels of intracellular creatine improve the overall bioenergetic status of a cell, rendering the cell more resistant to injury.

Parkinson's Disease

Parkinson's disease is a slowly progressive degenerative disorder of the nervous system characterized by tremor when muscles are at rest (resting tremor), slowness of voluntary movements, and increased muscle tone (rigidity). In Parkinson's disease, nerve cells in the basal ganglia, e.g., substantia nigra, degenerate and thereby reduce the production of dopamine and the number of connections between nerve cells in the basal ganglia. As a result, the basal ganglia is unable to smooth muscle movement and coordinate changes in posture, leading to tremor, incoordination, and slowed, reduced movement (bradykinesia) (Blandini, et al., Mol. Neurobiol. 1996, 12, 73.94).

It is believed that oxidative stress may be a factor in the metabolic deterioration seen in Parkinson's disease tissue (Ebadi et al., Prog Neurobiol 1996, 48, 1-19; Jenner and Olanow, Ann Neurol 1998, 44 Suppl 1, S72-S84; and Sun and Chen, J Biomed Sci 1998, 5,401-414, each of which is incorporated by reference herein in its entirety) and creatine supplementation has been shown to exhibit neuroprotective effects (Matthews et al., Exp Neurol, 1999, 157, 142-149, which is incorporated by reference herein in its entirety).

The efficacy of administering a compound of the invention for treating Parkinson's disease may be assessed using animal and human models of Parkinson's disease and clini cal studies. Animal and human models of Parkinson's disease are known (see, e.g., O'Neil et al., CNS Drug Rev. 2005, 11(1), 77-96; Faulkner et al., Ann. Pharmacother. 2003, 37(2), 282-6; Olson et al., Am. J. Med. 1997, 102(1), 60-6; Van Blercom et al., Clin Neuropharmacol. 2004, 27(3), 124-8; Cho et al., Biochem. Biophys. Res. Commun. 2006, 341, 6-12; Emborg, J. Neuro. Meth. 2004, 139, 121-143; Tolwani et al., Lab Anim Sci 1999, 49(4), 363-71; Hirsch et al., J Neural Transm Suppl 2003, 65, 89-100; Orth and Tabrizi, Mov Disord 2003, 18(7), 729-37; Betarbet et al., Bioessays 2002, 24(4), 308-18; and McGeer and McGeer, Neurobiol Aging 2007, 28(5), 639-647).

Alzheimer's Disease

Alzheimer's disease is a progressive loss of mental function characterized by degeneration of brain tissue, including loss of nerve cells and the development of senile plaques and neurofibrillary tangles. In Alzheimer's disease, parts of the brain degenerate, destroying nerve cells and reducing the responsiveness of the maintaining neurons to neurotransmitters. Abnormalities in brain tissue consist of senile or neuritic plaques, e.g., clumps of dead nerve, cells containing an abnormal, insoluble protein called amyloid, and neurofibrillary tangles, twisted strands of insoluble proteins in the nerve cell.

It is believed that oxidative stress may be a factor in the metabolic deterioration seen in Alzheimer's disease tissue with creatine kinase being one of the targets of oxidative damage (Pratico et al., FASEB J 1998, 12, 1777-1783; Smith et al., J Neurochem 1998, 70, 2212-2215; and Yatin et al., Neurochem Res 1999, 24, 427-435, each of which is incorporated by reference herein in its entirety) and studies have shown a correlation between intracellular levels of creatine phosphate and the progress of dementia (Pettegrew et al., Neurobiol Aging 1994, 15, 117-132, which is incorporated by reference herein in its entirety).

The efficacy of administering a compound of the invention for treating Alzheimer's disease may be assessed using animal and human models of Alzheimer's disease and clinical studies. Useful animal models for assessing the efficacy of compounds for treating Alzheimer's disease are disclosed, for example, in Van Dam and De Dyn, Nature Revs Drug Disc 2006, 5, 956-970; Simpkins et al., Ann NY Acad Sci, 2005, 1052, 233-242; Higgins and Jacobsen, Behav Pharmacol 2003, 14(5-6), 419-38; Janus and Westaway, Physiol Behav 2001, 73(5), 873-86; and Conn, ed., "Handbook of Models in Human Aging," 2006, Elsevier Science & Technology.

Huntington's Disease

Huntington's disease is an autosomal dominant neurodegenerative disorder in which specific cell death occurs in the neostriatum and cortex (Martin, N Engl J Med 1999, 340, 1970-80, which is incorporated by reference herein in its entirety). Onset usually occurs during, the fourth or fifth decade of life, with a mean survival at age onset of 14 to 20 years. Huntington's disease is fatal, and there is no effective treatment. Symptoms include a characteristic movement disorder (Huntington's chorea), cognitive dysfunction, and psychiatric symptoms. The disease is caused by a mutation encoding an abnormal expansion of CAG-encoded polyglutamine repeats in the protein, huntingtin. A number of studies, suggest that there is a progressive impairment of energy metabolism, possibly resulting from mitochondrial damage caused by oxidative stress as a consequence of free radical generation. Preclinical studies in animal models of Huntington's disease have documented neuroprotective effects of creatine administration. For example, neuroprotection by creatine is associated with higher levels of creatine phosphate and creatine and reduced lactate levels in the brain, consistent with improved energy production (see, Ryu et al., Pharmacology & Therapeutics 2005, 108(2), 193-207, which is incorporated by reference herein in its entirety).

The efficacy of administering a compound of the invention for treating Huntington's disease may be assessed using animal and human models of Huntington's disease and clinical studies. Animal models of Huntington's disease are disclosed, for example, in Riess and Hoersten, U.S. Application No. 2007/0044162; Rubinsztein, Trends in Genetics, 2002, 18(4), 202-209; Matthews et al., J. Neuroscience 1998, 18(1), 156-63; Tadros et al, Pharmacol Biochem Behav 2005, 82(3), 574-82, and in U.S. Pat. No. 6,706,764, and U.S. Application Nos. 2002/0161049, 2004/0106680, and 2007/0044162. A placebo-controlled clinical trial evaluating the efficacy of creatine supplementation to treat Huntington's disease is disclosed in Verbessem et al., Neurology 2003, 61, 925-230.

Amyotrophic Lateral Sclerosis

Amyotrophic lateral sclerosis (ALS) is a progressive neurodegenerative disorder characterized by the progressive and specific loss of motor neurons in the brain, brain stem, and spinal cord (Rowland and Schneider, N Engl J Med 2001, 344, 1688-1700, which is incorporated by reference herein in its entirety). ALS begins with weakness, often in the hands and less frequently in the feet, that generally progresses up an arm or leg. Over time, weakness increases and spasticity develops characterized by muscle twitching and tightening, followed by muscle spasms and possibly tremors. The average age of onset is 55 years, and the average life expectancy after clinical onset is 4 years. The only recognized treatment for ALS is riluzole, which can extend survival by only about three months. Oral creatine has been shown to provide neuroprotective effects in a transgenic animal model of ALS (Klivenyi et al., Nat Med 1999, 5, 347-50, which is incorporated by reference herein in its entirety).

The efficacy of administering a compound of the invention for treating ALS may be assessed using animal and human models of ALS and clinical studies. Natural disease models of ALS include mouse models (motor neuron degeneration, progressive motor neuropathy, and wobbler) and the hereditary canine spinal muscular atrophy canine model (Pioro and Mitsumoto, Clin Neurosci, 19954996, 3(6), 375-85). Experimentally produced and genetically engineered animal models of ALS can also useful in assessing therapeutic efficacy (see e.g., Doble and Kennelu, Amyotroph Lateral Scler Other Motor Neuron Disord. 2000, 1(5), 301-12; Grieb, Folia Neuropathol. 2004, 42(4), 239-48; Price et al., Rev Neurol (Paris), 1997, 153(8-9), 484-95; and Klivenyi et al, Nat Med 1999, 5, 347-50). Specifically, the SOD1-G93A mouse model is a recognized model for ALS. Examples of clinical trial protocols useful in assessing treatment of ALS are described, for example, in Mitsumoto, Amyotroph Lateral Scler Other Motor Neuron Disord. 2001, 2 Suppl 1, S10-S14; Meininger, Neurodegener Dis 2005, 2, 208-14; and Ludolph and Sperfeld, Neurodegener Dis. 2005, 2(3-4), 215-9.

Multiple Sclerosis

Multiple sclerosis (MS) is a multifaceted inflammatory autoimmune disease of the central nervous system caused by an autoimmune attack against the isolating axonal myelin sheets of the central nervous system. Demyelination leads to the breakdown of conduction and to severe disease with destruction of local axons and irreversible neuronal cell death. The symptoms of MS are highly varied with each individual patient exhibiting a particular pattern of motor, sensible, arid sensory disturbances. MS is typified pathologically by multiple inflammatory foci, plaques of demyelination, gliosis, and axonal pathology witliin the brain and spinal cord, all of which contribute to the clinical manifestations of neurological disability (see e.g., Wingerchuk, Lab Invest 2001, 81, 263-281; and Virley, NeruoRx 2005, 2(4), 638-649). Although the causal events that precipitate the disease are not fully understood, most evidence implicates an autoimmune etiology together with environmental factors, as well as specific genetic predispositions. Functional impairment, disability, and handicap are expressed as paralysis, sensory and octintive disturbances spasticity, tremor, a lack of coordination, and visual impairment, which impact on the quality of life of the individual. The clinical course of MS can vary from individual to individual, but invariably the disease can be categorized in three forms: relapsing-remitting, secondary progressive, and primary progressive. Several studies implicate dysfunction of creatine phosphate metabolism with the etiology and symptoms of the disease (Minderhoud et al., Arch Neurol 1992, 49(2), 161-5; He et al., Radiology 2005, 234(1), 211-7; Tartaglia et al., Arch Neurology 2004, 61(2), 201-207; Duong et al., J Neurol 2007, Apr. 20; and Ju et al., Magnetic Res Imaging 2004, 22, 427-429), although creatine ingestion alone does not appear to be effective in improving exercise capacity in individuals with MS (Lambert et al., Arch Phys Med Rehab 2003, 84(8), 1206-1210).

Assessment of MS treatment efficacy in clinical trials can be accomplished using tools such as the Expanded Disability Status Scale (Kurtzke, Neurology 1983, 33, 1444-1452) and the MS Functional Composite (Fischer et al., Mult Scler, 1.999, 5, 244-250) as well as magnetic resonance imaging lesion load, biomarkers, and self-reported quality of life (see e.g., Kapoor, Cur Opinion Neurol 2006, 19, 255-259). Animal models of MS shown to be useful to identify and validate potential therapeutics include experimental autoimmune/allergic encephalomyelitis (EAE) rodent models that simulate the clinical and pathological manifestations of MS (Werkerle and Kurschus, Drug Discovery Today: Disease Models, Nervous System Disorders, 2006, 3(4), 359-367; Gijbels et al., Neurosci Res Commun 2000, 26, 193-206; and Hofstetter et al., J Immunol 2002, 169, 117-125), and nonhuman primate EAE models ('t Hart et al., Immunol Today 2000, 21, 290-297).

Psychotic Disorders

In certain embodiments, compounds of the invention or pharmaceutical compositions thereof can be used to treat psychotic disorders such as, for example, schizophrenia, bipolar disorder, and anxiety.

Schizophrenia

Schizophrenia is a chronic, severe, and disabling brain disorder that affects about one percent of people worldwide, including 3:2 million Americans. Schizophrenia encompasses a group of neuropsychiatry disorders characterized by dysfunctions of the thinking process, such as delusions, hallucinations, and extensive withdrawal of the patient's interests from other people. Schizophrenia includes the subtypes of paranoid schizophrenia characterized by a preoccupation with delusions or auditory hallucinations, hebephrenic or disorganized schizophrenia characterized by disorganized speech, disorganized behavior, and flat or inappropriate emotions; catatonic schizophrenia dominated by physical symptoms such as immobility, excessive motor activity or the assumption of bizarre postures; undifferentiated schizophrenia characterized by a combination of symptoms characteristic of the other subtypes; and residual schizophrenia in which a person is not currently suffering from positive symptoms, but manifests negative and/or cognitive symptoms of schizophrenia (see DSM-IV-TR classifications 295.30 (Paranoid Type), 295.10 (Disorganized Type), 295.20 (Catatonic Type), 295.90 (Undifferentiated Type), and 295.60 (Residual Type); Diagnostic and Statistical Manual of Mental Disorders, $4^{th}$ Edition, American Psychiatric Association, 297-319, 2005). Schizophrenia includes these and other closely associated psychotic disorders such as schizophreniform disorder, schizoaffective disorder, delusional disorder, brief psychotic disorder, shared psychotic disorder, psychotic disorder due to a general medical condition, substance-induced psychotic disorder, and unspecified psychotic disorders (DSM-IV-TR, $4^{th}$ Edition, pp. 297-344, American Psychiatric Association, 2005).

Schizophrenia symptoms can be classified as positive, negative or cognitive. Positive symptoms of schizophrenia include delusion and hallucination, which can be measured using, for example, the Positive and Negative Syndrome Scale (PANSS) (Kay et al., Schizophrenia Bulletin 1987, 13, 261-276). Negative symptoms of schizophrenia include affect blunting, anergia, alogia and social withdrawal, which can be measured for example, using (the Scales for the Assessment of Negative Symptoms (SANS) (Andreasen, 1983, Scales for the Assessment of Negative Symptoms (SANS), Iowa City, Iowa). Cognitive symptoms of schizophrenia include impairment in obtaining organizing, and using intellectual knowledge which can be measured using the Positive and Negative Syndrome Scale-cognitive subscale (PANSS-cognitive subscale) (Lindenmayer et al., J Nerv Ment Dis 1994, 182, 631-638) or by assessing the ability to perform cognitive tasks such as, for example, using the Wisconsin Card Sorting Test (see, e.g., Green et al., Am J Psychiatry 1992, 149, 162-67; and Koren et al., Schizophr Bull 2006, 32(2), 310-26).

A number of studies support a correlation of schizophrenia with a dysfunction in brain high energy phosphate metabolism (Fukuzako, World J Biol Psychiatry 2001, 2(2), 70-82; and Gangadhar et al., Prog Neuro-Psychopharmacology & Biological Psychiatry 2006, 30, 910-913. Patients suffering from schizophrenia exhibit lower phosphocreatine levels in the left and right frontal regions of the brain, which are highly correlated with hostility-suspiciousness and anxiety-depression assessment subscales (Deicken et al., Biol Psychiatry 1994, 36(8), 503-510; Volz et al., Biol Psychiatry 1998, 44, 399-404; and Volz et al., Biol Psychiatry 2000, 47, 954-961). Creatine supplementation has accordingly been proposed for treating schizophrenia (see e.g., Lyoo et al., Psychiatry Res: Neuroimaging 2003, 123, 87-100).

The efficacy of creatine prodrugs and pharmaceutical compositions thereof for treating schizophrenia may be determined by methods known to those skilled in the art. For example, negative, positive, and/or cognitive symptom(s) of schizophrenia may be measured before and after treatment of the patient. Reduction in such symptom(s) indicates that a patient's condition has improved. Improvement in the symptoms of schizophrenia may be assessed using, for example, the Scale for Assessment of Negative Symptoms (SANS), Positive and Negative Symptoms Scale (PANSS) (see, e.g., Andreasen, 1983, Scales for the Assessment of Negative Symptoms (SANS), Iowa City, Iowa; and Kay et al., Schizophrenia Bulletin 1987, 13, 261-276), and using Cognitive Deficits tests such as the Wisconsin Card Sorting Test (WCST) and other measures of cognitive function (see, e.g., Keshavan et al, Schizophr Res 2004,70(2-3), 187-194; Rush, Handbook of Psychiatric Measures, American Psychiatric Publishing 2000; Sajatovic and Ramirez, Rating Scales in Mental Health, 2nd ed, Lexi-Comp, 2003, Keefe, et al, Schizophr Res. 2004, 68(2-3), 283-97; and Keefe et al, Neuropsychopharmacology, 19 Apr. 2006.

The efficacy of creatine prodrugs and pharmaceutical compositions thereof may be evaluated using animal models of schizophrenic disorders (see e.g., Geyer and Moghaddam, in "Neuropsychopharmacology," Davis et al, Ed, Chapter 50, 689-701, American College of Neuropsychopharmacology, 2002). For example, conditioned avoidance response behavior (CAR) and catalepsy tests in rats are shown to be useful in predicting antipsychotic activity and EPS effect liability, respectively (Wadenberg et al, Neuropsychopharmacology, 2001, 25, 633-641).

Bipolar Disorder

Bipolar disorder is a psychiatric condition characterized by periods of extreme mood. The moods can occur on a spectrum ranging from depression (e.g., persistent feelings of sadness, anxiety, guilt, anger, isolation, and/or hopelessness, disturbances in sleep and appetite, fatigue and loss of interest in usually enjoyed activities, problems concentrating, loneliness, self-loathing, apathy or indifference, depersonalization, loss of interest in sexual activity, shyness or social anxiety, irritability* chronic pain, lack of motivation, and morbid/suicidal ideation) to mania (e.g., elation, euphoria, irritation, and/or suspiciousness). Bipolar disorder is defined and categorized in the Diagnostic and Statistical Manual of Mental Disorders, $4^{th}$ Ed, Text Revision (DSM-IV-TR), American Psychiatric Assoc., 200, pages 382-401. Bipolar disorder includes bipolar I disorder, bipolar II disorder, cyclothymia, and bipolar disorder not otherwise specified.

Patients with bipolar depression are shown to have impaired brain high energy phosphate metabolism characterized by reduced levels of phosphocreatine and creatine kinase (Kato et al, J Affect Disord 1994, 31(2), 125-33; and Segal et al, Eur Neuropsychopharmacology 2007, 17, 194-198) possibly involving mitochondrial energy metabolism (Stork and Renshaw, Molecular Psychiatry 2005, 10, 900-919).

Treatment of bipolar disorder can be assessed in clinical trials using rating scales such as the Montgomery-Asberg Depression Rating Scale, the Hamilton Depression Scale, the Raskin Depression Scale, Feighner criteria, and/or Clinical Global Impression Scale Score (Gijsman et al., Am J Psychiatry 2004, 161, 1537-1547).

Anxiety

Anxiety is defined and categorized in the Diagnostic and Statistical Manual of Mental Disorders, $4^{th}$ Ed., Text Revision (DSM-IV-TR), American Psychiatric Assoc., 200, pages 429-484. Anxiety disorders include panic attack, agoraphobia, panic disorder without agoraphobia, agoraphobia without history of panic disorder, specific phobia, social phobia, obsessive-compulsive disorder, posttraumatic stress disorder, acute stress disorder, generalized anxiety disorder, anxiety disorder due to a general medical condition, substance-induced anxiety disorder, and anxiety disorder not otherwise specified. Recent work has documented a correlation of decreased levels of creatine/phosphocreatine in centrum semiovale (a representative region of the cerebral white matter) with the severity of anxiety (Coplan et al., Neuroimaging, 2006, 147, 27-39).

Useful animal models for assessing treatment of ainxiety include fear-potentiated startle (Brown et al., J Experimental Psychol, 1951, 41,317-327), elevated plus-maze (Pellow et al., J Neurosci. Methods 1985, 14, 149467; and Hogg, Pharmacol Biochem Behavior 1996, 54(1), 21-20), and fear-potentiated behavior in the elevated plus-maze (Korte and De Boer, Eur J Pharmacol 2003, 463, 163-175). Genetic animal models of anxiety are known (Toh, Eur J Pharmacol 2003, 463, 177-184) as are other animal models sensitive to anti-anxiety agents (Martin, Acta Psychiatr Scand Suppl 1998, 393, 74-80).

In clinical trials, efficacy can be evaluated using psychological procedures for inducing experimental anxiety applied to healthy volunteers and patients with anxiety disorders (see e.g., Graeff, et al., Brazilian J Medical Biological Res 2003, 36, 421-32) or by selecting patients based on the Structured Clinical interview for DSM-IV Axis I Disorders as described by First et al., Structured Clinical Interview for DSM-IV Axis I Disorders, Patient Edition (SCIDIP), Version 2. Biometrics Research, New York State Psychiatric Institute, New York, 1995. Any of a number of scales can be used to evaluate anxiety and the efficacy of treatment including, for example, the Penn State Worry Questionnaire (Behar et al., J Behav Ther Exp Psychiatr 2003, 34, 25-43), the Hamilton Anxiety and Depression Scales, the Spielberger State-Trait Anxiety Inventory, and the Liebowitz Social Anxiety Scale (Hamilton, J Clin Psychiatry 1980, 41, 21-24; Spielberger and Vagg, J Personality Assess 1984, 48, 95-97; and Liebowitz, J Clin Psychiatry 1993, 51, 31-35 (Suppl.)).

Genetic Diseases Affecting the Creatine Kinase System

The intracellular creatine pool is maintained by uptake of creatine from the diet and by endogenous creatine synthesis. Many tissues, especially the brain, liver and pancreas, contain the $Na^+$—$Cl^-$ dependent creatine transport ($SLC_6A8$), which is responsible for active creatine transport through the plasma membrane. Creatine biosynthesis involves the action of two enzymes: L-arginine:glycine amidinotransferase (AGAT) and guanidinoacetate transferase (GAMT). AGAT catalyses the transfer of the amidino group of arginine to glycine to generate ornithine and guanidinoacetate. Guanidino acetate is methylated at the amidino group by GAMT to give creatine (see e.g., Wyss and Kaddurah-Daouk, Phys Rev 2000, 80, 1107-213).

In humans, two genetic errors in creatine biosynthesis and one in creatine transporter are known and involve deficiencies of AGAT, GAMT, and creatine transporter (Schulze, Cell Biochem, 2003, 244(1-2), 143-50; Sykut-Cegielska et al., Acta Biochimica Polonica 2004, 51(4), 875-882). Patients with disorders of creatine synthesis have systemic depletion of creatine and creatine phosphate. Patients affected with AGAT deficiency can show mental and motor retardation, severe delay in speech development, and febrile seizures (Item et al., Am J Hum Genet. 2001, 69, 1127-1133). Patients affected with GAMT deficiency can show developmental delay with absence of active speech, autism with self-injury, extra pyramidal symptoms, and epilepsy (Stromberger et al., J Inherit Metab Dis 2003, 26, 299-308). Patients with creatine transporter deficiency exhibit intracellular depletion of creatine and creatine phosphate. The gene encoding the creatine transporter is located on the X-chromosome, and affected male patients show mild to severe mental retardation with affected females having a milder presentation (Salomons et al., J. Inherit Metab Dis 2003, 26, 309-18; Rosenberg et al., Am J Hum Genet. 2004, 75, 97-105; deGrauw et al., Neuropediatrics 2002, 33(5), 232-238; Clark et al., Hum Genet,2006, April).

Creatine supplementation in dosages from about 350 mg to 2 g/kg body weight per day have been shown effective in resolving the clinical symptoms of AGAT or GAMT deficiencies (see e.g., Schulze, Cell Biochem, 2003, 244(1-2), 143-50). However, unlike in patients with GAMT and AGAT deficiency, in patients with creatine transporter deficiency oral creatine supplementation does not result in an increase in brain creatine levels (see Stockler-Ipsiroglu et al, in Physician's Guide to the Treatment and Follow up of Metabolic Diseases, eds Blau et al., Springer Verlag, 2004).

Muscle Fatigue

During high-intensity exercise, ATP hydrolysis is initially buffered by creatine phosphate via the creatine kinase reaction (Kongas and van Beek, $2^{nd}$ Int. Conf. Systems Biol 2001, Los Angeles Calif., Omnipress, Madison, Wis., 193-207; and Walsh et al., J Physiol 2001, 537.3, 971-78, each of which is incorporated by reference herein in its entirety). During exercise, whereas creatine phosphate is available instantaneously for ATP regeneration, glycolysis is induced with a delay of a few seconds, and stimulation of mitochondrial oxidative phosphorylation is delayed even further. Because the creatine phosphate stores in muscle are limited, during high-intensity exercise, creatine phosphate is depleted within about 10 seconds. It has been proposed that muscle performance can be enhanced by increasing the muscle stores of creatine phosphate and thereby delay creatine phosphate depletion. Although creatine and/or creatine phosphate supplementation may improve muscle performance in intermittent, supramaximal exercise, there is no indication that supplementation enhances endurance performance. On the other hand, intravenous injection of creatine phosphate appears to improve exercise tolerance during prolonged submaximal exercise (Clark, J Athletic Train, 1997, 32, 45-51, which is incorporated by reference herein in its entirety).

Muscle Strength

Dietary creatine supplementation in normal healthy individuals has beneficial side effects on muscle function, and as such its use by amateur and professional athletics has increased. There is evidence to suggest that creatine supplementation can enhance overall muscle performance by increasing the muscle store of creatine phosphate, which is the most important energy source for immediate regeneration of ATP in the first few seconds of intense exercise, by accelerating restoration of the creatine phosphate pool during recovery periods, and by depressing the degradation of adenosine nucleotides and possibly also accumulation of lactate during exercise (see e.g., Wyss and Kaddurah-Daouk, Physiol Rev 2000, 80(3), 1107-1213).

However, in normal healthy individuals, the continuous and prolonged use of creatine fails to maintain elevated creatine and creatine phosphate in muscle (see e.g., Juhn et al., Clin J Sport Med 1998, 8, 286-297; Teijung et al., Med Sci Sports Exerc 2000, 32, 706-717; and Vandenberghe et al., J Appl Physiol 1997, 83, 2055-2063, each of which is incorporated by reference herein in its entirety), possibly as a result of the down regulation of the creatine transporter activity and the transporter protein content (Snow and Murphy, Mol Cell Biochem 2001, 224(1-2), 169-181, which is incorporated by reference herein in its entirety). Thus, creatine prodrugs of the invention may be used to maintain, restore, and/or enhance muscle strength in a mammal, and in particular a human.

The efficacy of administering a compound of the invention for maintaining, restoring, and/or enhancing muscle strength may be assessed using animal and human models and clinical studies. Animal models that can be used for evaluation of muscle strength are disclosed, for example, in Wirth et al., J Applied Physiol 2003, 95, 402-412 and Timson, J. Appl, Physiol 1990, 69(6), 1935-1945. Muscle strength can be assessed in humans using methods disclosed, for example, in Oster, U.S. Application No. 2007/0032750, U.S. Application No. 2007/0012105, and/or using other methods known to those skilled in the art.

Organ and Cell Viability

In certain embodiments, the isolation of viable brain, muscle, pancreatic or other cell types for research or cellular transplant can be enhanced by perfusing cells and/or contacting cells with an isolation or growth media containing a creatine phosphate analog prodrug. In certain embodiments, the viability of a tissue organ or cell can be improved by contacting the tissue organ or, cell with an effective amount of a compound of the invention or pharmaceutical composition thereof.

Diseases Related to Glucose Level Regulation

Administration of creatine phosphate reduces plasma glucose levels, and therefore can be useful in treating diseases related to glucose level regulation such as hyperglycemia, insulin dependent or independent diabetes, and related diseases secondary to diabetes (U.S. Application No 2005/0256134).

The efficacy of administering a compound of the invention for treating diseases related to glucose level regulation may be assessed using animal and human models and clinical studies. Compounds can be administered to animals such as rats, rabbits or monkeys, and plasma glucose concentrations determined at various times (see e.g., U.S. Application No. 2003/0232793). The efficacy of compounds for treating insulin dependent or independent diabetes and related diseases secondary to diabetes can be evaluated using animal models of diabetes such as disclosed, for example, in Shafrir, "Animal Models of Diabetes," Ed, 2007, CRC Press; Mordes et al, "Animal Models of Diabetes," 2001, Harwood Academic Press; Mathe, Diabete Metab 1995, 21(2), 106-111; and Rees and Alcolado, Diabetic Med. 2005, 22, 359-370.

Dose

Compounds of the invention) or pharmaceutically acceptable salts or pharmaceutically acceptable solvates of any of the foregoing can be administered to treat diseases or disorders associated with a dysfunction in energy metabolism.

The amount of a compound of the invention that will be effective in the treatment of a particular disease, disorder or condition disclosed herein will depend on the nature of the disease, disorder or condition, and can be determined by standard clinical techniques known in the art. In addition, in vitro or in vivo assays may optionally be employed to help identify optimal dosage ranges. The amount of a compound administered can depend on, among other factors, the patient being treated, the weight of the patient, the health of the patient, the disease being treated, the severity of the affliction, the route of administration, the potency of the compound, and the judgment of the prescribing physician.

For systemic administration, a therapeutically effective dose can be estimated initially from in vitro assays. For example, a dose can be formulated in animal models to achieve a beneficial circulating composition concentration range. Initial doses can also be estimated from in vivo data, e.g., animal models, using techniques that are known in the art. Such information can be used to more accurately determine useful doses in humans. One having ordinary skill in the art can optimize administration to humans based on animal data.

Creatine occurs naturally in the human body and is partly synthesized by the kidney, pancreas, and liver (approximately 1-2 grams per day), and partly ingested with food (approximately 1-5 grams per day). Cells actively take up creatine via the creatine transporter. Within a cell, creatine kinase phosphorylates creatine to form a pool of creatine phosphate that can act as a temporal and spatial energy buffer.

Creatine, creatine phosphate, and analogs thereof can be administered in a high dose without adverse side effects. For example, creatine monohydrate has been administered to athletes and body builders in amounts ranging from 2-3 gm/day, and creatine phosphate has been administered to patients with cardiac diseases by intravenous injection up to 8 gm/day, without adverse side effects. Animals fed a diet containing up to 1% cyclocreatine also do not exhibit adverse effects (see, e.g., Griffiths and Walker, J. Biol. Chem. 1976, 251(7), 2049-2054; Annesley et al., J Biol Chem 1978, 253(22), 8120-25; Lillie et al., Cancer Res 1993, 53, 3172-78; and Griffiths, J Biol Chem 1976, 251(7), 2049-54).

In certain embodiments, a therapeutically effective dose of a compound of the invention can comprise from about 1 mg-equivalents to about 20,000 mg-equivalents of a creatine phosphate analog per day, from about 100 mg-equivalents to about 12,000 mg-equivalents of creatine phosphate analog per day, from about 1,000 mg-equivalents to about 10,000 mg-equivalents of creatine phosphate analog per day, and in certain embodiments, from about 4,000 mg-equivalents to about 8-000 mg-equivalents of creatine phosphate analog per day.

A dose can be administered in a single dosage form or in multiple dosage fowls. When multiple dosage forms are used the amount of compound contained within each dosage form can be the same or different. The amount of a compound of the invention contained in a dose can depend on the route of administration and whether the disease, disorder or condition in a patient is effectively treated by acute, chronic or a combination of acute and chronic administration.

In certain embodiments an administered dose is less than a toxic dose. Toxicity of the compositions described herein can be determined by standard pharmaceutical procedures in cell cultures or experimental animals, e.g., by determining the LD50 (the dose lethal to 50% of the population) or the $LD_{100}$ (the dose lethal to 100% of the population); The dose ratio between toxic and therapeutic effect is the therapeutic index. In certain embodiments, a pharmaceutical composition can exhibit a high therapeutic index. The data obtained from these cell culture assays and animal studies can be used in formulating a dosage range that is not toxic for use in humans. A dose of a pharmaceutical composition of the invention can be within a range of circulating concentrations in for example the blood, plasma or central nervous system, that include the effective dose and that exhibits little or no toxicity. A dose may vary within this range depending upon the dosage form employed and the route of administration utilized.

During treatment, a dose and dosing schedule can provide sufficient or steady state levels of an effective amount of a creatine phosphate analog to treat a disease. In certain embodiments, an escalating dose can be administered.

Administration

A compound of the invention, a pharmaceutically acceptable salt, solvate, tautomer or stereoisomer thereof or a pharmaceutically acceptable solvate of any of the foregoing or a pharmaceutical composition of any of the foregoing can be administered by any appropriate route. In certain embodiments, a compound of the invention can be administered intermittently or continuously. Examples of suitable routes of administration include, but are not limited to, intradermal, intramuscular, intraperitoneal, intravenous, subcutaneous, intranasal, epidural oral, sublingual, intranasal, intracerebral, intravagirial, transdermal, rectally, inhalation or topically. Administration can be systemic or local. Administration can be bolus injection, continuous infusion or by absorption through epithelial or mucocutaneous linings, e.g. oral mucosa, rectal, and intestinal mucosa, etc.

In certain embodiments, it may be desirable to introduce a compound of the invention, a pharmaceutically acceptable salt or a pharmaceutically acceptable solvate of any of the foregoing or a pharmaceutical composition of any of the foregoing directly into the central nervous system by any suitable route, including intraventricular, intrathecal, and epidural injection. Intraventricular injection can be facilitated by the use of an intraventricular catheter, for example, attached to a reservoir, such as an Ommaya reservoir.

In certain embodiments, a compound of the invention, a pharmaceutically acceptable salt, solvate, tautomer or stereoisomer thereof or a pharmaceutically acceptable solvate of any of the foregoing or a pharmaceutical composition of any of the foregoing can be administered parenterally, such as by injection, including, for example, intravenous, intramuscular, intraarterial, intrathecal, intracapsular, intraorbital, intracardiac, intradermal, intraperitoneal, transtracheal, subcutaneous, subcuticular, intraarticualr, subcapsular, subarachnoid, intraspinal, and intrasternal injection or infusion.

A compound of the invention, a pharmaceutically acceptable salt, solvate tautomer or stereoisomer thereof or a pharmaceutically acceptable solvate of any of the foregoing or a pharmaceutical composition of any of the foregoing can be administered systemically and/or locally to a specific organ.

In certain embodiments, a compound of the invention or pharmaceutical composition thereof can be administered as a single, one time dose or chronically. By chronic it is meant that the methods and compositions of the invention are practiced more than once to a given individual. For example, chronic administration can be multiple doses of a pharmaceutical composition administered to an animal, including an individual, on a daily basis, twice daily basis or more or less frequently, as will be apparent to those of skill in the art. In another embodiment, the methods and compositions are practiced acutely. By acute it is meant that the methods and compositions of the invention are practiced in a time period close to or contemporaneous with the ischemic or occlusive event. For example, acute administration can be a single dose or multiple doses of a pharmaceutical composition administered at the onset of an ischemic or occlusive event such as acute myocardial infarction, upon the early manifestation of an ischemic or occlusive event such as, for example, a stroke or before, during or after a surgical procedure. A time period close to or contemporaneous with an ischemic or occlusive event will vary according to the ischemic event but can be, for example, within about 30 minutes of experiencing the symptoms of a myocardial infarction, stroke or intermittent claudication. In certain embodiments, acute administration is administration within about ah hour of the ischemic event. In certain embodiments, acute administration is administration within about 2 hours, about 6 hours, about 10 hours, about 12 hours, about 15 hours or about 24 hours after an ischemic event.

In certain embodiments, a compound of the invention or pharmaceutical composition thereof can be administered chronically. In certain embodiments, chronic administration can include several intravenous injections administered periodically during a single day. In certain embodiments, chronic administration can include one intravenous injection administered as a bolus or as a continuous infusion daily, about every other day, about every 3 to 15 days, about every 5 to 10 days, and in certain embodiments, about every 10 days.

Combination Therapy

In certain embodiments, a compound of the invention, a pharmaceutically acceptable salt, solvate, tautomer or stereoisomer thereof or pharmaceutically acceptable solvate of any of the foregoing, can be used in combination therapy with at least one other therapeutic agent. A compound of the invention and other therapeutic agent(s) can act additively or, and in certain embodiments, synergistically. In some embodiments, a compound of the invention can be administered concurrently with the administration of another therapeutic agent, such as for example, a compound for treating a disease associated with a dysfunction in energy metabolism; treating muscle fatigue; enhancing muscle strength and endurance; increasing the viability of organ transplants; and improving the viability of isolated cells. In some embodiments, a compound of the invention, a pharmaceutically acceptable salt or a pharmaceutically acceptable solvate of any of the foregoing can be administered prior to or subsequent to administration of another therapeutic agent, such as for example, a compound for treating a disease associated with a dysfunction in energy metabolism such as ischemia, ventricular hypertrophy, a neurodegenerative disease such as ALS, Huntington's disease, Parkinson's disease or Alzheimer's disease, surgery related ischemic tissue damage, and reperfusion tissue damage; treating multiple sclerosis (MS), treating a psychotic disorder such as schizophrenia, bipolar disorder or anxiety; treating muscle fatigue; enhancing muscle strength and endurance;, increasing the viability of organ transplants; and improving the viability of isolated cells.

Pharmaceutical compositions of the invention can include, in addition to one or more compounds of the invention, one or more therapeutic agents effective for treating the same or different disease, disorder or condition.

Methods of the invention include administration of one or more compounds or pharmaceutical compositions of the invention and one or more other therapeutic agents provided that the combined administration does not inhibit the therapeutic efficacy of the one or more compounds of the invention and/or does not produce adverse combination effects.

In certain embodiments, compositions of the invention can be administered, concurrently with the administration of another therapeutic agent, which can be part of the same pharmaceutical composition or dosage form as or in a different composition or dosage form from, that containing the compounds of the invention. In certain embodiments, compounds of the invention can be administered prior or subsequent to administration of another therapeutic agent. In certain embodiments of combination therapy, the combination therapy comprises alternating between administering a composition of the invention and a composition comprising another therapeutic agent, e.g., to minimize adverse side effects associated with a particular drug. When a compound of the invention is administered concurrently with another therapeutic agent that potentially can produce adverse side effects including, butnot limited to, toxicity, the therapeutic agent can advantageously be administered at a dose that falls below the threshold at which the adverse side effect is elicited.

In certain embodiments, compounds or pharmaceutical compositions of the invention include or can be administered to a patient together with, another compound for treating Parkinson's disease such as amantadine, benztropine, bromocriptine, levodopa, pergolide, pramipexole, ropinirole, selegiline, trihexyphenidyl or a combination of any of the foregoing.

In certain embodiments, compounds or pharmaceutical compositions of the invention include or can be administered to a patient together with, another compound for treating Alzheimer's disease such as donepezil, galantamine, memantine, rivastigmine, tacrine or a combination of any of the foregoing.

In certain embodiments, compounds or pharmaceutical compositions of the invention include or can be administered to a patient together with, another compound for treating ALS such as riluzole.

In certain embodiments, compounds or pharmaceutical compositions of the invention include or can be administered to a patient together with, another compound for treating ischemic stroke such as aspirin, nimodipine, clopidogrel, pravastatin, unfractionated heparin, eptifibatide, a β-blocker, an angiotensin-converting enzyme (ACE) inhibitor, enoxaparin or a combination of any of the foregoing.

In certain embodiments, compounds or pharmaceutical compositions of the invention include or can be administered to a patient together with, another compound for treating ischemic cardiomyopathy or ischemic heart disease such as ACE inhibitors such as ramipril, captopril, and lisinopril; n-blockers such as acebutolol, atenolol, betaxolol, bisoprolol, carteolol, nadolol, penbutolol, propranolol, timolol, metoprolol, carvedilol, and aldosterone; diuretics; digitoxin or a combination of any of the foregoing.

In certain embodiments, compounds or pharmaceutical compositions of the invention include or can be administered to a patient together with, another compound for treating a cardiovascular disease such as, blood-thinners, cholesterol lowering agents, anti-platelet agents, vasodilators, β-blockers, angiotensin blockers, digitalis and is derivatives or combinations of any of the foregoing.

In certain embodiments, compounds or pharmaceutical compositions of the invention include or can be administered to a patient together with, another compound for treating MS. Examples of drugs useful for treating MS include corticosteroids such as methylprednisolone; IFN-β such as IFN-β1a and IFN-β1b; glatiramer acetate (Copaxone®); monoclonal antibodies that bind to the very late antigen-4 (VLA-4) integrin (Tysabri®) such as natalizumab; immunomodulatory agents such as FTY 720 sphinogosie-1 phosphate modulator and COX-2 inhibitors such as BW755c, piroxicam, and phenidone; and neuroprotective treatments including inhibitors of glutamate excitotoxicity and iNOS, free-radical scavengers, and cationic channel blockers; memantine; AMPA antagonists such as topiramate; and glycine-site NMDA antagonists (Virley, NeruoRx 2005, 2(4), 638-649, and references therein; and U.S. Application No. 2004/0102525).

In certain embodiments, compounds or pharmaceutical compositions of the invention include or can be administered to a patient together with, another compound for treating schizophrenia. Examples of antipsychotic agents useful in treating schizophrenia include, but are not limited to, acetophenazine, alseroxylon, amitriptyline, aripiprazole, astemizole, benzquinamide, carphenazine, chlormezanone, chlorpromazine, chlorprothixene, clozapine, desipramine, droperidol, aloperidol, fluphenazine, flupenthixol, glycine, oxapine, mesoridazine, molindone, olanzapine, ondansetron, perphenazine, pimozide, prochlorperazine, procyclidine, promazine, propiomazine, quetiapine, remoxipride, reserpine, risperidone, sertindole, sulpiride, terfenadine, thiethylperzaine, thioridazine, thiothixene, trifluoperazine, triflupromazine, trimeprazine, and ziprasidone. Other antipsychotic agents useful for treating symptoms of schizophrenia include amisulpride, balaperidone, blonanserin, butaperazine, carphenazine, eplavanserin, iloperidone, lamictal, onsanetant, paliperidone, perospirone, piperacetazine, raclopride, remoxipride, sarizotan, sonepiprazole, sulpiride, ziprasidone, and zotepine; serotonin and dopamine (5HT/D2) agonists such as asenapine and bifeprunox; neurokinin 3 antagonists such as talnetant and osanetant; AMPAkines such as CX-516, galantamine, memantine, modafinil, ocaperidone, and tolcapone; and α-amino acids such as D-serine, D-alanine, D-cycloserine, and N-methylglycine.

In certain embodiments, compounds or pharmaceutical compositions of the invention include or can be administered to a patient together with, another compound for treating bipolar disorder such as aripiprazole, carbamazepine, clonazepam, clonidine, lamotrigine, quetiapine, verapamil, and ziprasidone.

In certain embodiments, compounds or pharmaceutical compositions of the invention include or can be administered to a patient together with, another compound for treating anxiety such as alprazolam, atenolol, busipirone, chlordiazepoxide, clonidine, clorazepate, diazepam, doxepin, escitalopram, halazepam, hydroxyzine, lorazepam, prochlorperazine, nadolol, oxazepam, paroxetine, prochlorperazine, trifluoperazine, and venlafaxine.

EXAMPLES

The following examples describe in detail assays for the characterization of compounds of the invention and uses of compounds of the invention. It will be apparent to those skilled in the art that many modifications, both to materials and methods, may be practiced without departing from the scope of the disclosure.

General Experimental

The NMR spectra of compounds were acquired at 400 or 500 MHz ($^1$H) at 25° C. $^1$H NMR spectra were processed with 0.3 Hz line broadening unless otherwise specified. For LC/MS analysis, a Shimadzu LCMS 2010 (Column: sepax ODS 50×2.0 mm, 5 um), an Agilent 1200 HPLC, 1956 MSP (Column: Waters XBridge C18 4.6×50 mm, 3.5 mm) Shimpack XR-ODS 30×3.0, 2.2 um) operating in ES (+) ionization mode, Agilent 3110™ (or an Agilent Zorbax Bonus RP™, 2.1×50 mm, 3.5 µm, was used. An exemplary set up was at a temperature of 50° C. and at a flow rate of 0.8 mL/min, 2 µL injection, mobile phase: A=water with 0.1% formic acid and 1% acetonitrile, mobile phase B=methanol with 0.1% formic acid; retention time given in minutes. Method details: (I) runs on a Binary Pump G1312B™ with UV/Vis diode array detector G1315C and Agilent 6130™ mass spectrometer in positive and negative ion electrospray mode with UV-detection at 220 and 254 nm with a gradient of 5-95% B in a 2.5 min linear gradient (II) hold for 0.5 min at 95% B (III) decrease from 95-5% B in a 0.1 min linear gradient (IV) hold for 0.29 min at 5% B. For analytical HPLC sample analysis, an Agilent 1200 Series™ was used equipped with a Waters HSS T3™ column, 2.1×50 mm, 1.8 µm, at a temperature of 60° C. and at a flow rate of 0.5 mL/min, mobile phase: A=water with 0.1% formic acid and 0.1% acetonitrile, mobile phase B=acetonitrile with 0.1% formic acid; retention time given in minutes. Melting point temperatures were recorded using a Thomas Hoover Unimelt™ capillary melting point apparatus. Reaction progress was monitored by thin layer chromatography on Merck EMD 60 F254 silica gel coated glass plates using UV light and/or treatment with iodine to visualize. Chromatographic purification was carried out on either a Teledyne ISCO CombiFlash Companion™ with a variable flow rate from 5-100 mL/min. The columns used were Teledyne ISCO RediSep Disposable Flash Columns (4, 12,24,40, 80, or 120 g pre-packed silica gel). Peaks were detected by variable wavelength UV absorption (200-360 nm). Preparative reverse phase chromatography was accomplished using a Gilson 215 Liquid Handler equipped with Varian Model 218 pumps operated using Chromeleon™ software. Detection was achieved using either a Varian Pro Star™ UV-Vis or a Sedex 55™ ELSD unit. Chromatographic separations were achieved using a Phenomenex Kinetex™ 5u C18 100A, Axia, 100×30 mm column at a flow rate of 28 mLmin$^{-1}$.

The compounds tested in the bioassays, such as Compounds A, B, C, D, E, F, G, H, J, K, L, and M, correspond to the compounds exemplified by the synthetic procedures described herein. For example, Compound E is the compound of Example 26, Step 5A as described in this application.

Example 1

Methods foir Determination of Enzymatic Cleavage of Prodrugs In Vitro

For creatine prodrugs, it is generally desirable that the prodrug remains intact (i.e., uncleaved) while in the systemic circulation and be cleaved (i.e., to release the parent drug) in the target tissue. A useful level of stability can at least in part be determined by the mechanism and pharmacokinetics of the prodrug. A useful level of lability can at least in part also be determined by the pharmacokinetics of the prodrug and parent drug (e.g., creatine) in the systemic circulation and/or in the gastrointestinal tract, if orally administered. In general, prodrugs that are more stable in the gastrointestinal tract (as may be assessed by stability in simulated gastric fluid, simulated intestinal fluid, intestinal S9, pancreatin or colonic wash assays) and are more labile in mouse plasma, rat plasma, human plasma, mouse, rat and/or human liver S9, liver microsomes, arid/or hepatocyte preparations can be useful as an orally administered prodrug. In general, prodrugs that are more stable in mouse plasma, rat plasma, human plasma, mouse, rat and/or human liver S9, liver microsomes, and/or hepatocyte preparations and which are more labile in target tissue cell homogenates or target tissue cell isolate preparations, such as brain, muscle, and Caco-2 S9 preparations, can be useful as systemically administered prodrugs and/or can be more effective in delivering a prodrug to a target tissue. In general, prodrugs that are more stable in different pH physiological buffers can be more useful as prodrugs. In general, prodrugs that are more labile in target tissue cell homogenates and/or target tissue cell isolate preparations, such brain, muscle and Caco-2 S9 preparations, can be intra-cellularly cleaved to release the parent drug to a target tissue. The results of tests, such as those described in this example, for determining the enzymatic or chemical cleavage of prodrugs in vitro can be used to select prodrugs for in vivo testing.

The stabilities of prodrugs can be evaluated in one or more in vitro systems using a variety of preparations following methods known in the art. Tissues and preparations are obtained from commercial sources (e.g., Pel-Freez Biologicals, Rogers, Ark., or GenTest Corporation, Woburn, Mass.). Experimental conditions useful for the in vitro studies are described in Table 1. Prodrug is added to each preparation in triplicate.

TABLE 1

Standard[a] Conditions for Prodrug In Vitro Stability and Metabolism Studies

| Assay | Enzyme/Protein *Concentration | Substrate Concentration (µM) | Cofactors |
|---|---|---|---|
| SGF | +/−0.1 mg/mL pepsin | 1-10 | NA |
| SIF | +/−1% w/v pancreatin | 1-10 | NA |
| Plasma | NA | 1-10 | +/− DIFP, 10 mM[d] |
| Blood | NA | 1-10 | +/− DIFP, 10 mM[d] |
| Liver microsomes | 0.5 mg/mL | 1-10 | +/− NADPH[b] |
| Liver or Intestinal S9 | 1 mg/mL | 1-10 | +/− NADPH[b] |
| Hepatocytes | NA | 1-10 | NA |
| Tissue homogenate[c] | NA | 1-10 | NA |

[a]Typical test range provided, range may be exceeded dependent upon intended clinical use of prodrug;
[b]NADPH generating system, e.g., 1.3 mM NADP+, 3.3 mM glucose-6-phosphate, 0.4 U/mL glucose-6-phosphate dehydrogenase, 3.3 mM magnesium chloride and 0.95 mg/mL potassium phosphate, pH 7.4;
[c]Examples;brain tissue homogenate, muscle tissue homogenate;
[d]Assay can be performed with and without addition of diisopropyl fluorophosphonate (DIFP, serine protease inhibitor) to determine if degradation is mediated by a serine protease, e.g., carboxylesterase (CES)

For preparations that contain alkaline phosphatases, prodrug is tested in the presence and absence of a phosphatase inhibitor cocktail (Sigma). Samples are incubated at 37° C. for times ranging from 30 minutes to 24 hours; At each time point, samples are quenched with 50% ethanol. Baseline concentrations of prodrug are determined by adding the compound, directly to the 50% ethanol/preparation mixture (t=0). Samples are centrifuged at 14,000 rpm for 15 minutes, and concentrations of intact prodrug and released parent drug are determined using LC/MS/MS. This stability of prodrugs towards specific enzymes (e.g., peptidases, etc.) is also assessed in vitro by incubation with the purified enzyme.

Pancreatin stability studies are conducted by incubating prodrug (5 µM) with 1% (w/v) pancreatin (Sigma, P-1625, from porcine pancreas) in 0.025 M Tris buffer containing 0.5 M NaCl (pH 7.5) at 37° C. The reaction is stopped by addition of 3 volumes of 50% ethanol. After centrifugation at 14,000 rpm for 15 min, the supernatant is removed and analyzed by LC/MS/MS for prodrug, creatine, and creatinine.

For determination of stability in simulated gastric fluid (SGF), prodrug (10 µM) is incubated in SGF (0.2% NaCl w/v, 0.7% HCl v/v, pH1.2) with and without addition of pepsin (3.2 g of purified pepsin per liter with an activity of 800-2500 units per mg of protein) at 37° C. At selected time points (e.g., 0, 15, 30, 60 and 120 min) 50 µL aliquots are removed and neutralized by addition of 50 µL of 0.1M sodium bicarbonate solution, followed by 150 µL of ice-cold acetonitrile. Samples are centrifuged at 4,000×g for 15 min at 4° C., and the supernatants are removed and analyzed for prodrug, creatine and creatinine concentrations by LC-MSMS (Table 2).

TABLE 2

Stability of Prodrugs Simulated Gastric Fluid (SGF) with and without Pepsin

| Compound ID | Compound of Formula | $T_{1/2}$ (min) (+) pepsin | $T_{1/2}$ (min) (−) pepsin |
|---|---|---|---|
| A | III | 117 | >360 |
| B | III | 133 | >360 |
| C | III | >360 | >360 |
| D | III | >360 | >360 |

TABLE 2-continued

Stability of Prodrugs Simulated Gastric Fluid (SGF) with and without Pepsin

| Compound ID | Compound of Formula | $T_{1/2}$ (min) (+) pepsin | $T_{1/2}$ (min) (−) pepsin |
|---|---|---|---|
| E | III | >360 | >360 |
| F | III | >360 | >360 |
| G | III | >360 | >360 |

For determination of stability in simulated intestinal fluid (SIF), prodrug (10 µM) is incubated in SIF (0.68 % KH$_2$PO4 w/v, 0.86 % NaOH v/v, pH 6.8) with and without addition of pancreatin (1% w/v) at 37° C. At selected time points (e.g., 0, 15, 30, 60 and 120 min) 50 µL aliquots are removed and the reactions are terminated by addition of 150 µL of ice-cold acetonitrile. Samples are centrifuged at 4,000×g for 15 min at 4° C., and the supernatants are removed and analyzed for prodrug, creatine and creatinine concentrations by LC-MSMS (Table 3).

TABLE 3

Stability of Prodrugs Simulated Intesinal Fluid (SIF) with and without Pancreatin

| Compound ID | Compound of Formula | $T_{1/2}$ (min) | |
|---|---|---|---|
| | | (+) pepsin | (−) pepsin |
| A | III | >360 | >360 |
| B | III | >360 | >360 |
| C | III | >360 | >360 |
| D | III | >360 | >360 |
| E | III | >360 | >360 |
| F | III | >360 | >360 |
| G | III | >360 | >360 |

To determine stability in Caco-2 homogertate S9, Caco-2 cells are grown for 21 days prior to harvesting. Culture medium is removed and cell monolayers are rinsed and scraped off into ice-cold 10 mM sodium phosphate/0.15 M potassium chloride, pH 7.4. Cells are lysed by sonication at 4° C. using a probe sonicator. Lysed cells are then transferred into 1.5 mL centrifuge vials and centrifuged at 9,000 g for 20 min at 4° C. The resulting supernatant (Caco-2 cell homogenate S9 fraction) is aliquoted into 0.5 mL vials and stored at −80° C. until used.

For stability studies, prodrug (5 µM) is incubated in Caco-2 homogenate S9 fraction (0.5 mg/mL in 0.1M Tris buffer, pH 7.4) at 37° C. Triplicate samples are quenched at each time point with 50% ethanol. The initial (t=0) concentration of prodrug is determined by adding 5 µM prodrug directly to a 50% ethanol/Caco-2 homogenate mixture. Samples are subjected to LC/MS/MS analysis to determine concentrations of prodrug, creatine and creatinine.

To determine prodrug stability in mouse, rat, human or plasma from other species, prodrugs (10 µM) or positive controls (10 µM, propantheline or procaine) are incubated in undiluted plasma. Duplicate samples of prodrugs and controls are prepared and analyzed. Stock solutions of prodrugs are prepared in DMSO (10 mM) and diluted to 0.1 mM in pH 7.4 phosphate buffer to prepare spiking solutions. The prodrug spiking solutions are aliquoted (10 µL) into 96-well plates. Pre-warmed (37° C.) plasma (90 µL) is added to the wells designated for 5, 15, 30, 45 and 60 min time points; for t=0 min the quench solution (400 µL acetonitrile) is added directly to the prodrug containing well followed by 90 µL of pre-warmed plasma. At 5, 15, 30, 45 and 60 min 400 µL aliquots of acetonitrile are added to the wells to stop the reaction. After quenching, the plates are shaken for 10 min (600 rpm) and then centrifuged at 5500 g for 15 min. Aliquots (50 µL) are transferred to the analysis plate and diluted with 100 µL ultrapure water (Millipore) for LC-MSMS quantitation of prodrug concentrations, and in some cases creatine and/or creatinine. Chromatography columns (e.g., Atlantis HILIC Silica, Gemini C-18, Ultimate XB-C18) are selected based upon the lipophilicity and polarity of each prodrug. LC-MSMS platforms (e.g., Sciex API4000, Sciex API6500) are also selected based on the requirements of each prodrug. The stabilities of the compounds of the present disclosure (prodrugs) in mouse plasma incubations is shown in Table 4 and stability in human plasma incubations is shown in Table 5.

TABLE 4

Stability of Selected Compounds in Mouse Plasma Incubations

| Compound ID | Compound of Formula | % Remaining | | $T_{1/2}$ (min) |
|---|---|---|---|---|
| | | 5 min | 60 min | |
| A | III | 102 | 94.0 | >180 |
| B | III | 110 | 96.0 | >180 |
| C | III | 85.0 | 114 | >180 |
| D | III | 124 | 118 | >180 |
| E | III | 100 | 89.0 | >180 |
| F | III | 103 | 88.2 | 118 |
| G | III | 101 | 91.1 | >180 |
| H | III | 96.6 | 94.5 | >180 |
| J | VI | 53.8 | <LOD | 3.32 |
| K | VI | 37.2 | 0.08 | NC |
| L | I | | | |
| M | I | 97.9 | 101 | >180 |

LOD = Limit of detection

Concentration of compounds (prodrugs) and positive control: 10 µM
Duplicative samples per time point obtained

TABLE 5

Stability of Selected Compounds in Human Plasma Incubations

| Compound ID | Compound of Formula | % Remaining | | $T_{1/2}$ (min) |
|---|---|---|---|---|
| | | 5 min | 60 min | |
| A | III | 105 | 88.8 | >180 |
| B | III | 97.4 | 87.8 | >180 |
| C | III | 86.5 | 119 | 131 |
| D | III | 100 | 109 | 138 |
| E | III | 101 | 75.6 | 154 |
| F | III | 92.7 | 68.1 | >180 |
| G | III | 115 | 90.8 | >180 |
| H | III | 114 | 109 | >180 |
| J | VI | 56.4 | 0.01 | 4.32 |
| K | VI | 42.5 | 0.05 | 3.16 |
| M | I | 96.1 | 91.6 | >180 |

Concentration of compounds (prodrugs) and positive control: 10 µM
Duplicative samples per time point obtained For liver microsomal stability studies, prodrug or positive control (testosterone, propafenone, diclofenac, 7-ethoxycoumarin or propranolol) are incubated (in duplicate) at 5 µM in hepatic or intestinal fractions from mouse, human, dog, monkey and/or rat. Incubations are conducted at 37° C. in the presence or absence of NADPH regenerating system to-indicate whether metabolism proceeds via an NADPH requiring enzyme (i.e. P450s, FMOs, NADPH-P450 reductase or other oxidase enzymes). Duplicate samples of prodrugs and controls are prepared and analyzed. Stock solutions of prodrugs are prepared in DMSO (10 mM) and diluted to 0.05 mM in a mixture of 25% MeOH/pH 7:4 phosphate buffer to prepare spiking solutions. The prodrug spiking solutions are aliquoted (10 µL) into 96-well plates. Pre-warmed (37° C.) microsome solution (80 µL) is added to the wells designated for 5, 15, 30, 45 and 60 min time points and incubated for 10 min before initiating the reaction with 10 pL of NADPH regenerating solution. For t=0 min the quench solution (300 µL acetonitrile) is added directly to the prodrug containing well followed by the microsome solution and NADPH soluton. Incubations of the prodrugs in heat-inactivated fractions or buffer are conducted to differentiate enzymatic from non-enzymatic degradation. At specified time points (e.g., 0, 5, 10, 20, 30 and 60 min), samples are taken and terminated with an equal volume of cold acetonitrile containing a suitable internal standard (e.g., labetalol, tolbutamide). After quenching, the plates are centrifuged at 4000 g for 20 min. Aliquots (100 µL) are transferred to the analysis plate and diluted with 400 µL ultrapure water (Millipore) for LG-MSMS quantitation of prodrug concentrations, and in some cases creatine and/or creatinine. Chromatography columns (e.g., ACE 5 Phenyl, Phenomenex C18 Synergi Hydro-RP, Atlantis HILIC Silica) are selected based upon the lipophilicity and polarity of each prodrug. LC-MSMS platforms (e g-, Sciex API4000, Sciex API6500) are also selected based on the requirements of each prodrug. The metabolic stability of the compounds of the present disclosure of in mouse liver microsomal incubations is shown in Table 6 and human liver microsomal incubations is shown in Table 7.

TABLE 6

Metabolic Stability of Selected Compounds in Mouse Liver Microsomal Incubations

| Compound ID | Compound of Formula | % Remaining (w/ NADPH) 5 min | % Remaining (w/ NADPH) 30 min | % Remaining (No NADPH) 30 min | $T_{1/2}$ (min) | in vivo Clint (ml/min/kg) |
|---|---|---|---|---|---|---|
| A | III | 109 | 112 | 111 | >90 | <71 |
| B | III | 109 | 103 | 99.0 | >90 | <71 |
| C | III | 109 | 112 | 103 | >90 | <71 |
| D | III | 89.3 | 69.5 | 91 | 34.7 | 183 |
| E | III | 89.1 | 26.0 | 15.6 | 20.0 | 407 |
| F | III | 111 | 94.7 | 309 | >90 | <71 |
| G | III | 124 | 96.9 | 223 | >90 | <71 |
| H | III | 126 | 107 | 125 | >145 | <38 |
| J | VI | 25.3 | 0.10 | 1.3 | 4.7 | 1160 |
| L | I | 76.6 | 53.5 | 72.3 | 33.2 | 165 |
| M | I | NA | 41.5 | 52.6 | 19.6 | 280 |

Concentration of compounds (prodrugs) and positive control: 10 µM
Duplicative samples per time point obtained

TABLE 7

Metabolic Stability of Selected Compounds in Human Liver Microsomal Incubations

| Compound ID | Compound of Formula | % Remaining (w/NADPH) 5 min | % Remaining (w/NADPH) 30 min | % Remaining (No NADPH) 30 min | $T_{1/2}$ (min) | in vivo Clint (ml/min/kg) |
|---|---|---|---|---|---|---|
| A | III | 114.2 | 99.2 | 89.0 | >90 | <21 |
| B | III | 96.8 | 85.5 | 91 | >90 | <21 |
| C | III | 112.8 | 76.2 | 103 | 74.4 | 25 |
| D | III | 83.6 | 91.9 | 108 | >90 | 51 |
| E | III | 103.8 | 82.1 | 106 | >90 | <21 |
| F | III | 102.8 | 90.8 | 85.0 | >90 | <21 |
| G | III | 111.2 | 83.0 | 103 | >90 | <21 |
| H | III | 66.5 | 64.9 | 72.4 | 130 | 9.60 |
| J | VI | 38.9 | 1.80 | 5.0 | 11.2 | 111 |
| L | I | 64.5 | 48.1 | 61.1 | 20.9 | 59.8 |
| M | I | 64.1 | 38.8 | 56.0 | 21.5 | 57.9 |

Concentration of compounds (prodrugs) and positive control: 10 µM
Duplicative samples per time point obtained For S9 stability studies, prodrug (5 µM) is incubated in mouse, human, dog, monkey and/or rat liver or intestinal S9 homogenate (0.5 mg/mL in 0.1M potassium phosphate buffer, pH 7.4, 1 mM NADPH) at 37° C. Incubations are conducted in the presence or absence, of NADPH regenerating system to indicate whether metabolism proceeds via an NADPH requiring enzyme (i.e. P450s, FMOs, NADPH-P450 reductase or other oxidase enzymes). Triplicate samples are quenched at each time point with 50% ethanol. The initial (t=0). concentration of prodrug is determined by adding 5 µM prodrug directly to a 50% ethanol/S9 homogenate mixture. Samples are subjected to LC/MS/MS analysis to determine concentrations of prodrug, creatine, and creatinine.

For hepatocyte stability studies, prodrug (5 µM) is incubated with plated hepatocytes (e.g., mouse, rat, human). Fresh hepatocytes are received (Life Technologies) plated in a 12-well format with overlay (except rat which has no overlay). Upon receipt, shipping media is removed immediately and replaced with 1 mL pre-warmed culture medium. Cells are acclimated overnight at 37° C. with 5% CO2 atmosphere. Media is aspirated from the plate and replaced with 1 mL fresh media containing prodrug (5 µM) or solvent control (0.0125% DMSO). Samples (triplicate)are incubated at 37° C. in 5% CO2 atmosphere for 0, 0.25, 0.5, 0.75, 1,2 and 4 hr. Extra wells with solvent control are included for production of calibration curves and measurement of background. At the selected time point, media is removed and frozen. Cells are washed twice with cold PBS. 0.5 mL cold 70% acetonitrile containing internal standard is added to each well and cells are gently removed from the plate by scraping. The recovered cells suspended in the organic solution are aspirated into a vial and frozen at −80° C. For analysis, cell solutions in 70% ACN are removed from the freezer, defrosted and vortexed. 500 µL water is added to each tube and the samples are vortexed again. Tubes are centrifuged at 13000 rpm for 10 minutes at 4° C. Cell supematants and the original recovered media are removed and analyzed by LC-MS/MS for determination of prodrug, creatine, and creatinine.

Three buffers are used to determine the chemical stability of prodrug: (1) 0.1M potassium phosphate, 0.5 M NaCl, pH 2.0, (2) 0.1 M Tris-HCl, 0.5 M NaCl, pH 7.4, and (3) 0.1 M Tris-HCl, 0.5 M NaCl, pH 8.0. Prodrug (5 µM) is added to each buffer in triplicate. Samples are quenched at each time point with 50% ethariol. The initial (t=0) concentration of prodrug is determined by adding 5 µM prodrug directly to a 50% ethanol/pH Buffer mixture. Samples are subjected to LC/MS/MS analysis to determine concentrations of prodrug, creatine and creatinine.

Example 2

In Vitro Determination of Release of Creatine from Prodrugs

For assessment of the ability of prodrugs to release creatine, and to release, creatine preferentially to unwanted cyclization to creatinine, d3-labeled (deuterium labeled methyl group) prodrugs are incubated with liver homogenates (e.g., mouse, human) specially prepared to preserve N-reductase activity. The use of d3-labelled prodrugs is essential in order to distinguish prodrug-derived creatine (d3-creatine) from high concentrations of endogenous (non-labeled) creatine. Incubations (37° C.) are performed in 100 mM potassium phosphate buffer, pH 6.0 to optimize N-reductase activity. Prodrugs are tested at final concentrations of 20 µiM and 200 µM. Approximately 4-5 mg of homogenate is used for each reaction. Co-factor (NADH) is included at a final concentration of 1 mM. Benzamidoxime (500 µM final concentration) is used as a positive control for N-reductase activity. N-reductase activity is confirmed by conversion of benzamidoxime into benzamidine. Negative controls include incubations without NADH (to assess NADH-independent prodrug cleavage) and incubations; without liver homogenate (but with NAPD) to assess non-enzymatic prodrug cleavage under the conditions of the assay. Prodrug incubations are prepared by addition of 10 µL of prodrug stock solution (400 or 4000 µM, 40 % DMSO in water) to 100 µL of the potassium phosphate buffer, followed by addition of 70 µL of liver homogenate. Reaction is initiated by addition of 20 µL of NADH solution (10 mM), or 20 µL water for (-)NADH negative controls. At selected time points (e.g., 0, 30, 60 and 180 min) 50 µL aliquots are removed and the reactions are terminated by addition of 150 µL of ice-cold acetonitrile (80% ACN/20% water) stop solution. The samples are centrifuged at 15890×g for 10 minutes at 4° C., followed by transfer of the supernatants for storage at 40 C pending LC-MSMS analysis. Sample supernatants are analyzed by LC-MSMS (HILIC column) for determination of d3-prodrug, d3-creatine and d3-creatinine levels (Table 8).

Example 3

In Vitro Determination of Caco-2 Cellular Permeability of Prodrugs

The passive permeability of creatine prodrugs is assessed in vitro using standard methods well known in the art (see, e.g., Stewart, et al., Pharm. Res., 1995, 12, 693). For example, passive permeability can be evaluated by examining the flux of a prodrug across a cultured polarized cell monolayer (e.g., Caco-2 cells).

Caco-2 cells obtained from continuous culture (passage less than 28) are seeded at high density onto Transwell polycarbonate filters. Cells are maintained with DMEM/ 10% fetal calf serum+0.1 mM nonessential amino acids+2 mM L-Gln, 5% $CO_2$/95% $O_2$, 37° C. until the day of the experiment. Permeability studies are conducted at pH 6.5 apically (in 50 mM MES buffer containing 1 mM $CaCl_2$, 1 mM MgCl2, 150 mM NaCl, 3 mM KCl, 1 mM $NaH_2PO_4$, 5 mM glucose) and pH 7.4 basolaterally (in Hank's balanced salt solution containing 10 mM HEPES) in the presence of efflux pump inhibitors (250 µM MK-571, 250 µM verapamil, 1 mM Ofloxacin). Inserts are placed in 12 or 24 well plates containing buffer and incubated for 30 min at 37° C. Prodrug (100 µM, 250 µM, 300 µM or 500 µM) is added to the apical or basolateral compartment (donor) and concentrations of prodrug and/or released parent drug (creatine) in the opposite compartment (receiver) are determined at intervals over 1 hour using LC/MS/MS. Values of apparent permeability ($P_{app}$) are calculated using the equation:

$$P_{app} = V_t(dC/dt)/(AC_o)$$

where $V_t$ is the volume of the receiver compartment in mL; dC/dt is the total flux of prodrug and parent drug (µM/s), determined from the slope of the plot of concentration in the receiver compartment versus time; $C_o$ is the initial concentration of prodrug in µM; and A is the surface area of the membrane in $cm^2$. In certain embodiments, prodrugs with significant transcellular permeability exhibit a value of $P_{app}$

TABLE 8

In Vitro Release of d3-Creatine and d3-Creatinine from d3-Prodrugs in Mouse Liver Homogenate (MLH) Incubations

| Compound ID | Compound of Formula | Incubation Conditions | Concentration (µM) at 120 min | | |
|---|---|---|---|---|---|
| | | | Prodrug | d3-Creatine | d3-Creatinine |
| A | III | Prodrug + MLH + NADH | 195 | 45.4 | ND |
| | | Negative Control (No NADH) | 254 | 15.0 | ND |
| | | Negative Control (No MLH) | 361 | 0.29 | ND |
| E | III | Prodrug + MLH + NADH | 4.70 | 39.1 | ND |
| | | Negative Control (No NADH) | ND | 10.0 | ND |
| | | Negative Control (No MLH) | 240 | ND | ND |
| F | III | Prodrug + MLH + NADH | 157 | 9.68 | 19.9 |
| | | Negative Control (No NADH) | 176 | 2.25 | 4.52 |
| | | Negative Control (No MLH) | 259 | ND | ND |

ND = not determined of ≥1×10⁻⁶ cm/s, in certain embodiments, a value of $P_{app}$ of ≥1×10⁻⁵ cm/s, and in certain embodiments a value of $P_{app}$ of ≥5×10⁻⁵ cm/s.

Example 4

Uptake by Caco-2 and HEK-2 Cells

Caco-2 or HEBC Peaks are seeded onto poly-lysine coated 24-well plastic cell culture plates at 250,000 and 500,000 cells/well, respectively. Cells are incubated overnight at 37° C. Prodrug is added to each well in 1 mL fresh media. Each concentration of prodrug is tested in triplicate. Media only is added to the control wells. At each time point, cells are washed four times in Hank's Balanced Salt Solution. Cells are lysed and compound is extracted by adding 200 μL 50% ethanol to each well for 20 minutes at room temperature. Aliquots of the ethanol solution are moved to a 96-well V-bottom plate and centrifuged at 5,700 rpm for 20 minutes at 4° C. Supernatant is analyzed by LC/MS/MS to determine the concentration of prodrug, creatine, and/or creatinine.

Example 5

Expression of SMVT in Mammalian Cells

Sodium dependent multivitamin transporter (SMVT; product of the $SLC_5A6$ gene) was subcloned into a plasmid that allows for inducible expression by tetracycline (TREX plasmid, Invitrogen Inc., Carlsbad Calif.). The SMVT expression plasmid was transfected into a human embryonic kidney (HEK) cell line and stable clones were isolated by G418 selection arid flow activated cell sorting (FACS). Biotin uptake in a SMVT-HEK cell clone was used for validation. SMVT-HEK/TREX cells were plated in 96-well plates at 100,000 cells/well at 37° C. for 24 hours and tetracycline (1 μg/mL), was added to each well for an additional 24 hours to induce SMVT transporter expression. Radiolabeled ³H-biotin (about 100,000 cpm/well) was added to each well. Plates were incubated at room temperature for 10 min. Excess ³H-biotin was removed and cells were washed three times with a 96-well plate washer with cold assay buffer. Scintillation fluid was added to each well, and the plates were sealed and counted in a 96-well plate-based scintillation counter.

Similar methods can be used to prepare HEK cells expressing other transporters or other cell lines expressing SMVT or other transporters.

The GenBank accession number for human SMVT is NM.021095, which is incorporated by reference herein. Reference to the SMVT transporter includes the amino acid sequence described in or encoded by the GenBank reference number NM.021095, and, allelic, cognate and induced variants and fragments thereof retaining essentially the same transporter activity. Usually such variants show at least 90% sequence identity to the exemplary GenBank nucleic acid or amino acid sequence. Substrates for SMVT are compounds containing a free carboxylic acid and a short alkyl chain, e.g., $C_{1-6}$ alkyl, ending in a cyclic or branched group. Example of SMVT substrates include biotin, pantothenic acid, and 4-phenylbutyric acid.

Example 6

Competition Assays Using SMVT

To determine if a creatine prodrug binds the SMVT transporter, a competition binding assay was developed. This assay measures how different concentrations of a test compound block the uptake of a radiolabeled substrate such as biotin or pantothenic acid. The half-maximal inhibitory concentration ($IC_{50}$) for inhibition of transport of a substrate by a test compound is an indication of the affinity of the test compound for the SMVT transporter. If the test compound binds SMVT competitively with the radiolabeled substrate, less of the radiolabeled substrate is transported into the HEK cells. For test compounds that do not interact with SMVT in a manner competitive with substrates the curve remains an essentially flat line, i.e., there is no dose response seen. The amount of radiolabeled substrate taken up by the cells is measured by lysing the cells and measuring the radioactive counts per minute. Competition binding studies are performed as follows. SMVT-HEK/TREX cells are plated in 96-well plates at 100,000 cells/well at 37° C. for 24 hours and tetracycline (1 μg/mL) is added to each well for an additional 24 hours to induce SMVT transporter expression. Radiolabeled ³H-biotin (about 100,000 cpm/well) is added to each well in the presence and absence of various concentrations of unlabeled biotin or pantothenic acid in duplicate or triplicate. Plates are incubated at room temperature for 10 min. Excess ³H-biotin is removed and cells are washed three times using a 96-well plate washer with cold assay buffer. Scintillation fluid is added to each well, and the plates are sealed and counted in a 96-well plate-based scintillation counter. Data is graphed and analyzed using non-linear regression analysis with Prism Software (GraphPad, Inc., San Diego, Calif.).

Example 7

Treatment of HEK SMVT Cells with Creatine Prodrugs

Uptake, of unlabeled creatine prodrugs is measured in HEK cells stably expressing SMVT. Cells are plated at a density of 250,000 cells/well in polylysine coated 24-well tissue culture plates. Twenty-four hours later cells are treated with tetracycline (1 μg/ml) to induce SMVT expression or left untreated. The following day (approximately 48 hours after seeding), the assay is performed. Creatine prodrugs (0.1 mM final concentration) are added to a buffered saline solution (HBSS), and 0.5 mL of each test solution is added to each well. Cells are allowed to take up the test compounds for 1 or 3 hours. Test solution is aspirated and cells washed 4 times with ice-cold HBSS. Cells are then lysed with a 50% ethanol solution (0.2 mL/well) at room temperature for 15 minutes. The lysate is centrifuged at 5477×g for 15 minutes at 4° C. to remove cell debris. The concentration of creatine prodrugs and creatine in the cell is determined by analytical LC/MS/MS. Transporter specific uptake is determined by comparison with control cells lacking transporter expression.

Example 8

Effect of Treatment on the Creatine Kinase System

HEK cells expressing SMVT are treated with buffer, a creatine prodrug (100 μM), creatine (100 μM) or creatine analog (100 μM), for a specified time period according to the protocol of Example 6. Following treatment, the intracellular concentrations of the creatine: prodrug, creatine phosphate, ATP, and creatine and/or creatine analog are measured by analytical LC/MS/MS.

Example 9

Restoration of Cellular Energy Homeostasis Following Sodium Azide Treatment An adaptation of the methods described by Weinstock and Shoham, Neural Transm. 2004, 111(3), 347-66, is used to evaluate the protective effects on intracellular energy homeostasis of compounds of the invention.

The HEK TREX SMVT cell line is seeded at 250 k per well in a 24-well polylysine coated tissue culture plate. The next day, cells are treated with doxycycline (1 µg/mL) to express the SMVT transporter, which is required for efficient uptake of the creatine prodrug, e.g., a compound of the invention, tested. The cells are incubated and assayed on the following day. Cells are washed twice with HBSS buffer lacking glucose. Cells are then incubated for 20 mM at 37° C. in a 5% $CO_2$ incubator in the same buffer with or without sodium azide. A typical range of sodium azide used in these experiments is from 1 mM to 9 mM. After this time, 300 µM of a prodrug of a creatine analog is added to the cells or the cells are left untreated. In some experiments, creatine is used as a comparison. The cells are incubated for an additional 20 min and then washed with buffer. Samples are extracted for 15 min with 50% ethanol and processed for LC/MS/MS to detect the creatine prodrug, creatine, and ATP levels. Increased creatine phosphate and ATP levels in sodium azide treated cells following exposure to a creatine prodrug indicates that the prodrug is capable of restoring cellular energy homeostasis.

Example 10

Protection Against 3-Nitropropionic Acid Induced Toxicity

An adaptation of the methods described by Brouillet et al., J. Neurochem 2005, 95(6), 1521-40, is used to evaluate the protective effects on intracellular energy homeostasis of compounds of the invention.

The rat cardiomyoblast cell line H9c2 is obtained from ATCC (#CRL-1446). A 20 mM stock solution of 3-nitropropionic acid (3-NP) is prepared immediately before use in normal media (DMEM/High glucose (4.5 g/L)/10% FBS/6 mM L-glutamine/PSF) and the pH is adjusted to 7.4 by dropwise addition of IN sodium hydroxide. A 40 mM stock solution of a creatine prodrug, e.g. a compound of the invention, is prepared in DMSO, and creatine is dissolved directly in serum-free media at 10 mM.

To measure the extent of cellular protection provided by the creatine prodrug and/or a creatine analog against 3-NP toxicity, H9c2 cells are plated in 96-well clear-bottom black tissue culture plates at 10K cells per well in normal media and incubated overnight at 37° C. The following day the media is removed and replaced with serum-free media containing serial dilutions of a creatine prodrug or creatine. The plates are incubated at 37° C. for 2 hours. Media is then removed by aspiration and replaced with normal, media containing various concentrations of 3-NP and the plates incubated at 37° C. for an additional 20 hours. To determine the number of viable cells in each well, an equal volume of CellTiter-Glo reagent (Promega) is added and mixed for 10 minutes on a plate shaker at room temperature. Luminescence is measured by reading the plates in a luminometer. The luminescence produced in this assay is proportional to the amount of ATP present, and directly relates to the number of metabolically active cells.

Increased viability of cells exposed to 3-NP and a creatine prodrug compared to that of cells exposed to 3-NP and creatine indicates that the creatine prodrug has the capacity to maintain cellular energy homeostasis.

Example 11

Pharmacokinetics of Creatine Prodrugs Following Colonic Administration in Rats Sustained release oral dosage forms, which release drug slowly over periods of about 6 to about 24 hours, generally release a significant proportion of the dose within the colon. Thus, drugs suitable for use in such dosage forms should be colonically absorbed. This experiment is performed to assess the uptake and resultant levels of a creatine prodrug and creatine in a biological fluid such as the plasma/blood or cerebrospinal fluid (CSF), following intracolonic administration of a corresponding creatine prodrug, such as a compound of the invention and thereby determine the suitability of a creatine prodrug for use in an oral sustained release dosage faun. Bioavailability of a creatine prodrug and creatine following co-administration of the creatine prodrug can be calculated relative to oral administration and/or to colonic administration of the creatine prodrug.

Step A: Administration Protocol

Rats are obtained commercially and are pre-cannulated in both the ascending colon and the jugular vein. Animals are conscious at the time of the experiment. All animals are fasted overnight and until 4 hours post-dosing of a creatine prodrug. The creatine prodrug is administered as a solution (in water or other appropriate solvent and vehicles) directly into the colon via the cannula at a dose equivalent to about 1 mg to about 200 mg of the creatine prodrug per kg body weight. Blood samples (0.3 mL) are obtained from the jugular cannula at intervals over 8 hours and are immediately quenched with sodium metabisulfite or other appropriate antioxidant to prevent oxidation of the creatine prodrug. Blood samples can be further quenched with methanol/perchloric acid to prevent post-sampling hydrolysis of the creatine prodrug. Blood samples are analyzed as described below. Samples can also be taken from the GSF or other appropriate biological fluid.

Step B: Sample Preparation for Colonically Absorbed Prodrug

Methanol/perchloric acid (300 µL) is added to blank 1.5 mL Eppendorf tubes. Rat blood (300 µL) is collected into EDTA tubes containing 75 µL of sodium metabisulfite at different times and vortexed to mix. A fixed volume of blood (100 µL) is immediately added into the Eppendorf tube and vortexed to mix. Ten microliters of a standard stock solution of the creatine prodrug (0.04, 0.2, 1, 5, 25, and 100 µg/mL) and 10 µL of the 10% sodium metabisulfite solution are added to 80 pL of blank rat blood to make up a final calibration standard (0.004, 0.02, 0.1, 0.5, 2.5, and 10 µg/mL). Methanol/perchloric acid (300 µL of 50/50) is then added into each tube followed by the addition of 20 µL of p-chlorophenylalanine. The samples are vortexed and centrifuged at 14,000 rpm for 10 min. The supernatant is analyzed by LC/MS/MS.

Step C: LC/MS/MS Analysis

An API 4000 LC/MS/MS spectrometer equipped with Agilent 1100 binary pumps, a CTC HTS-PAL autosampler, and a Zorbax XDB C8 4.6×150 mm column is used during the analysis. Appropriate mobile phases can be used such as, for example, (A) 0.1% formic acid, and (B) acetonitrile with 0.1% formic acid. Appropriate gradient conditions can be used such as, for example: 5% B for 0.5 min, then to 98% B in 3 min, maintained at 98% B for 2.5 min, and then returned to 2% B for 2 min. A TurboIonSpray source is used on the API 4000. The analysis is done in an appropriate ion mode and the MRM transition for each analyte is optimized using standard solution. 5 µL of each sample is injected. Non-compartmental analysis is performed using WinNonlin software (v.3.1 Professional Version, Pharsight Corporation, Mountain View, Calif.) on individual animal profiles. Summary statistics on. major parameter estimates is performed for $C_{max}$ (peak observed concentration following dosing), $T_{max}$ (time to maximum concentration is the time at which the peak concentration is observed), $AUC_{(0-t)}$ (area under the serum concentration-time curve from time zero to last collection time, estimated using the log-linear trapezoidal method), $AUC_{(0-infin)}$ (area under the blood concentration time curve from time zero to infinity, estimated using the log-linear trapezoidal method to the last collection time with extrapolation to infinity), and $t_{1/2}$,z (terminal half-life).

The pharmacokinetic parameters of the creatine prodrug and creatine following colonic administration of the corresponding creatine prodrug are determined and compared to those obtained following an equivalent colonic dose of the creatine prodrug. Maximum concentrations of the creatine prodrug and creatine in the blood ($C_{max}$ values) and the area under blood concentration versus time curve (AUC) values after intra-colonic dosing of a creatine prodrug that are higher than those achieved for colonic administration of the corresponding creatine prodrug indicate that the prodrug provides enhanced colonic bioavailability.

Example 12

Pharmacokinetics of a Creatine Prodrug Following Intravenous or Oral Administration to Rats A creatine prodrug is administered as an intravenous bolus injection or by oral gavage to groups of four to six adult male Sprague-Dawley rats (about 250 g). Animals are conscious at the time of the experiment. When orally administered, the creatine prodrug is administered as an aqueous solution (or as a solution of another appropriate solvent optionally including appropriate vehicles) at an appropriate creatine prodrug dose equivalent per kg body weight Blood samples (0.3 mL) are obtained via a jugular vein cannula at intervals over 8 hours following oral dosing. Blood is quenched immediately using, for example, acetonitrile with 1% formic acid and then is frozen at ±80° C. until analyzed. Samples may also be taken form the CSF or other appropriate biological fluid.

Three hundred (300) µL of 0.1% formic acid in acetonitrile is added to blank 1.5 mL tubes. Rat blood (300 µL) is collected at different times into tubes containing EDTA and vortexed to mix. A fixed volume of blood (100 µL) is immediately added into the tube and vortexed to mix. Ten microliters of a creatine prodrug standard stock solution (0.04, 0.2,1, 5,25, and 100 µg/mL) is added to 90 µL of blank rat blood quenched with 300 µL of 0.1% formic acid in acetonitrile. Then, 20 µL of p-chlorophenylalanine is added to each tube to make a final calibration standard (0.004, 0.02, 0.1, 0.5, 2.5, and 10 µg/mL). Samples are vortexed and centrifuged at 14,000 rpm for 10 min. The supernatant is analyzed by LC/MS/MS.

An API 4000 LC/MS/MS spectrometer equipped with Agilent 1100 binary pumps, a CTC HTS-PAL autosampler, and a Phenomenex Synergihydro-RP 4.6×30 mm column are used in the analysis. Appropriate mobile phases and gradient conditions are used for the analysis. The analysis is done in the appropriate ion mode and the MRM transition for each analyte is optimized using standard solutions. Five (5) µL of each sample is injected. Non-compartmental analysis is performed using WinNonlin (v.3.1 Professional Version, Pharsight Corporation, Mountain View, Calif.) on individual animal profiles. Summaiy statistics on major parameter estimates is performed for $C_{max}$ (peak observed concentration following dosing), $T_{max}$ (time to maximum concentration is the time at which the peak concentration was observed), $AUC_{(0-t)}$ (area under the serum concentration-time curve from time zero to last collection time, estimated using the log-linear trapezoidal method); $AUC_{(0-infin)}$, (area under the serum concentration time curve from time zero to infinity, estimated using the log-linear trapezoidal method to the last collection time with extrapolation to infinity), and $t_{1/2}$ (terminal half-life).

The oral bioavailability (F(%)) of the creatine prodrug is determined by comparing the area under the creatine prodmg concentration vs time curve (AUC) following oral administration with the AUC of the creatine prodrug concentration vs time curve following intravenous administration of the creatine prodrug on a dose normalized basis.

Samples can also be obtained from the CSF and the pharmacokinetics of the creatine prodrug and creatine determined. Higher levels of creatine prodrug and/or creatine can indicate that the prodrug has the ability to be translocated across the blood-brain barrier.

Similar studies on the pharmacokinetics of a creatine prodrug can be performed in other animals including but not limited to dogs, monkeys, and human.

Example 13

Use of Animal Models to Assess the Efficacy of Creatine Prodrugs for Treating Amyotrophic Lateral Sclerosis A murine model of SOD1 mutation-associated ALS has been developed in which mice express the human superoxide dismutase (SOD) mutation glycine.fwdarw.alanine at residue 93 (SOD1). These SOD1 mice exhibit a dominant gain of the adverse property of SOD, and develop motor neuron degeneration and dysfunction similar to that of human ALS (Gurney et al, Science 1994, 264(5166), 1772-1775; Gurney et al., Ann. Neurol. 1996, 39, 147-157; Gurney, J. Neurol. Sci. 1997, 152, S67-73; Ripps et al., Proc Natl Acad Sci U.S.A. 1995, 92(3), 689-693; and Bruijn et al., Proc Natl Acad Sci U.S.A. 1997, 94(14), 7606-7611). The SOD1 transgenic mice show signs of posterior limb weakness at about 3 months of age and die at 4 months. Features common to human ALS include astrocytosis, microgliosis, oxidative stress, increased levels of cyclooxygenase/prostaglandin, and as the disease progresses, profound motor neuron loss.

Studies are performed on transgenic mice overexpressing human Cu/Zn-SOD G93A mutations (B6SJL-TgN(SOD1-G93A) 1 Gur) and non-transgenic B6/SJL mice and their wild litter mates. Mice are housed on a 12-hr day/light cycle and (beginning at 45 d of age) allowed ad libitum access to either test compound-supplemented chow or as a control, regular formula cold press chow processed into identical pellets. Genotyping can be conducted at 21 days of age as described in Gurney et al., Science 1994, 264(5166), 1772-1775. The SOD1 mice are separated into groups and treated with a test compound or serve as controls.

The mice are observed daily and weighed weekly. To assess health status mice are weighed weekly and examined for changes in lacrimation/salivation, palpebral closure, ear twitch and pupillary responses, whisker orienting, postural and righting reflexes and overall body condition score. A general pathological examination is conducted at the time of sacrifice.

Motor coordination performance of the animals can be assessed by one or more methods known to those skilled in the art. For example, motor coordination can be assessed using a neurological scoring method. In neurological scoring, the neurological score of each limb is monitored and recorded according to a defined 4-point scale: 0=normal reflex on the hind limbs (animal splays its hind limbs when lifted by its tail); 1=abnormal reflex of hind limbs (lack of splaying of hind limbs when animal is lifted by the tail); 2=abnormal reflex of limbs and evidence of paralysis; 3=lack of reflex and complete paralysis; and 4=inability to right when placed on the side in 30 seconds or found dead. The primary end point is survival with secondary end points of neurological score and body weight. Neurological score observations and body weight are made and recorded five days per week. Data analysis is performed using appropriate statistical methods.

The rotarod test evaluates the ability of an animal to stay on a rotating dowel allowing evaluation of motor coordination and proprioceptive sensitivity. The apparatus is a 3 cm diameter automated rod turning at, for example, 12 rounds per min. The rotarod test measures how long the mouse can maintain itself on the axle without falling. The test can be stopped after an arbitrary limit of, for example, 120 sec. If the animal falls before 120 sec, the performance is recorded and two additional trials are performed. The mean time of 3 trials is calculated. A motor deficit is indicated by a decrease of walking time.

In the grid test, mice are placed on a grid (length: 37 cm, width: 10.5 cm, mesh size: 1×1 $cm^2$) situated above a plane support. The number of times the mice put their paws through the grid is counted and serves as a measure for motor coordination.

The hanging test evaluates the ability of the animal to hang on a wire. The apparatus is a wire stretched horizontally 40 cm above a table. The animal is attached to the wire by its forepaws. The time needed by the animal to catch the string with its hind paws is recorded (60 sec max) during three consecutive trials.

Electrophysiological measurements (EMG) can also be used to assess motor activity condition. Electromyographic recordings are performed using an electromyography apparatus. During EMG monitoring the mice are anesthetized. The measured parameters are the amplitude and the latency of the compound muscle action potential (CMAP). CMAP is measured in gastrocnemius muscle after stimulation of the sciatic nerve. A reference electrode is inserted near the Achilles tendon and an active needle placed at the base of the tail. A ground needle is inserted on the lower back of the mice. The sciatic nerve is stimulated with a single 0.2 msec pulse at supramaximal intensity (12.9 mA). The amplitude (m V) and the latency of the response (ms) are measured. The amplitude is indicative of the number of active motor units, while distal latency reflects motor nerve conduction velocity.

The efficacy of test compounds can also be evaluated using biomarker analysis. To assess the regulation of protein biomarkers in SOD I mice during the onset of motor impairment, samples of lumbar spinal cord (protein extracts) are applied to ProteinChip Arrays with varying surface chemical/biochemical properties and analyzed, for example, by surface enhanced laser desorption ionization time of flight mass spectrometry. Then, using integrated protein mass profile analysis methods, data is used to compare protein expression profiles of the various treatment groups. Analysis can be performed using appropriate statistical methods.

Example 14

Clinical Trials to Assess the Efficacy of Creatine Prodrugs for Treating Parkinson's Disease The following clinical study may be used to assess the efficacy of a creatine prodrug in treating Parkinson's disease. Patients with idiopathic PD fulfilling the Queen Square Brain Bank criteria (Gibb et at., J Neurol Neurosurg Psychiatry 1988, 51, 745-752) with motor fluctuations and a defined short duration GABA analog response (1.5-4 hours) are eligible for inclusion. Clinically relevant peak dose dyskinesias following each morning dose of their current medication are a further pre-requisite. Patients are also required to have been stable on a fixed dose of treatment for a period of at least one month prior to starting the study. Patients are excluded if their current drug regime includes slow-release formulations of L-Dopa, COMT inhibitors, selegiline, anticholinergic drugs or other drugs that could potentially interfere with gastric absorption (e.g. antacids). Other exclusion criteria include patients with psychotic symptoms or those on antipsychotic treatment patients with clinically relevant cognitive impairment, defined as MMS (Mini Mental State) score of less than 24 (Folstein et al., J Psychiatr Res 1975, 12, 189-198), risk of pregnancy, Hoehn & Yahr stage 5 in off-status, severe, unstable diabetes mellitus, and medical conditions such as unstable cardiovascular disease or moderate to severe renal or hepatic impairment. Full blood count, liver, and renal function blood tests are taken at baseline and after completion of the study.

A randomized, double-blind, and cross-over study design is used. The pharmacokinetics of a creatine prodrug and released creatine can be assessed by determining the blood concentrations at appropriate time intervals. Creatine levels in the brain can also be determined non-invasively by magnetic resonance spectroscopy (MRS).

For clinical assessment, motor function is assessed using UPDRS (United Parkinson's Disease Rating Scale) motor score and BrainTest (Giovanni et al., J Neurol Neurosurg Psychiatry 1999, 67, 624-629), which is a tapping test performed with the patient's more affected hand on the keyboard of a laptop computer. These tests are carried out at baseline and then immediately following each blood sample until patients reach their full on-stage, and thereafter at intervals until patients reach their baseline off-status. Once patients reach their full on-state, video recordings are performed three times at 20 min intervals. The following mental, and motor tasks, which have been shown to increase dyskinesia (Duriff et al, Mov Disord 1999, 14, 242-245) are monitored during each video session: (1) sitting still for 1 minute; (2) performing mental calculations; (3) putting on and buttoning a coat; (4) picking up and drinking from a cup of water; and (5) walking. Videotapes are scored using, for example, versions of the Goetz Rating Scale and the Abnormal Involuntary Movements Scale to document a possible increase in test compound induced dyskinesia.

Actual occurrence and severity of dyskinesia is measured with a Dyskinesia Monitor (Manson et al., J Neurol Neurosurg Psychiatry 2000, 68, 196-201). The device is taped to a patient's shoulder on their more affected side. The monitor records during the entire time of a challenging session and provides a measure of the frequency and severity of occurring dyskinesias.

Results can be analyzed using appropriate statistical methods.

Example 15

Efficacy of Creatine Prodrugs in MPTP Induced Neurotoxicity Animal Model of Parkinson's Disease MPTP (1-methyl-4-phenyl-1,2,3,6-tetrahydropyridine) is a neurotoxin that produces a Parkinsonian syndrome in both man and experimental animals. Studies of the mechanism of MPTP neurotoxicity show that it involves the generation of a major metabolite, $MPP^+$, formed by the activity of monoamine oxidase on MPTP. Inhibitors of monoamine oxidase block the neurotoxicity of MPTP in both mice and primates. The specificity of the neurotoxic effects of $MPP^+$ for dopaminergic neurons appears to be due to the uptake of $MPP^+$ by the synaptic dopamine transporter. Blockers of this transporter prevent $MPP^+$ neurotoxicity. $MPP^+$ has been shown to be a relatively specific inhibitor of mitochondrial complex I activity, binding to complex I at the retenone binding site and impairing oxidative phosphorylation. In vivo studies have shown that MPTP can deplete striatal ATP concentrations in mice. It has been demonstrated that $MPP^+$ administered intra-striatally in rats produces significant depletion of ATP as well as increased lactate concentration confined to the striatum at the site of the injections. Compounds that enhance ATP production can protect against MPTP toxicity in mice.

A creatine prodrug is administered to animals such as mice or rats for three weeks before treatment with MPTP. MPTP is administered at an appropriate dose, dosing interval, and mode of administration for 1 week before sacrifice. Control groups receive either normal saline or MPTP hydrochloride alone. Following sacrifice the two striate are rapidly dissected, and placed in chilled 0.1 M perchloric acid. Tissue is subsequently sonicated and aliquots analyzed for protein content using a fluorometer assay. Dopamine, 3,4-dihydroxy phenyl acetic acid (DOPAC), and homovanillic acid (HVA) are also quantified. Concentrations of dopamine and metabolites are expressed as nmol/mg protein.

Creatine prodrugs that protect against DOPAC depletion induced by MPTP, HVA, and/or dopamine depletion are neuroprotective and therefore can be useful for the treatment of Parkinson's disease.

Example 16

Evaluation of Potential Anti-Parkinsonian Activity Using a Haloperidol-Induced Hypolocomotion Animal Model It has been demonstrated that adenosine antagonists, such as theophylline, can reverse the behavioral depressant effects of dopamine antagonists, such as haloperidol, in rodents and is considered a valid method for screening drugs with potential antiparkinsonian effects (Mandhane, et al., Eur. J. Pharmacol. 1997, 328, 135-141). The ability of creatine prodrugs to block haloperidol-induced deficits in locomotor activity in mice can be used to assess both in vivo and potential anti-Parkinsonian efficacy.

Mice used in the experiments are housed in a controlled environment and allowed, to acclimatize before experimental use. 1.5 h before testing, mice are administered 0.2 mg/kg haloperidol, a dose that reduces baseline locomotor activity by at least 50%. A test compound is administered 5-60 min prior to testing. The animals are then placed individually into clean, clear polycarbonate cages with a flat perforated lid. Horizontal locomotor activity is determined by placing the cages within a frame containing a 3×6 array of photocells interfaced to a computer used to tabulate beam interrupts. Mice are left undisturbed to explore for 1 h, and the number of beam interruptions made during this period serves as an indicator of locomotor activity, which is compared with data for control animals for statistically significant differences.

Example 17

6-Hydroxydopamine Animal Model of Parkinson's Disease

The neurochemical deficits seen in Parkinson's disease can be reproduced by local injection of the dopaminergic neurotoxin, 6-hydroxydoparriine (6-OHDA) into brain regions containing either the cell bodies or axonal fibers of the nigrostriatal neurons. By unilaterally lesioning the nigrostriatal pathway on only one-side of the brain, a behavioral asymmetry in movement inhibition is observed. Although unilaterally-lesioned animals are still mobile and capable of self maintenance, the remaining dopamine-sensitive neurons on the lesioned side become supersensitive to stimulation. This is demonstrated by the observation that following systemic administration of dopamine agonists, such as apomorphine, animals show a pronounced rotation in a direction contralateral to the side of lesioning. The ability of compounds to induce contralateral rotations in 6-OHDA lesioned rats has been shown to be a sensitive model to predict drug efficacy in the treatment of Parkinson's disease.

Male Sprague-Dawley rats are housed in a controlled environment and allowed to acclimatize before experimental use. Fifteen minutes prior to surgery, animals are given an intraperitoneal injection of the noradrenergic uptake inhibitor diesipramine (25 mg/kg) to prevent damage to nondopamine neurons. Animals are then placed in an anaesthetic chamber and anaesthetized using a mixture of oxygen and isoflurane: Once unconscious, the animals are transferred to a stereotaxic frame, where anesthesia is maintained through a mask. The top of the animal's head is shaved and sterilized using an iodine solution. Once dry, a 2 cm long incision is made, along the midline of the scalp and the skin retracted and clipped back to expose the skull. A small hole is then drilled through the skull above the injection site. In order to lesion the nigrostriatal pathway, the injection cannula is slowly lowered to position above the right medial forebrain bundle at −3.2 mm anterior posterior, −1.5 mm medial lateral from the bregma, and to a depth of 7.2 mm below the duramater. Two minutes after lowering the cannula, 6-OHDA is infused at a rate of 0.5 μL/min over 4 min, yielding a final dose of 8 μg. The cannula is left in place for an additional 5 min to facilitate diffusion before being slowly withdrawn. The skin is then sutured shut, the animal removed from the stereotaxic frame, and returned to its housing. The rats are allowed to recover from surgery for two weeks before behavioral testing.

Rotational behavior is measured using a rotometer system having stainless steel bowls (45 cm diameter×0.15 cm high) enclosed in a transparent Plexiglas cover running around the edge of the bowl and extending to a height of 29 cm. To assess rotation, rats are placed in a cloth jacket attached to a spring tether connected to an optical rotometer positioned above the bowl, which assesses movement to the left or right either as partial (45°) or full (360° rotations).

To reduce stress during administration of a test compound, rats are initially habituated to the apparatus for 15 min on four consecutive days. On the test day, rats are given a test compound, e.g., a creatine prodrug. Immediately prior to testing, animals are given a subcutaneous injection of a subthreshold dose of apomorphine, and then placed in the harness and the number of rotations recorded for one hour. The total number of full contralateral rotations during the hour test period serves as an index of antiparkinsonian drug efficacy.

Example 18

Animal Studies to Assess the Efficacy of Creatine Prodrugs in Ischemic Injury

Adult male rats are given a creatine prodrug and, after about 24 h, are anesthetized and prepared for coronary artery occlusion. An additional dose of a creatine prodrug is administered at the start of the procedure and the left main coronary artery occluded for 30 min and then released. The same dose of a creatine prodrug is then administered at appropriate intervals and duration following surgery. The animals are then studied for cardiac function. Animals receiving a sham injection (saline) demonstrate a large increase in the left end diastolic pressure, indicative of a dilated, stiff heart secondary to myocardial infarction. Creatine prodrugs that eliminate or reduce the deficit in cardiac function compared to sham operated control are useful in preventing ischemic injury.

Example 19

Animal Studies to Assess the Ability of Creatine Prodrugs to Maintain Organ Viability Wistar male rats weighing 300 to 330 g are administered a creatine prodrug or vehicle 24 h prior to removal of the heart for ex vivo studies. Animals are sacrificed with pentobarbital (0.3 mL) and intravenously heparinized (0.2 mL). The hearts are initially allowed to equilibrate for 15 min. The left ventricular balloon is then inflated to a volume that gives an end-diastolic pressure of about 8 mm Hg. A left ventricular pressure-volume curve is constructed by incremental inflation of the balloon volume by 0.02 mL aliquots. Zero volume is defined as the point at which the left ventricular end-diastolic pressure is zero. On completion of the pressure-volume curve, the left ventricular balloon is deflated to set end-diastolic pressure back to 8 mmHg and the control period is continued for 15 min after check of coronary flow. The heart is then arrested with 50 mL Celsior+molecule to rest at 4° C. under a pressure of 60 cm $H_2O$. The heart is then removed and stored for 5 h at 4° C. in a plastic container filled with the same solution and surrounded with crushed ice.

After storage, the heart is transferred to a Langendorff apparatus. The balloon catheter is re-inserted into the left ventricle and re-inflated to the same volume as during the preischemic period. The heart is reperfused for at least 2 h at 37° C. The re-perfusion pressure is, set at 50 cm $H_2O$ for 15 min of re-flow and then back to 100 cm $H_2O$ for the 2 next h. Pacing (320 beats per min) is re-instituted. Isovolumetric measurements of contractile indexes and diastolic pressure are taken in triplicate at 25, 45, 60, and 120 min of reperfusion. At this time point pressure volume curves are obtained and coronary effluent during, the 45 min reperfusion collected to measure creatine kinase leakage. Improved left ventricular pressure following treatment with a prodrug of a creatine analog, as well as improved volume-pressure curve, decrease of left diastolic ventricular pressure and decrease of creatine kinase leakage indicates the ability of the creatine prodrug to maintain organ viability.

Example 20

Neuroprotective Effects of Prodrugs of Creatine Analogs in a Transgenic Mouse Model of Huntington's Disease Transgenic HD mice of the N171-82Q strain and non-transgenic littermates are treated with a prodrug of a creatine analog or a vehicle from 10 weeks of age. The mice are placed on a rotating rod ("rotarod"). The length of time at which a mouse falls from the rotarod is recorded as a measure of motor coordination. The total distance traveled by a mouse is also recorded as a measure of overall locomotion. Mice administered creatine prodrugs that are neuroprotective in the N171-82Q transgenic HD mouse model remain on the rotarod for a longer period of time and travel further than mice administered vehicle.

Example 21

Efficacy of Creatine Prodrugs in a Malonate Model of Huntington's Disease

A series of reversible and irreversible inhibitors of enzymes involved in energy generating pathways has been used to generate animal models for neurodegenerative diseases such as Parkinson's and Huntington's diseases. Inhibitors of succinate dehydrogenase, an enzyme that impacts cellular energy homeostasis, has been used to generate a model for Huntington's disease (Brouillet et al., J. Neurochem. 1993, 60, 356-359; Beal et al., J. Neurosci. 1993, 13, 4181-4192; Henshaw et al., Brain Research 1994, 647, 161-166 (1994); and Beal et al., J. Neurochem. 1993, 61, 1147-1150). The enzyme succinate dehydrogenase plays a central role in both the tricarboxylic acid cycle as well as the electron transport chain in the mitochondria. Malonate is a reversible inhibitor malonate of succinate dehydrogenase. Intrastriatal injections of malonate in rats have been shown to produce dose dependent striatal excitotoxic lesions that are attenuated by both competitive and noncompetitive NMD A antagonists (Henshaw et al., Brain Research 1994, 647, 161-166). The glutamate release inhibitor, lamotrigine, also attenuates the lesions. Co-injection with succinate blocks the lesions, consistent with an effect on succinate dehydrogenase. The lesions are accompanied by a significant reduction in ATP levels as well as significant increase in lactate levels in vivo as shown by chemical shift resonance imaging (Beal et al., J. Neurochem. 1993, 61, 1147-1150). The lesions produced the same pattern of cellular sparing, which is seen in Huntington's disease, supporting malonate challenge as a useful model for the neuropathology and neurochemical features of Huntington's disease.

To evaluate the effect of creatine prodrugs in this malonate model for Huntington's disease, a creatine prodrug is administered at an appropriate dose, dosing interval, and route, to male Sprague-Dawley rats. A prodrug is administered for two weeks prior to the administration of malonate and then for an additional week prior to sacrifice. Malonate is dissolved in distilled deionized water and the pH adjusted to 7.4 with 0.1 M HCl. Intrastriatal injections of 1.5 μL of malonate containing 3 μmol are made into the left striatum at the level of the Bregma 2.4 mm lateral to the midline and 4.5 mm ventral to the dura. Animals are sacrificed at 7 days by decapitation and the brains quickly removed and placed in ice cold 0.9% saline solution. Brains are sectioned at 2 mm intervals in a brain mold. Slices are then placed posterior side down in 2% 2,3,5-triphenyltetrazolium chloride. Slices are stained in the dark at room temperature for 30 min and then removed and placed in 4% paraformaldehyde pH 7.3. Lesions, noted by pale staining, are evaluated on the posterior surface of each section. The measurements are validated by comparison with measurements obtained on adjacent Nissl stain sections.

Compounds exhibiting a neuroprotective effect and therefore useful in treating Huntington's disease show a reduction in malonate-induced lesions.

Example 22

Efficacy of Creatine Prodrugs in a Model of Creatine Transporter Disorder

A mouse model of human CrT deficiency has been generated, which enables development of treatments for this condition (Skelton et al., PloS One, 201, 6 (1), e16187), Mice with exons 2-4 of Slc6a8 flanked by loxP sites were crossed to Cre:CMV mice to create a line of ubiquitous CrT knockout expressing mice. Male CrT−/y (affected) mice lack Cr in the brain and muscle with significant reductions of Cr in other tissues including heart and testes. CrT−/y mice show increased path length during acquisition and reversal learning in the Morris water maze. During probe trials, CrT−/y mice show increased average distance from the platform site. CrT−/y mice show reduced novel object recognition and conditioned fear memory compared to CrT+/y. CnT−/y mice have increased serotonin and 5-hydroxyindole acetic acid in the hippocampus and prefrontal cortex. Ubiquitous CrT knockout mice have learning and memory deficits resembling human CrT deficiency and this model is useful in understanding this disorder and testing creatine prodrugs as therapies for this disorder.

To evaluate the effect of creatine prodrugs in the Morris Water Maze (MWM), a creatine prodrug is administered at an appropriate dose, dosing interval, and route, to male CrT−/y mice. The MWM is a test of spatial learning and reference memory (Vorhees et at., Nature Protocols 2006, 1: 848-858). and animals are tested as described by Skelton et al., Brain Res 2003, 984: 1-10 and Schaefer et al., Neuroscience 2009, 164: 1431-1443. Prior to hidden platform testing, visible platform training (cued learning) is conducted for 6 days. During this phase, curtains are closed around the maze to obscure prominent distal cues and a 10 cm diameter platform with an orange ball mounted above it on a brass rod is placed in a predetermined quadrant. Oh the first day, 6 trials (90 s) are administered with the platform and start in the same position; 2 trials per day are given on subsequent days with the start and platform positions randomized.

The hidden platform portion of the MWM test is conducted in three phases (6 days/phase: acquisition, reversal, and shift) consisting of 4 trials per day for 6 days for animals to learn the location of the hidden platform followed by a single probe trial (no platform) on day 7 (Vorhees et al., Nature Protocols 2006, 1: 848-858). Platform diameters are 10 cm for acquisition, 7 cm for reversal (located in the opposite quadrant), and 5 cm for shift, (located in one of the adjacent quadrants). Performance is measured using AnyMaze software (Stoelting Company, Wood Dale, Ill.). The effect of prodrug treatment is analyzed by comparing performance of control (untreated male CrT−/y mice and/or wild type mice) to prodrug treated mice.

To evaluate the effect of creatine prodrugs in the Conditioned Fear model, a creatine prodrug is administered at an appropriate dose, dosing interval, and route, to male CrT−/y mice. Cued and contextual fear is assessed as described by Peters et al., Science 2010, 328: 1288-1290). On day 1, untreated (control) and treated (prodrug administered) mice are exposed to 30 tones (82 dB, 2 kHz, 30 s on/off cycle) followed by 3 tone-footshock pairings (0.5 mA for 1 s). On the following day, animals are returned to the chamber with no tone or shock presented as a test of contextual fear. The next day, animals are placed in the chamber with a novel grid floor. Following 3 min acclimatization, the tone is presented and freezing behavior scored. Animals are then exposed to 30 cycles of 30 s with and 30 s without tone to measure fear extinction. Freezeframe software and Coulbourn test chambers are used (Coulbourn Instruments, Allentown, Pa.). Percent time freezing is analyzed. The effect of prodrug treatment is analyzed by comparing performance of control (untreated male CrT−/y mice and/or wild type mice) to prodrug treated mice.

To evaluate the effect of creatine prodrugs in the Novel Object Recognition (NOR) model, a creatine prodrug is administered at an appropriate dose, dosing interval, and route, to male CrT−/y mice. NOR is a test of short-term memory (Clark et al., J Neurosci 2000, 20: 8853-8860). Mice are habituated to the arena (91 cm diameter) for 2 days (10 min/day) followed by 2 days (10 min/day) of habituation to two identical objects. On the test day, animals are presented with two new identical objects until 30 s of cumulative observation time is obtained. One hour later memory is tested by presenting the animal with an identical copy of one of the familiar objects along with a novel object. A discrimination index is calculated by subtracting the time observing the familiar object from time spent observing the novel object. The effect of prodrug treatment is analyzed by comparing performance of control (untreated male CrT−/y mice and/or wild type mice) to prodrug treated mice.

Compounds useful in treating creatine transporter disorder will show an improvement in treated male CrT−/y mice relative to untreated controls in one or more of the evaluations outlined above or in alternative models for testing behavior, neurological and/or neuromuscular function.

Example 23

Synthesis of ethyl (N'-hydroxy-N-methylcarbamimidamido)acetate

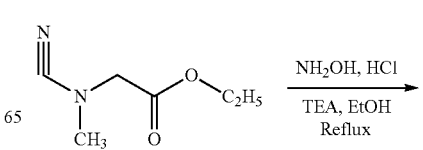

-continued

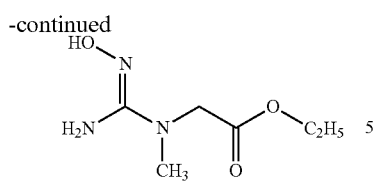

Ethyl (N'-hydroxy-N-methylcarbamimidamido) acetate can be synthesized using the procedure described in Zbinden et al., Bioorganic & Medicinal Chemistry Letters, 2005, 15: 5344-5352. Briefly, ethyl [cyano(methyl)amino] acetate, available from MP Biomedicals, Inc., is reflux with hydroxylamine hydrochloride in EtOH to give the title compound.

Example 24

Synthesis of tert-butyl 2-(3-(tert-butoxycarbonyl)-2-hydroxy-1-methylguanidino)acetate-3-yl)amino]acetate

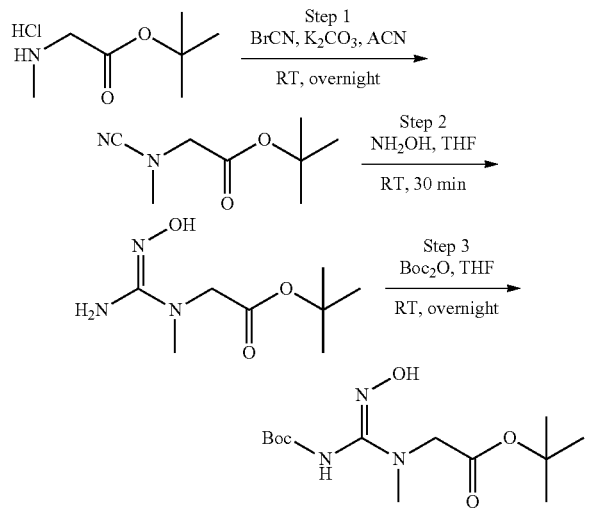

Step 1: Synthesis of tert-butyl 2-(N-methylcyanamido)acetate

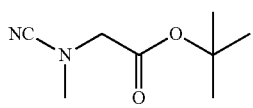

A round bottom flask equipped with a stir bar was charged with tert-butyl 2-(methylamino)acetate (500 mg, 2.75 mmol), potassium carbonate (761 mg, 5.50 mmol) and acetonitrile (10 mL). The mixture was stirred at room temperature for 30 min at which time a solution of cyanogen bromide (320 mg, 3.025 mmol) in acetonitrile (2 ml) was added. The reaction was allowed to stir overnight at room temperature and the solvent was decanted leaving behind an insoluble residue. The solvent was then evaporated under reduced pressure and the material was purified by flash chromatography eluting with petroleum ether—ethyl acetate (gradient 0% to 40% ethyl acetate) to give tert-butyl 2-(N-methylcyanamidb)acetate (410 mg, 2.41 mmol, 88% yield) as a white solid. ES LC-MS m/z=171 (M+H⁺)& 193 (M+Na⁺), Step 2: Synthesis of tert-butyl 2-(2-hydroxy-1-methylguanidino)acetate

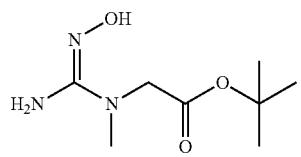

A round bottom flask equipped with a stir bar was charged with tert-butyl 2-(N-methylcyanamido)acetate (300 mg, 1.76 mmol) and tetrahydrofuran (5 mL). To this mixture was added hydroxylamine (50% aqueous, 583 mg, 8.80 mmol). After 1 hour, 10 mL of water was added and the mixture was extracted with 5 ml dichloromethane 3 times. The organic layer was then dried with MgSO₄, filtered and concentrated under reduced pressure to give crude tert-butyl 2-(2-hydroxy-1-methylguanidino)acetate (349 mg, 1.72 mmol, 98% yield) as a white solid which was used immediately in the next step. ES LC-MS m/z=204 (M+H⁺).

Step 3: Synthesis of tert-butyl 2-(3-(tert-butoxycarbonyl)-2-hydroxy-1-methylguanidino)acetate-3-yl)amino]acetate

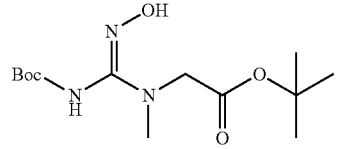 [SMILES: CN(CC(=O)OC(C)(C)C)/C(=N\O)NC(=O)OC(C)(C)C]

A round bottom flask equipped with a stir bar was charged with ter/-butyl 2-(2-hydroxy-1-methylguanidino)acetate (349 mg, 1.72 mmol) and tetrahydrofuran (5 mL). To this mixture was added di-tert-butyl dicarbonate (375 mg, 1.72 mmol). The reaction was stirred at room temperature overnight. The solvent was then evaporated under reduced pressure and the material was purified by flash chromatography eluting with dichloromethane—ethyl acetate (gradient 0% to 30% ethyl acetate) to give tert-butyl 2-(3-(tert-butoxycarbonyl)-2-hydroxy-1-methylguanidino)acetate (151 mg, 0.50 mmol, 29% yield) as a white solid. ES LC-MS m/z=304 (M+H⁺). ¹H NMR (DIMETHYL SULFOXIDE-d) δ: 5.73 (s, 2H), 3.81 (s, 2H), 2.76 (s, 3H), 1.42 (s,9H),1.41(s, 9H).

Example 25

Synthesis of tert-butyl 2-(3-(tert-butoxycarbonyl)-2-hydroxy-1-trideuteriomethylguanidino)acetate

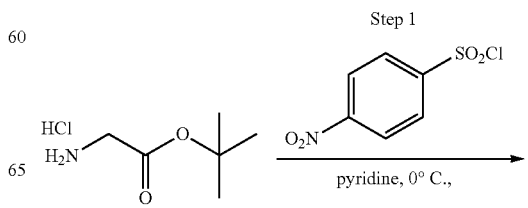

97

-continued

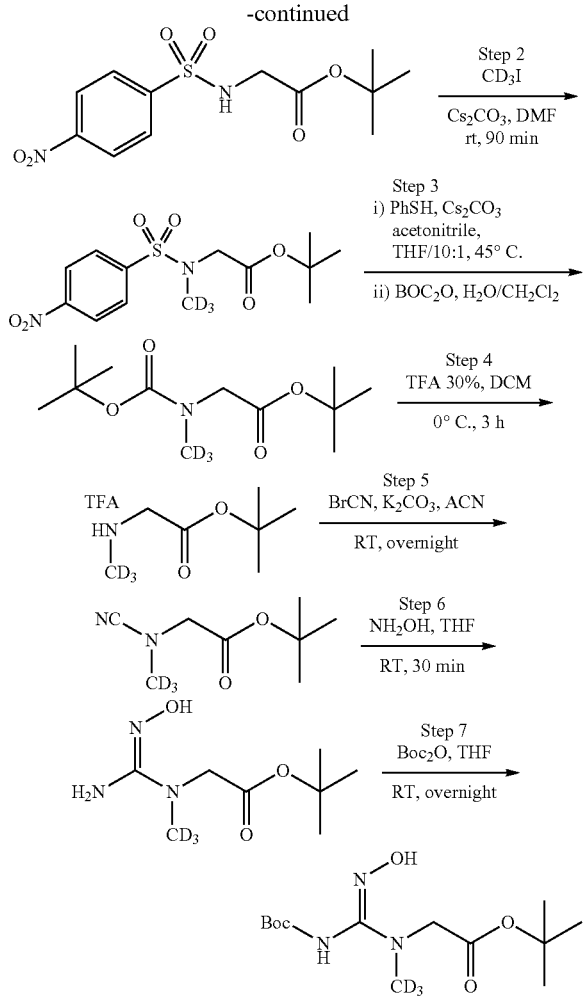

Step 1: Synthesis of tert-butyl 2-(4-nitrophenylsulfonamido) acetate

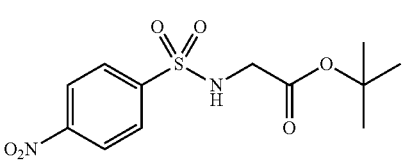 [SMILES: CC(C)(C)OC(=O)CNS(=O)(=O)c1ccc([N+](=O)[O-])cc1]

A round bottom flask equipped with a stir bar and under nitrogen was charged with glycine tert-butyl ester hydrochloride (20 g, 119.76 mmol) and pyridine (260 mL). The mixture was cooled to 0° C. at which time 4-nitrobenzenesulfonyl chloride (28.98 g, 131.74 mmol) was added portion-wise maintaining the mixture below 10° C. The reaction was then allowed to warm to room temperature. After 18 h at room temperature, the reaction mixture was poured into water (1000 mL). A precipitate formed which was filtered and dried under vacuum to give tert-butyl 2-(4-nitrophenyl-sulfonamido) acetate (30.8 g, 97.46 mmol, 81% yield) as a yellow solid. $^1$H NMR (CDCl$_3$) δ: 8.36-8.34 (m, 2H), 8.07-8.05 (m, 2H), 5:23 (br s, 1H), 3.75-3.74 (d, J=5.6 Hz, 2H), 1.35 (s, 9H).

98

Step 2: Synthesis of tert-butyl 2-[(4-nitrophenyl) sulfonyl-(trideuteriomethyl)amino]acetate

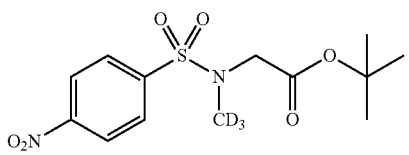 [SMILES: [2H]C([2H])([2H])N(CC(=O)OC(C)(C)C)S(=O)(=O)c1ccc([N+](=O)[O-])cc1]

A round bottom flask equipped with a stir bar and under nitrogen was charged with tert-butyl 2-(4-nitrophenylsulfonamido) acetate (30.8 g, 97.46 mmol), DMF (320 mL) and CD$_3$I (14.13 g, 97.46 mmol). To this mixture at room temperature was added Cs$_2$CO$_3$ (34.85 g, 107.22 mmol) and the reaction was stirred for 45 min. The reaction mixture was then poured into water (1000 mL) and extracted with EtOAc (3×500 mL). The combined organic phases were washed with NaCl (500 mL), dried (Na$_2$SO$_4$), filtered and the solvent was evaporated under reduced pressure to give tert-butyl 2-[(4-nitrophenyl)sulfonyl-(trideuteriomethyl) amino]acetate (27.8 g, 83.48 mmol, 81% yield as a pale yellow solid. $^1$H NMR (CDCl$_3$) δ: 8.36-8.33 (d, J=8.8 Hz, 2H), 8.01-7.99 (d, J=9.2 Hz, 2H), 3.98 (s, 2H), 1.38 (s, 9H).

Step 3: Synthesis of tert-butyl 2-(tert-butoxycarbonyl(trideuteriomethyl)amino)acetate

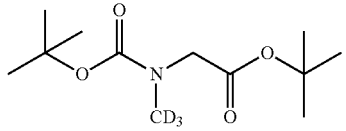

A round bottom flask equipped with a stir bar and under nitrogen was charged tert-butyl 2-[(4-nitrophenyl)sulfonyl-(trideuteriomethyl)amino]acetate (27.8 g, 83.48 mmol), Cs$_2$CO$_3$ (67.83 g, 208.7 mmol) acetonitrile (400 mL) and THF (40 mL). To this solution was added thiophenol (34 mL, 333.93 mmol) and the reaction was heated at 45° C. for 90 min at which time the reaction mixture was diluted with MTBE (500 mL) and extracted with water (5×100 mL). The combined water extracts were washed with MTBE (500 mL) and to the water mixture, was added DCM (500 mL) followed by (BOC)$_2$O (36.4 g, 166.97 mmol). The biphasic reaction mixture was stirred vigorously overnight. The phases were then separated and the aqueous layer was extracted with DCM (500 mL×5). The combined organic phases dried (Na$_2$SO$_4$), filtered and the solvent was evaporated under reduced pressure. The material was purified by chromatography using a 120 g silica cartridge eluting with heptanes—EtOAc (gradient 0% to 30% EtOAc) to give tert-butyl 2-(tert-butoxycarbonyl(trideuteriomethyl)amino) acetate (6 g, 24.19 mmol, 28% yield) as a colorless oil. $^1$H NMR (CDCl$_3$) δ: 3.84-3.74 (m, 2H), 1.45-1.41 (m, 18H).

Step 4: Synthesis of tert-butyl 2-(N-trideuterio methylamino)acetate TFA salt

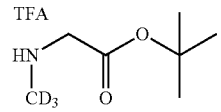

A round bottom flask equipped with a stir bar was charged with terf-butyl 2-(tert-butoxycarbonyl(trideuteriomethyl) amino)acetate (500 mg, 2.02 mmol) and dichloromethane (2 mL). The mixture was cooled to 0° C. at which time 1 mL of trifluoroacetic acid (TFA) was added, the mixture was then stirred at 0° C. for 3 hours. The solvent was then evaporated under reduced pressure to give tert-butyl 2-(N-trideuterio methylamino)acetate TFA salt (320 mg, 2.02 mmol, 100% yield) as a pale brown oil, which was used directly in the next step, ES LC-MS m/z=149 (M+H$^+$).

Step 5: Synthesis of tert-butyl 2-(N-trideuteriomethylcyanamido)acetate

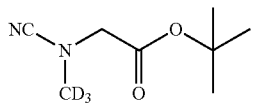

A round bottom flask equipped with a stir bar was charged with tert-butyl 2-(N-trideuterio methylamino)acetate TFA salt (320mg, 2.02mmol), potassium carbonate (837 mg, 6.06mmol) and acetonitrile (10 mL). The mixture was stirred at room temperature for 0.5 hours, at which time a solution of cyanogen bromide (235 mg, 2.22 mmol) in acetonitrile (2 ml) was added. The reaction was allowed to stir overnight at room temperature. The, solvent was then decanted leaving behind an insoluble residue. The solvent was evaporated under reduced pressure and then purified by flash chromatography eluting with petroleum ether—ethyl acetate (gradient 0% to 40% ethyl acetate) to give tert-butyl 2-(N-trideuteriomethyicyanamido)acetate (260 mg, 1.50 mmol, 74% yield) as a white solid. ES LC-MS m/z=174 (M+H$^+$) & 196 (M+Na$^+$).

Step 6: Synthesis of tert-butyl 2-(2-hydroxy-1-trideuteriomethylguanidino)acetate

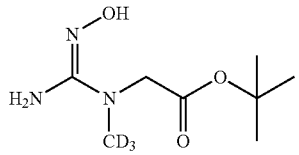 [SMILES: [2H]C([2H])([2H])N(CC(=O)OC(C)(C)C)/C(N)=N\O]

A round bottom flask equipped with a stir bar was charged with tert-butyl 2-(N-trideuteriomethylcyanamido)acetate (260 mg, 1.50 mmol) and tetrahydrofuran (5 mL). To this mixture was added hydroxylamine (50% aqueous, 495 mg, 7.50 mmol). After 1 hour, 10 mL of water was added and the mixture was extracted with 5 mL of dichloromethane 3 times. The organic layer was dried with MgSO$_4$, filtered and concentrated under reduced pressure to give tert-butyl 2-(2-hydroxy-1-trideuteriomethylguanidino)acetate (298 mg, 1.45 mmol, 97% yield) as a white solid which was used immediately in the next step. ES LC-MS m/z=207 (M+H$^+$).

Step 7: Synthesis of tert-butyl 2-(3-(tert-butoxycarbonyl)-2-hydroxy-1-trideuteriomethylguanidino) acetate

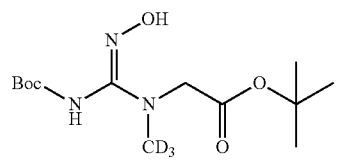 [SMILES: [2H]C([2H])([2H])N(CC(=O)OC(C)(C)C)/C(=N\O)NC(=O)OC(C)(C)C]

A round bottom flask equipped with a stir bar was charged with tertbutyl 2-(2-hydroxy-1-trideuteriomethylguanidino) acetate (298 mg, 1.45 mmol) and tetrahydrofuran (5 mL). To this mixture was added di-tert-butyl dicarbonate (316 mg, 1.72 mmol). The reaction was stirred at room temperature overnight. The solvent was then evaporated under reduced pressure and the material was purified by flash chromatography eluting with dichloromethane—ethyl acetate (gradient 0% to 30% ethyl acetate) to give tert-butyl 2-(3-(tert-butoxycarbonyl)-2-hydroxy-1-trideuteriomethylguanidino) acetate (90 mg, 0.29 mmol, 20% yield) as a white solid. ES LC-MS m/z=307 (M+H$^+$). $^1$H NMR (DIMETHYL SULFOXIDE-d) δ: 5.71 (s, 2H), 3.81 (s, 2H), 1.43 (s, 9H), 1.41 (s, 9H).

Other creatine prodrugs and derivatives thereof can be synthesized using the procedure described above by the selection of the appropriate starting material.

Example 26

Synthesis of ethyl 2-[methyl-(5-oxo-4H-1,2,4-oxadiazol-3-yl)amino]acetate

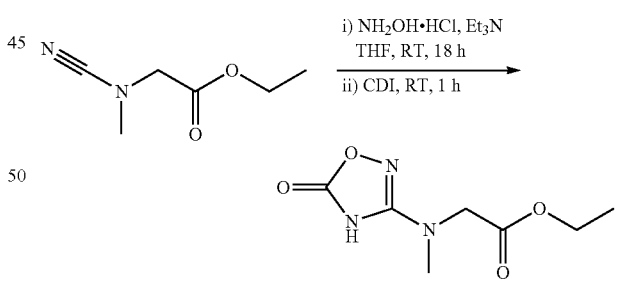

A round bottom flask equipped with a stir bar and nitrogen inlet was charged with ethyl 2-[cyano(methyl)amino]acetate (852 mg, 6.0 mmol) and tetrahydrofuran (30 mL). To this mixture was added hydroxylamine hydrochloride (2.1 g, 30.0 mmol) and triethylamine (1.3 mL, 9.0 mmol). After 18 h, carbonyldiimide (5.8 g, 36.0 mmol) was added and the reaction was allowed 1 h. The solvent was decanted leaving behind an insoluble residue. The solvent was evaporated under reduced pressure and the material was purified by reverse phase chromatography eluting with water-acetonitrile modified with 0.1% trifluoroacetic acid. This gave ethyl 2-[methyl-(5-oxo-4H-1,2,4-oxadiazol-3-yl)amino]acetate as a white solid: 80 mg, 0.40 mmol, 7% yield. ES LC-MS m/z=202 (M+H+). $^1$H NMR (CHLOROFORM-d) δ: 4.25 (q, J=7.2 Hz, 2H), 3.96 (s, 2H), 3.04 (s, 3H), 1.31 (t, J=7.1 Hz, 3H). Melting point 120-123° C.

Eethyl 2-[methyl-(5-oxo-4H-1,2,4-oxadiazol-3-yl)amino] acetate can also be synthesized using the procedure described in Kitamure et al, Chem. Pharm. Bull., 2001, 49(3) 268-277.

Example 27

Synthesis of 2-[methyl-(5-oxo-4H-1,2,4-oxadiazol-3-yl)amino]acetic acid

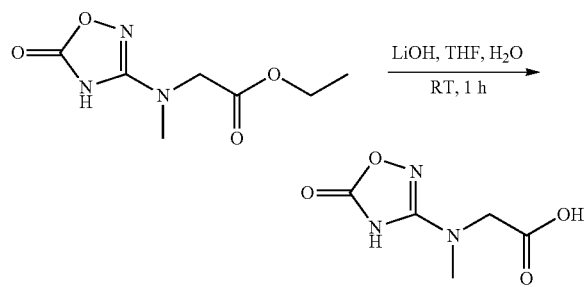

A round bottom flask equipped with a stir bar and nitrogen inlet was charged with ethyl 2-[methyl-(5-oxo-4H-1,2,4-oxadiazol-3-yl)amino]acetate (20 mg, 0.1 mmol), tetrahydrofuran (5 mL) and water (5 mL). To this mixture was added lithium hydroxide mono hydrate (4 mg, 0.1 mmol). After 1 hour the solvent was evaporated under reduced pressure and the material was purified by reverse phase chromatography eluting with water-acetonitrile modified with 0.1% trifluoroacetic acid. This gave 2-[methyl-(5-oxo-4H-1,2,4-oxadiazol-3-yl)amino]acetic acid as a white solid: 15 mg, 0.09 mmol, 90% yield. ES LC-MS m/z=174 (M+H+). $^1$H NMR (METHANOL-d$_4$) δ: 3.97 (s, 2H), 2.96 (s, 3H). Melting point 150-155° C.

Other creatine prodrugs and derivatives thereof can be synthesized using the procedure described above by the selection of the appropriate starting material.

Example 28

Synthesis of alkyl 2-[(5-oxo-2H-1,2,4-oxadiazol-3-yl)-(trideuteriomethyl)amino]acetate

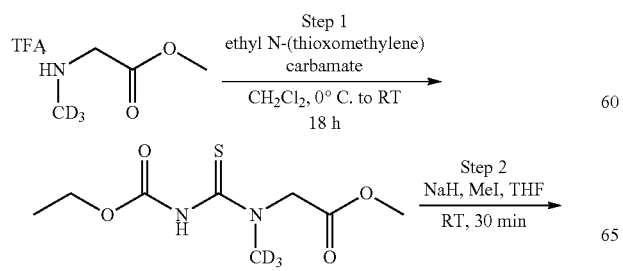

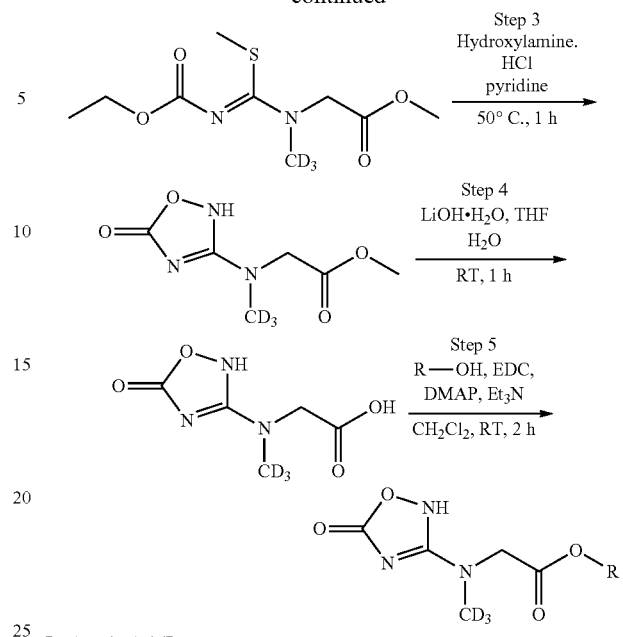

R = heptyl, ethyl, iPr

Step 1: Synethsis of methyl 2-[ethoxycarbonylcarbamothioyl(trideuteriomethyl)amino]acetate

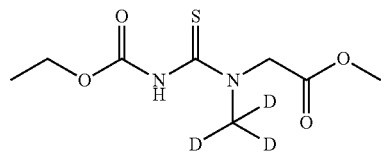 [SMILES: [2H]C([2H])([2H])N(CC(=O)OC)C(=S)NC(=O)OCC]

A round bottom flask equipped with a stir bar and nitrogen inlet was charged with ethyl N-(thioxomethylene)carbamate (4.1 mL, 35.0 mmol) and dichlorornethane (300 mL). The mixture was cooled to 0° C. and methyl 2-(trideuteriomethylamino)acetate trifluoroacetic acid salt (7.70 g, 35.0 mmol) was added followed by triethylamine (4.9 mL, 35.0 mmol). The mixture was stirred overnight with warming to room temperature. The mixture was washed with 1N HCl (100 mL), dried (Na$_2$SO$_4$) and the solvent was evaporated under reduced pressure. The material was purified by chromatography using a 120 g silica cartridge eluting with heptane-ethyl acetate, gradient 0 to 30% ethyl acetate. This gave methyl 2-[ethoxycarbonylcarbamothioyl(trideuteriomethyl) amino]acetate: 8.0 g, 33.8 mmol, 96% yield. ES LC-MS m/z=238 (M+H+). $^1$H NMR (CHLOROFORM-d) δ: 7.38 (br s, 1H), 4.41-4:59 (m, 2H), 4.20 (q, J=7.1 Hz, 2H), 3.80 (s, 3H), 1.31 (t, J=7.1 Hz, 3H).

Step 2: Synethsis of methyl 2-[[(Z)—N-ethoxycarbonyl-C-methylsulfanyl-carbonimidoyl]-(trideuteriomethyl)amino]acetate

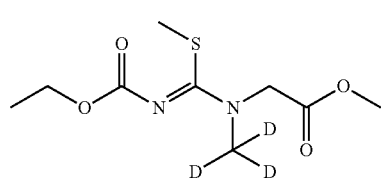 [SMILES: [2H]C([2H])([2H])N(CC(=O)OC)/C(=N/C(=O)OCC)SC]

A round bottom flask equipped with a stir and nitrogen inlet was charged with [ethoxycarbonylcarbamothioyl(trideuteriomethyl)amino]acetate (7.82 g, 33.0 mmol), methyliodide (4.1 mL, 66.0 mmol) and tetrahydrofuran (200 mL). To this mixture at room temperature was added sodium hydride (60% in oil; 1.32 g, 33.0 mmol). After 1 hour, the material was poured into saturated ammonium chloride solution (100 mL), the aqueous phase was extracted with ethyl acetate (3×100 mL), dried (Na$_2$SO$_4$) and the solvent was evaporated under reduced pressure. The material was purified by chromatography using a 120 g silica cartridge eluting with heptane-ethyl acetate, gradient 0 to 40% ethyl acetate. This gave methyl 2-[[(Z)-N-ethoxycarbonyl-C-methylsulfanyl-carbonimidoyl]-(trideuteriomethyl)amino]acetate: 8.0 g, 32.0 mmol, 97% yield. ES LC-MS m/z=252 (M+H$^+$). $^1$H NMR (CHLOROFORM-d) δ: 4.30 (s, 2H), 4.16 (q, J=7.1 Hz, 2H), 3.77 (s, 3H), 2.42 (s, 3H), 1.30 (t, J=7.1 Hz, 3H).

Step 3: Synethsis of methyl 2-[(5-oxo-2H-1,2,4-oxadiazol-3-yl)-(trideuteriomethyl)amino]acetate

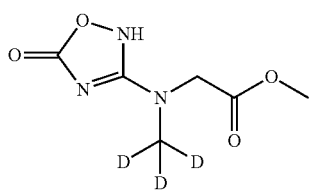 [SMILES: [2H]C([2H])([2H])N(CC(=O)OC)c1nc(=O)o[nH]1]

A round bottom flask equipped with a stir bar, Vigreux column and nitrogen inlet was charged with methyl 2-[[(Z)—N-ethoxycarbonyl-C-methylsulfanyl-carbonimidoyl]-(trideuteriomethyl)amino]acetate (7.53 g, 30.0 mmol) and pyridine (50 mL). To this mixture was added hydroxylamine hydrochloride (2.09 g, 30.0 mmol) and the mixture was heated at 60° C. for 1 hour. The solvent was evaporated under reduced pressure. Ethyl acetate (100 mL) and water (100 mL) was added. The phases were separated and the aqueous phase was extracted with ethyl acetate (3×100 mL). The combined organic phases were dried (Na$_2$SO$_4$) and the solvent was evaporated under reduced pressure. The material was purified by chromatography using a 120 g silica cartridge eluting with heptane-ethyl acetate, gradient 0 to 100% ethyl acetate. This gave methyl 2-[(5-oxo-2H-1,2,4-oxadiazol-3-yl)-(trideuteriomethyl)amino]acetate as a white solid 3.0 g, 15.8 mmol, 53% yield. ES LC-MS m/z=191 (M+H$^+$). $^1$H NMR (CHLOROFORM-d) δ: 3.98 (s, 2H), 3.79 (s, 3H). Melting point 120-125° C.

Step 4: Synethsis of 2-[(5-oxo-2H-1,2,4-oxadiazol-3-yl)-(trideuteriomethyl)amino]acetic acid

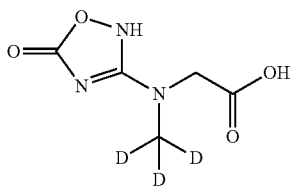 [SMILES: [2H]C([2H])([2H])N(CC(=O)O)c1nc(=O)o[nH]1]

A round bottom flask equipped with a stir bar and nitrogen inlet was charged with methyl 2-[(5-oxo-2H-1,2,4-oxadiazol-3-yl)-(trideuteriomethyl)amino]acetate (95 mg, 0.5 mmol), tetrahydrofuran (5 mL) and water (5 mL). To this mixture was added lithium hydroxide mono hydrate (21 mg, 0.5 mmol). After 1 hour the solvent was evaporated under reduced pressure and the material was purified by reverse phase chromatography eluting with water-acetonitrile modified with 0.1% trifluoroacetic acid. This gave 2-[(5-oxo-2H-1,2,4-oxadiazol-3-yl)-(trideuteriomethyl)amino]acetic acid as a white solid: 50 mg, 0.28 mmol, 57% yield. ES LC-MS m/z=177 (M+H$^+$). $^1$H NMR (METHANOL-d$_4$) δ: 3.98 (s, 2H). Melting point 150-155° C.

Step 5 A: Synethsis of heptyl 2-[(5-oxo-2H-1,2,4-oxadiazol-3-yl)-(trideuteriomethyl)amino]acetate

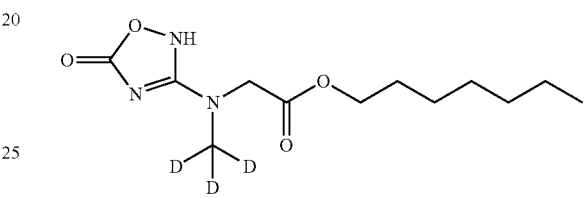

A scintillation vial equipped with a stir bar was charged with 2-[(5-oxo-2H-1,2,4-oxadiazol-3-yl)-(trideuteriomethyl)amino]acetic acid (88 mg, 0.50 mmol), 1-heptanol (58 mg, 0.50 mmol), dimethylamino pyridine (92 mg, 0.75 mmol) and dichloromethane (10 mL). To this mixture was added N-(3-dimethylaminopropyl)-N'-ethylcarbodiimide hydrochloride (144 mg, 0.75 mmol). After 1 hour, triethylamine (0.07 mL, 0.50 mmol) was added. The reaction was allowed another 1 hour. The solvent was evaporated under reduced pressure and the material was purified by reverse phase chromatography eluting with water-acetonitrile modified with 0.1% trifluoroacetic acid. This gave heptyl 2-[(5-oxo-2H-1,2,4-oxadiazol-3-yl)-(trideuteriomethyl)amino]acetate as a white solid: 70 mg, 0.25 mmol, 50% yield. ES LC-MS m/z=275 (M+H$^+$). $^1$H NMR (CHLOROFORM-d) δ: 11.06 (br s, 1H), 4.17 (t, J=6.8 Hz, 2H), 3.95 (s, 2H), 1.56-1.82 (m, 4H), 1.19-1.44 (m, 7H), 0.85-0.94 (m, 2H). Melting point 110-115° C.

Step 5B: Synethsis of ethyl 2-[(5-oxo-2H-1,2,4-oxadiazol-3-yl)-(trideuteriomethyl)amino]acetate

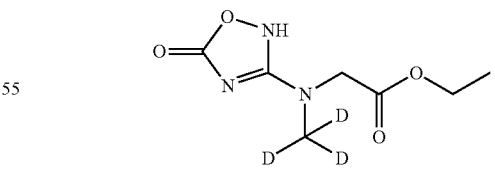

A scintillation vial equipped with a stir bar was charged with 2-[(5-oxo-2H-1,2,4-oxadiazol-3-yl)-(trideuteriomethyl)amino]acetic acid (176 mg, 1.00 mmol), ethanol (46 mg, 1.00 mmol), dimethylamino pyridine (183 mg, 1.50 mmol) and dichloromethane (20 mL). To this mixture was added N-(3-dimethylaminopropyl)-N'-ethylcarbodiimide hydrochloride (288 mg, 1.50 mmol). After 1 hour, triethylamine (0.14 mL, 1.00 mmol) was added. The reaction was allowed another 1 hour. The solvent was evaporated under reduced pressure and the material was purified by reverse phase chromatography eluting with water-acetonitrile modified with 0.1% trifluoroacetic acid. This gave ethyl 2-[(5-oxo-2H-1,2,4-oxadiazol-3-yl)-(trideuteriomethyl)amino]acetate as, a white solid: 133 mg, 0.65 mmol, 65% yield. ES LC-MS m/z=205 (M+H+). $^1$H NMR (CHLOROFORM-d) δ: 11.13 (br s, 1H), 4.24 (q, J=7.2 Hz, 2H), 3.96 (s, 2H), 1.30 (t, J=7.1 Hz, 3H). Melting point 12 -130° C.

Step 5C: Synethsis of isopropyl 2-[(5-oxo-2H-1,2,4-oxadiazol-3-yl)-(trideuteriomethyl)amino]acetate

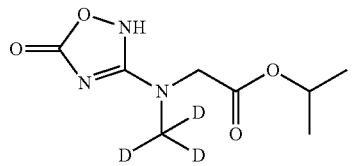 [SMILES: [2H]C([2H])([2H])N(CC(=O)OC(C)C)c1nc(=O)o[nH]1]

A scintillation vial equipped with a stir bar was charged with 2-[(5-oxo-2H-1,2,4-oxadiazol-3-yl)-(trideuteriomethyl)amino]acetic acid (176 mg, 1.00 mmol), isopropanol (60 mg, 1.00 mmol), dimethylamino pyridine (183 mg, 1.50 mmol) and dichloromethane (20 mL). To this mixture was added N-(3-dimethylaminopropyl)-N'-ethylcarbodiimide hydrochloride (288 mg, 1.50 mmol). After 1 hour, triethylamine (0.14 mL, 1.00 mmol) was added. The reaction was allowed another 1 hour. The solvent was evaporated under reduced pressure and the material was purified by reverse phase chromatography eluting with water-acetonitrile modified with 0.1% trifluoroacetic acid. This gave isopropyl 2-[(5-oxo-2H-1,2,4-oxadiazol-3-yl)-(trideuteriomethyl)amino]acetate as a white solid: 139 mg, 0.64 mmol, 64% yield. ES LC-MS m/z=219 (M+H+). $^1$H NMR (CHLOROFORM-d) δ: 11.09 (br s, 1H), 5.10 (sept, J=6.3 Hz, 1H), 3.91 (s, 2H), 1.28 (d, J=62 Hz, 6H). Melting point 143-145° C.

Example 29

Synthesis of 3-[2-hydroxyethyl(trideuteriomethyl)amino]-2H-1,2,4-oxadiazol-5-one

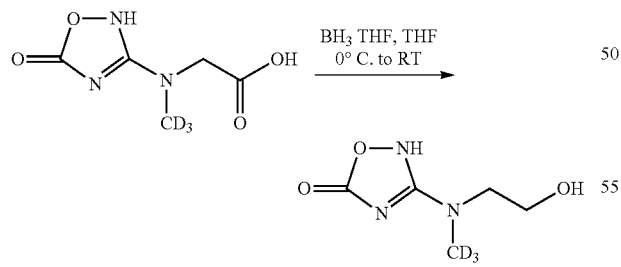

A round bottom flask equipped with a stir bar and nitrogen inlet was charged with 2-[(5-oxo-2H-1,2,4-oxadiazol-3-yl)-(trideuteriomethyl)amino]acetic acid (528 mg, 3.0 mmol) and tetrahydrofuran (THF) (60 mL). To this mixture was added BH$_3$THF (1.0 M in THF) (6.0 mL, 6.0 mmol). After 2 h, the reaction was quenched with methanol (5 mL) and the solvent was evaporated under reduced pressure. The material was purified by reverse phase chromatography eluting with water-acetonitrile modified with 0.1% trifluoroacetic acid. This gave 3-[2-hydroxyethyl(trideuteriomethyl)amino]-2H-1,2,4-oxadiazol-5-one as a white solid: 372 mg, 2.30 mmol, 77% yield, HS LC-MS m/z=163 (M+H+). $^1$H NMR (METHANOL-d$_4$) δ: 3.70 (t, J=5.4 Hz, 3H), 3.33 (s, 1H). Melting point 98-104 ° C.

Example 30

Synthesis of 3-imino-4-(methyl-d$_3$)-1,2,4-oxadiazinan-6-one and 3-amino-4-(methyl-d$_3$)-4,5-dihydro-6H-1,2,4-oxadiazin-6-one

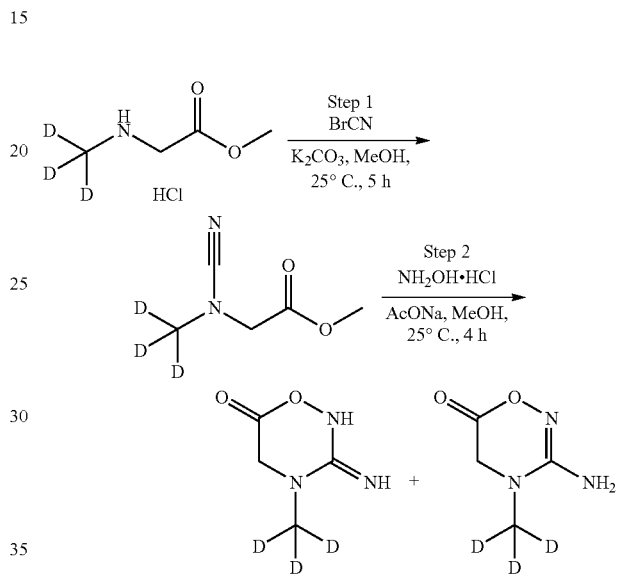

Step 1: Synthesis of methyl 2-[cyano(trideuteriomethyl)amino]acetate

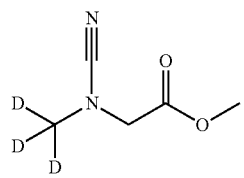

A flask was fitted with methyl 2-(trideuteriomethylamino) acetate (3.00 g, 21,04 mmol, HCl salt), K$_2$CO$_3$ (5.82 g, 42.08 mmol) and MeOH (20.00 mL). Then carbononitridic bromide (2.23 g, 21.04 mmol) was added. After that the reaction mixture was stirred for about 5 hour at 25° C. The reaction mixture was evaporated to afford the residue. H$_2$O (20 mL) was added and EtOAc (35 mL×5) was used to extract the product. The organic layer was washed by brine (20 mL), dried over anhydrous Na$_2$SO$_4$ and evaporated to afford methyl 2-[cyano(trideuteriomethyl)amino]acetate (2.00 g, 72.48% yield) as yellow red oil. $^1$H NMR (MeOD, 400 MHz) δ: 3.91 (s, 2H), 3.79 (s, 3H).

Step 2: Synthesis of 3-imino-4-(methyl-d₃)-1,2,4-oxadiazinan-6-one and 3-amino-4-(methyl-d₃)-4,5-dihydro-6H-1,2,4-oxadiazin-6-one

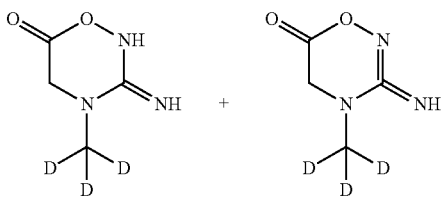

A flask was fitted with methyl 2-[cyano(trideuteriomethyl)amino]acetate (1.00 g, 7.62 mmol), hydroxylamine (2.12 g, 30.50 mmol, HCl salt) and AcONa (2.81 g, 34.31 mmol) in MeOH (20.00 mL). The reaction mixture was stirred at 25° C. for about 4 h. The reaction solution was evaporated to remove most of MeOH. Then H₂O (about 3 mL) was added to make all the solid dissolve. Half of the solution was directly purified by special prep-HPLC (neutral) to afford 4 peaks with desired MS. Peak C, 39.7 mg, light pink. ES LC-MS m/z–130 (M+H⁺). ¹H NMR (DMSO-d6) δ: 3.67 (s, 2H). Peak D, 70.7 mg, white solid. ES LC-MS m/z–130 (M+H⁺). ¹H NMR (DMSO-d6) δ: 3.64 (s, 2H). The remaining peaks may correspond to 3-hydroxy-2-imino-1-(methyl-d₃)imidazolidin-4-one, (Z)-2-(hydroxyimino)-1-(methyl-d₃)imidazolidin-4-one, or (E)-2-(hydroxyimino)-1-(methyl-d₃)imidazolidin-4-one.

Example 31

Synthesis of 4-amino-2,5-dimethyl-5,6-dihydro-1,3,5-oxadiazepih-7(2H)-one

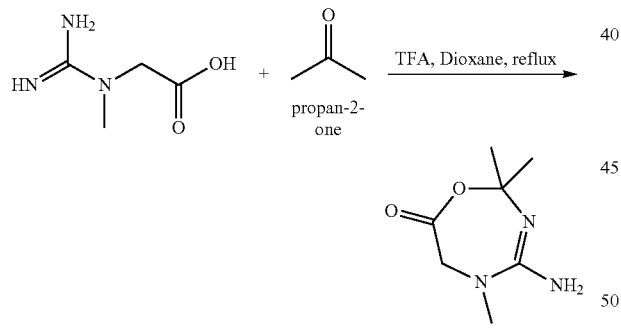

The title compound, 4-amino-2,5-dimethyl-5,6-dihydro-1,3,5-oxadiazepin-7(2H)-one, can be synthesized from the readily available starting materials creatine (available from Sigma Aldrich) and propan-2-one (acetone, also available from Sigma Aldrich). To a stirred solution of creatine (6.55 g; 50 mmol) and acetone (3.70 mL, 50 mmol) in anhydrous dioxane (100 mL) is added trifloroacetic acid (TFA; 2.0 mL; 26 mmol) over 10 minutes. The solution is stirred at room temperature for 10 min, followed by reflux for 1 h,. then concentrated in vacuo to yield the crude product. The crude product is dissolved in a minimum amount of anhydrous dioxane followed by introduction of a stream of anhydrous HCl gas. The resulting precipitate is filtered and washed with dry diethyl ether to yield the HCl salt of the title compound.

By using other aldehydes or ketone instead of propan-2-one, other 4-amino-5,6-dihydro-1,3,5-oxadiazepin-7(2H)-one compounds can be prepared.

Other creatine prodrugs can be synthesized using the procedure described above by the selection of the appropriate starting material.

All publications, including, e.g., non-patent literature, patent applications, and patents, cited in this specification are incorporated herein by reference for all purposes. The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:
1. A compound of Formula (I),

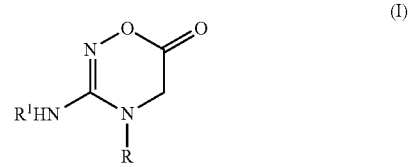

or a pharmaceutically acceptable salt, tautomer or stereoisomer thereof, wherein:
R is —CH₃ or —CD₃;
R¹ is hydrogen, —OR², —C(O)OR², —C(O)R²,

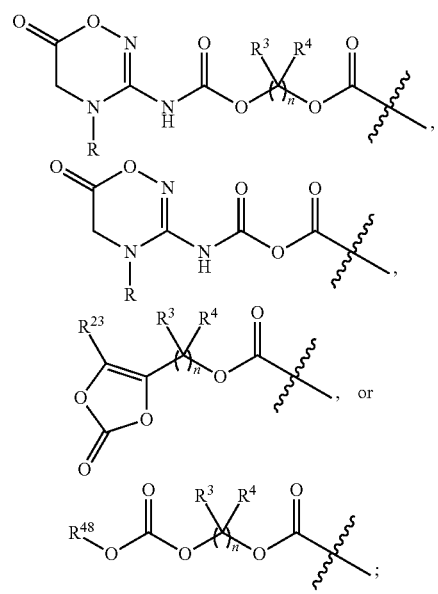

n is an integer from 1 to 2;
each R² is independently hydrogen, C₁₋₁₂ alkyl, substituted C₁₋₁₂ heteroalkyl, substituted C₁₋₁₂ heteroalkyl, C₃₋₁₂ cycloalkyl, substituted C₃₋₁₂ cycloalkyl, C₄₋₂₀ cycloalkylalkyl, substituted. C₄₋₂₀ cycloalkylalkyl, C₄₋₂₀ heterocycloalkylalkyl, substituted C₄₋₂₀ heterocycloalkylalkyl, C₅₋₁₂ aryl, substituted C₅₋₁₂ aryl, C₅₋₁₂ heteroaryl, substituted C$_{5-12}$ heteroaryl, C$_{6-20}$ arylalkyl, substituted C$_{6-20}$ arylalkyl, C$_{6-20}$ heteroarylalkyl or substituted C$_{6-20}$ heteroarylalkyl;

each R$^3$ and R$^4$ is independently hydrogen, C$_{1-12}$ alkyl or substituted C$_{1-12}$ alkyl;

R$^{23}$ is hydrogen, C$_{1-12}$ alkyl, substituted C$_{1-12}$ alkyl, C$_{5-12}$ cycloalkyl, substituted C$_{5-12}$ cycloalkyl, C$_{5-12}$ aryl, and substituted C$_{5-12}$ aryl, —C(O)—OR$^{22}$ or —C(O)—R$^{22}$;

R$^{22}$ is C$_{1-12}$ alkyl, substituted C$_{1-12}$ alkyl, heteroalkyl, substituted heteroalkyl, C$_{3-12}$ cycloalkyl, substituted C$_{3-12}$ cycloalkyl, C$_{4-20}$ cycloalkylalkyl, substituted C$_{4-20}$ cycloalkylalkyl, C$_{4-20}$ heterocycloalkylalkyl, substituted C$_{4-20}$ heterocycloalkylalkyl, C$_{5-12}$ aryl, substituted C$_{5-12}$ aryl, C$_{5-12}$ heteroaryl, substituted C$_{5-12}$ heteroaryl, C$_{6-20}$ arylalkyl, substituted C$_{6-20}$ arylalkyl, C$_{6-20}$ heteroarylalkyl or substituted C$_{6-20}$ heteroarylalkyl; and R$^{48}$ is C$_{1-12}$ alkyl or substituted C$_{1-12}$ alkyl.

2. The compound of claim 1, wherein R$^1$ is hydrogen, —OR$^2$, —C(O)OR$^2$, or —C(O)R$^2$.

3. The compound of claim 1, wherein each R$^2$ and R$^{22}$ is independently C$_{1-6}$ alkyl, substituted C$_{1-6}$ alkyl, C$_{3-7}$ cycloalkyl, substituted C$_{3-7}$ cycloalkyl, C$_{5-7}$ aryl or substituted C$_{5-7}$ aryl.

4. The compound of claim 1, wherein each R$^2$ and R$^{22}$ is independently hydrogen, methyl, ethyl, n-propyl, isopropyl, dodecyl, tert-butyl, phenyl or cyclohexyl.

5. The compound of claim 1, wherein the substituted C$_{1-12}$ alkyl, substituted C$_{1-12}$ heteroalkyl, substituted C$_{3-12}$ cycloalkyl, substituted C$_{4-20}$ cycloalkylalkyl, substituted C$_{4-20}$ heterocycloalkylalkyl, substituted C$_{5-12}$ aryl, substituted C$_{5-12}$ heteroaryl, substituted C$_{6-20}$ arylalkyl, substituted C$_{6-20}$ heteroarylalkyl, or substituted C$_{5-12}$ cycloalkyl, is C$_{1-12}$ alkyl, C$_{1-12}$ heteroalkyl, C$_{3-12}$ cycloalkyl, C$_{4-20}$ cycloalkylalkyl, C$_{4-20}$ heterocycloalkylalkyl, substituted C$_{5-12}$ aryl, C$_{5-12}$ heteroaryl, C$_{6-20}$ arylalkyl, C$_{6-20}$ heteroarylalkyl, or C$_{5-12}$ cycloalkyl, respectively, substituted with one or more groups selected from halogen, —NO$_2$, —OH, —NH$_2$, —CN, —CF$_3$, —OCF$_3$, =O, C$_{1-12}$ alkyl, substituted C$_{1-12}$ alkyl, C$_{1-12}$ alkoxy or substituted C$_{1-12}$ alkoxy, —COOR$^{10'}$ wherein R$^{10'}$ is hydrogen, C$_{1-3}$ alkyl or —(NR$^{11'}$)$_2$ wherein each R$^{11'}$ is independently hydrogen or C$_{1-3}$ alkyl.

6. The compound of claim 1, wherein the compound of Formula (I) is a compound of Formula (X), Formula (XI) Formula (XII), Formula (XIII), Formula (XIV), Formula (XV), Formula (XVa) or Formula (XVb) or a pharmaceutically acceptable salt, tautomer or stereoisomer thereof;

wherein the compound of Formula (X) is:

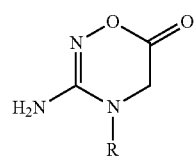

(X)

Wherein R is —CH$_3$ or —CD$_3$;
wherein the compound of Formula (XI) is:

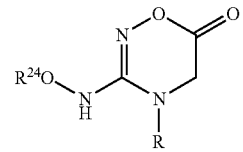

(XI)

Wherein R is —CH$_3$ or —CD$_3$; and
R$^{24}$ is hydrogen, methyl, ethyl, n-propyl, isopropyl, tert-butyl, dodecyl, phenyl or cyclohexyl;
wherein the compound of Formula (XII) is:

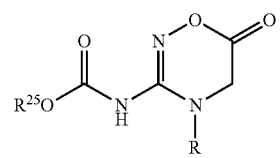

(XII)

wherein R is —CH$_3$ or —CD$_3$; and
R$^{25}$ is hydrogen, methyl, ethyl, n-propyl, isopropyl, tert-butyl, dodecyl, phenyl or cyclohexyl;
wherein the compound of Formula (XIII) is:

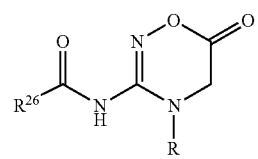

(XIII)

wherein R is —CH$_3$ or —CD$_3$; and
R$^{26}$ is hydrogen, methyl, ethyl, n-propyl, isopropyl, tert-butyl, dodecyl, phenyl or cyclohexyl;
wherein the compound of Formula (XIV) is:

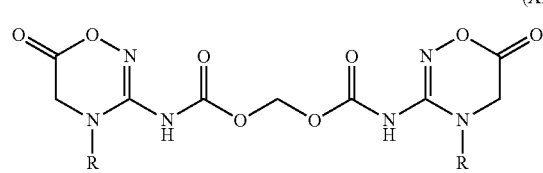

(XIV)

wherein R is —CH$_3$ or —CD$_3$;
wherein the compound of Formula (XV) is:

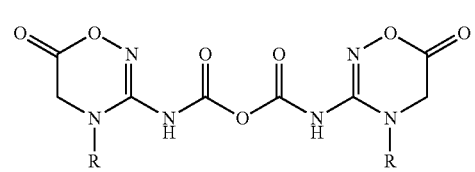

(XV)

wherein R is —CH₃ or —CD₃;
wherein the compound of Formula (XVa) is:

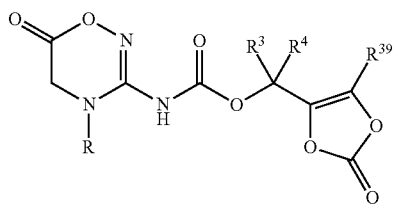

(XVa)

wherein R is —CH₃ or —CD₃;
R$^{39}$ is hydrogen, methyl, ethyl, n-propyl, isopropyl, tert-butyl, dodecyl, phenyl or cyclohexyl; and
R$^3$ and R$^4$ are each independently hydrogen, C$_{1-12}$ alkyl or substituted C$_{1-12}$ alkyl;
wherein the compound of Formula (XVb) is:

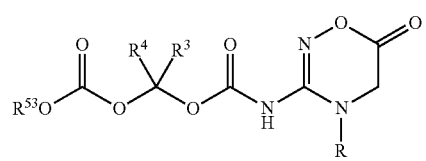

(XVb)

wherein R is —CH₃ or —CD₃;
R$^3$ and R$^4$ are each independently hydrogen, C$_{1-12}$ alkyl or substituted C$_{1-12}$ alkyl; and
R$^{53}$ is C$_{1-12}$ alkyl or substituted C$_{1-12}$ alkyl.

7. The compound of claim 1, which is selected from the group consisting of

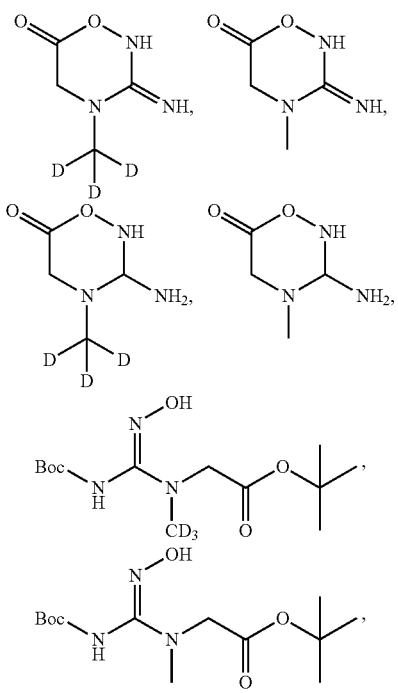

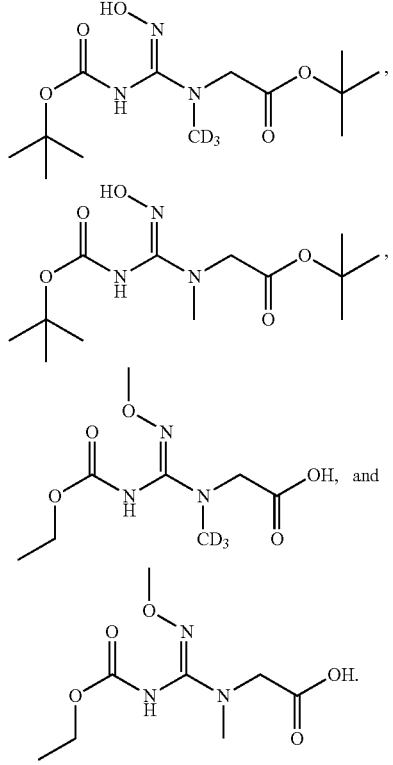

8. A pharmaceutical composition comprising a therapeutically effective amount of at least one compound of claim 1, and a pharmaceutically acceptable vehicle.

9. The pharmaceutical composition of claim 8, which is in one or more sustained release oral dosage forms.

10. The pharmaceutical composition of claim 8, wherein the at least one compound is present in an amount effective for the treatment of a disease in a patient wherein the disease is ischemia, oxidative stress, a neurodegenerative disease, ischemic reperfusion injury, a cardiovascular disease, a genetic disease affecting the creatine kinase system, multiple sclerosis, a psychotic disorder, and muscle fatigue; an amount sufficient to effect energy homeostasis in a tissue or an organ affected by a disease; an amount effective for the enhancement of muscle strength in a patient; an amount effective for the improvement of the viability of a tissue or an organ; or an amount effective for the improvement of the viability of cells.

11. The pharmaceutical composition of claim 8, wherein the at least one compound is present in an amount effective for the treatment of a genetic disease affecting the creatine kinase system.

12. The pharmaceutical composition of claim 8, wherein the at least one compound is present in an amount effective for the treatment of a creatine transporter disorder.

13. The pharmaceutical composition of claim 8, wherein the at least one compound is present in an amount effective for the treatment of a creatine synthesis disorder.

* * * * *